US012233216B2

(12) United States Patent
Brodsky

(10) Patent No.: US 12,233,216 B2
(45) Date of Patent: Feb. 25, 2025

(54) IMMERSIVE MULTISENSORY SIMULATION SYSTEM

(71) Applicant: NEWTON VR LTD., Tel Aviv-Jaffa (IL)

(72) Inventor: Yuval Brodsky, Tel Aviv (IL)

(73) Assignee: NEWTON VR LTD., Tel Aviv-Jaffa (IL)

( * ) Notice: Subject to any disclaimer, the term of this patent is extended or adjusted under 35 U.S.C. 154(b) by 190 days.

(21) Appl. No.: 17/834,960

(22) Filed: Jun. 8, 2022

(65) Prior Publication Data

US 2022/0296848 A1 Sep. 22, 2022

Related U.S. Application Data

(63) Continuation of application No. 16/329,231, filed as application No. PCT/IL2017/050983 on Sep. 3, 2017, now Pat. No. 11,383,062.

(Continued)

(51) Int. Cl.
*A61M 21/00* (2006.01)
*A61H 3/00* (2006.01)
(Continued)

(52) U.S. Cl.
CPC ............. *A61M 21/00* (2013.01); *A61H 3/008* (2013.01); *A63B 22/02* (2013.01); *G05B 13/042* (2013.01);
(Continued)

(58) Field of Classification Search
CPC ... A63B 22/00; A63B 22/00181; A63B 22/02; A63B 22/0207; A63B 22/0228; A63B 22/0235; A63B 22/025; A63B 22/0257; A63B 22/0264; A63B 22/0285; A63B 22/0292; A63B 22/4001; A63B 22/4005; A63B 22/4007; A63B 22/40; A63B 2022/0271; A63B 2022/0278; A63B 2220/50; A63B 2220/51; A63B 2220/56; A63B 2220/805; A63B 24/0087; A63B 2024/009; A63B 2024/0093; A63B 2024/0096; A63B 69/0057;
(Continued)

(56) References Cited

U.S. PATENT DOCUMENTS 9,789,023 B1 * 10/2017 Lee .......................... A61H 3/00
2004/0143198 A1 * 7/2004 West .................... A61H 1/0262
601/5

(Continued)

*Primary Examiner* — Zachary T Moore
(74) *Attorney, Agent, or Firm* — Rivka Friedman

(57) ABSTRACT

A Multisensory Simulation System comprises systems including: an Omni-Directional Treadmill (ODT), a Gravity Modification System (GMS), a Motion and gesture Tracking System (MTS), a Data Analytics System (DAS), a Visual Stimulation System (VSS), an Auditory Stimulation System (AUSS), an Operator Interface System (OIS), a User Harness System (UHS), a Tactile Stimulation System (TSS), an Atmospheric Simulation System (ATSS), a Neurological Stimulation System (NSS), an Olfactory Stimulation System (OSS), a Gustatory System Stimulation System (GSS), a User Monitoring System (UMS), a Controller, a Game Engine System (GES), database, a Communication Unit (CU), a User Safety System (USS), and a communication bus.

22 Claims, 39 Drawing Sheets

Related U.S. Application Data

(60) Provisional application No. 62/382,279, filed on Sep. 1, 2016.

(51) Int. Cl.
*A63B 22/02* (2006.01)
*G05B 13/04* (2006.01)

(52) U.S. Cl.
CPC ............ *A61M 2021/0022* (2013.01); *A61M 2021/0027* (2013.01); *A61M 2021/005* (2013.01); *A61M 2205/056* (2013.01); *A63B 2022/0271* (2013.01)

(58) Field of Classification Search
CPC ............ A63B 69/0059; A63B 69/0064; A63B 2069/0062; A61H 3/008; A61H 2201/1621; A61H 2201/163; A61H 2201/1633; A61H 2201/1628; A61H 2201/1619; A61H 2201/165; A61H 2201/1652; A61H 1/0259; A61H 1/0262
USPC .......................................................... 482/69
See application file for complete search history.

(56) References Cited

U.S. PATENT DOCUMENTS

| | | | |
|---|---|---|---|
| 2012/0157859 A1* | 6/2012 | Hecquet | A63B 24/0062 600/484 |
| 2014/0100491 A1* | 4/2014 | Hu | A61H 3/008 601/23 |

* cited by examiner

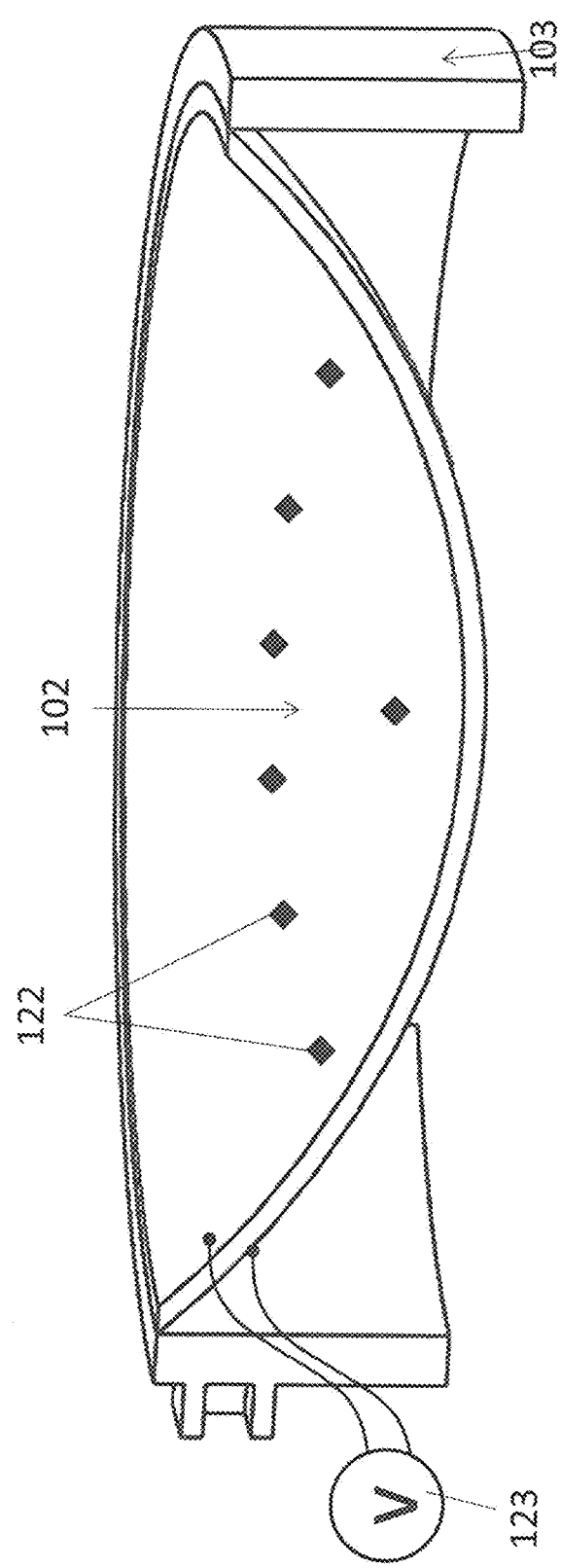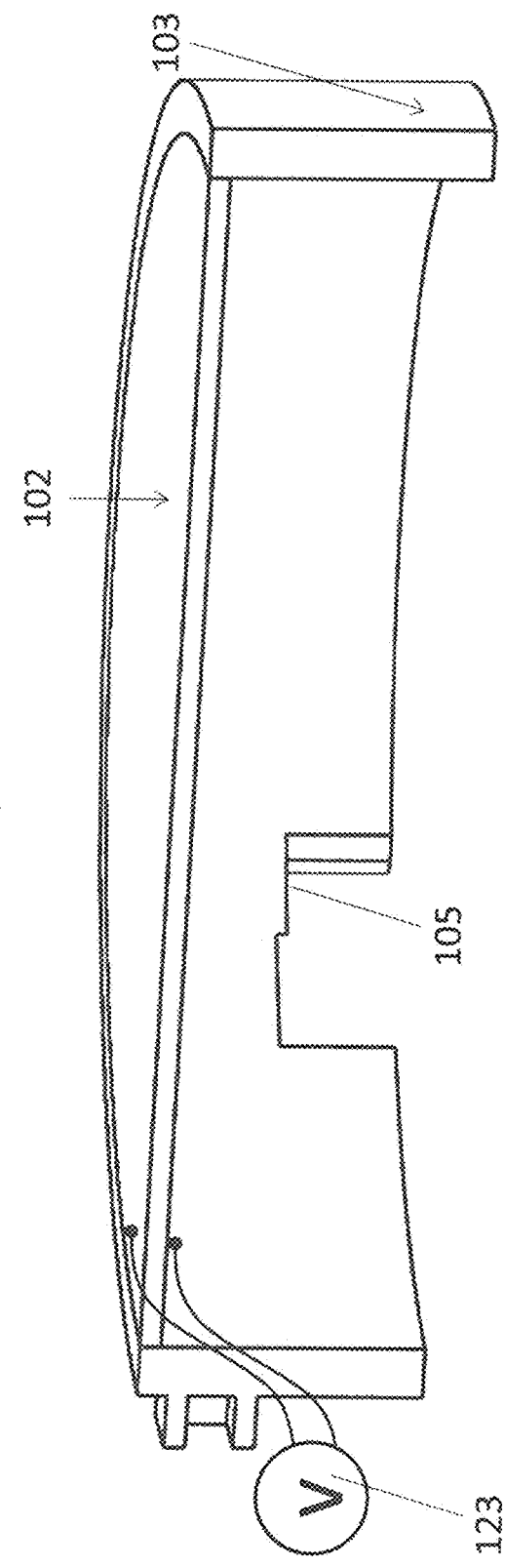
Fig. 3A
Fig. 3B

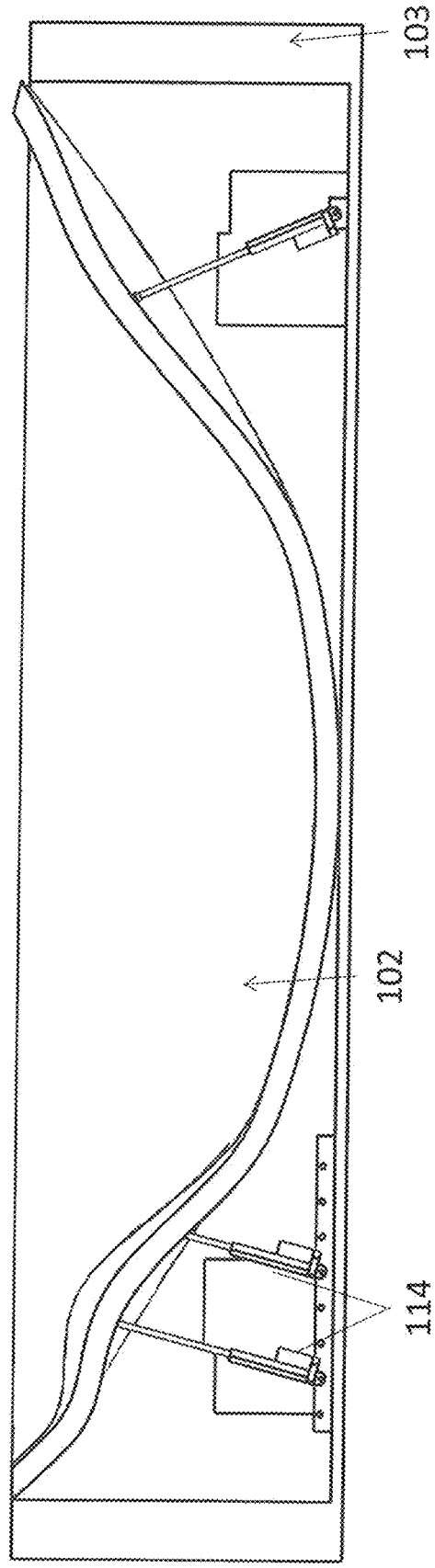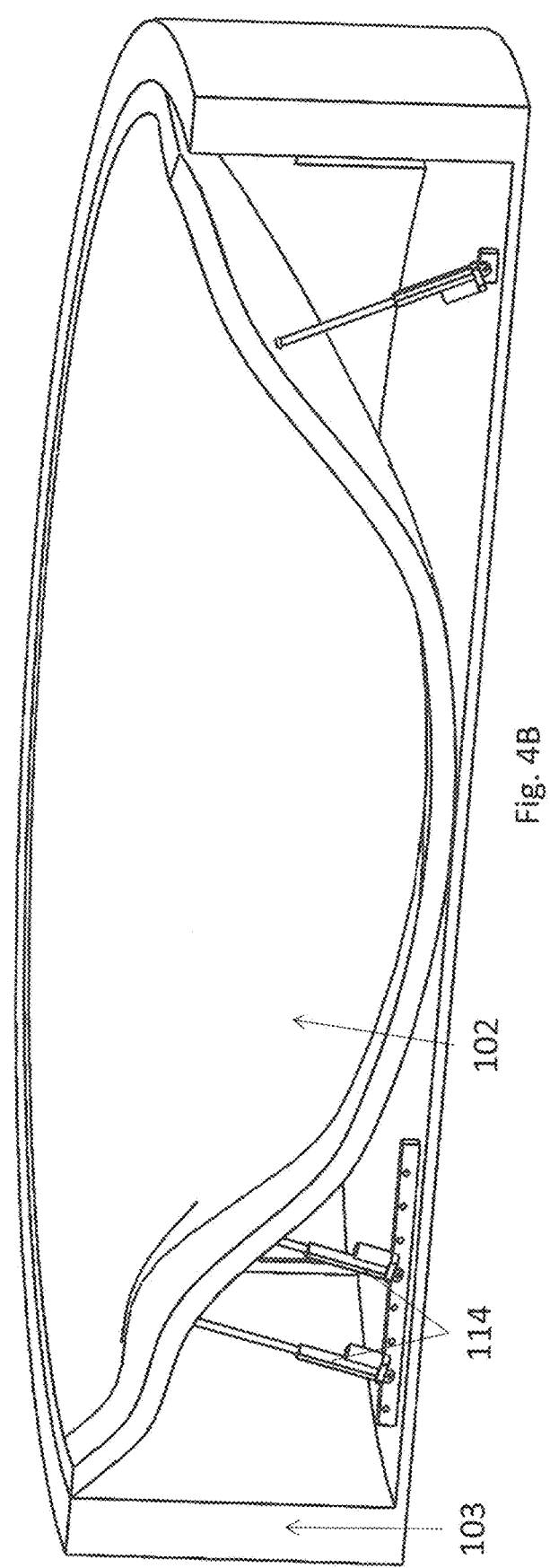

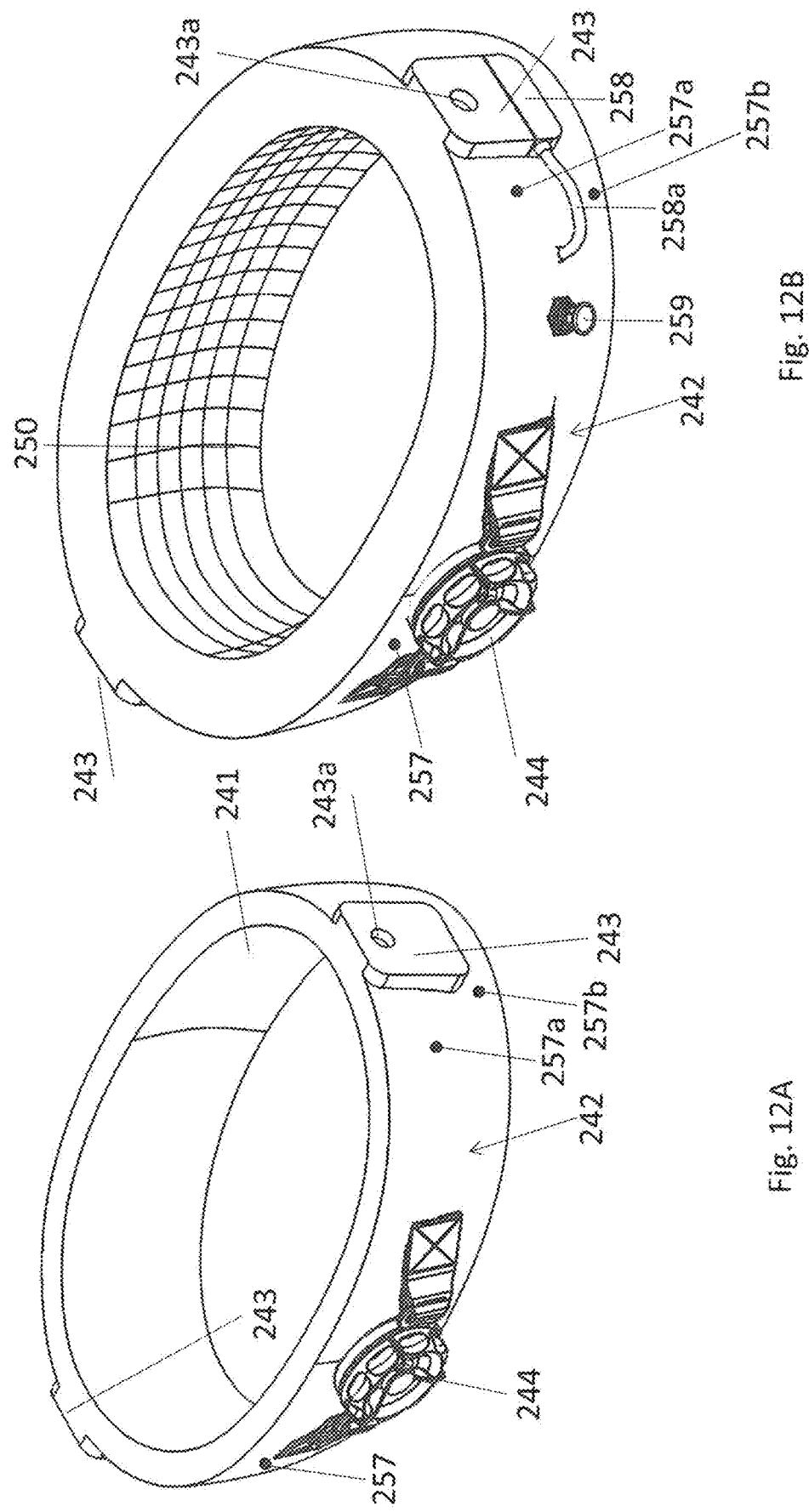

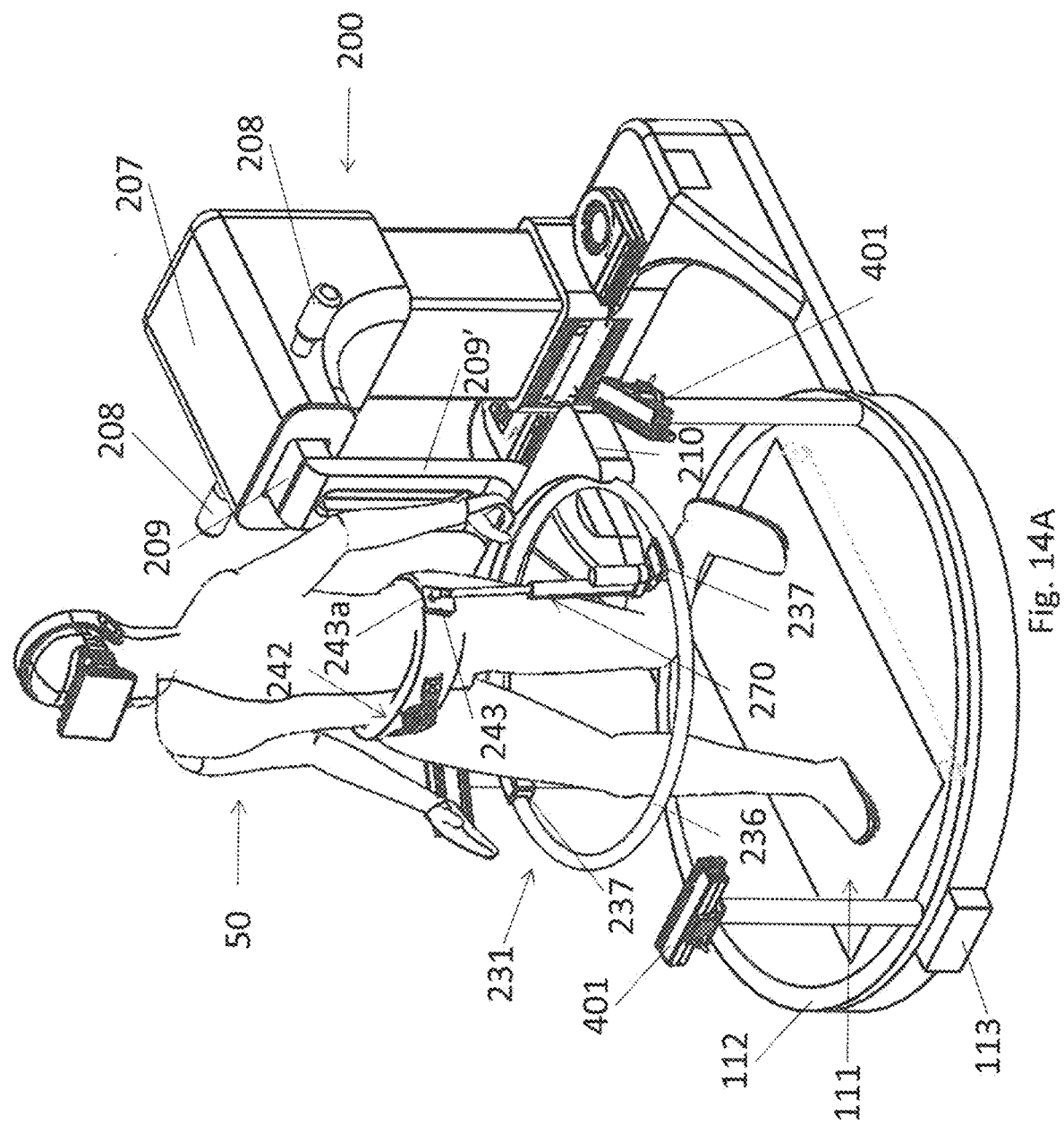

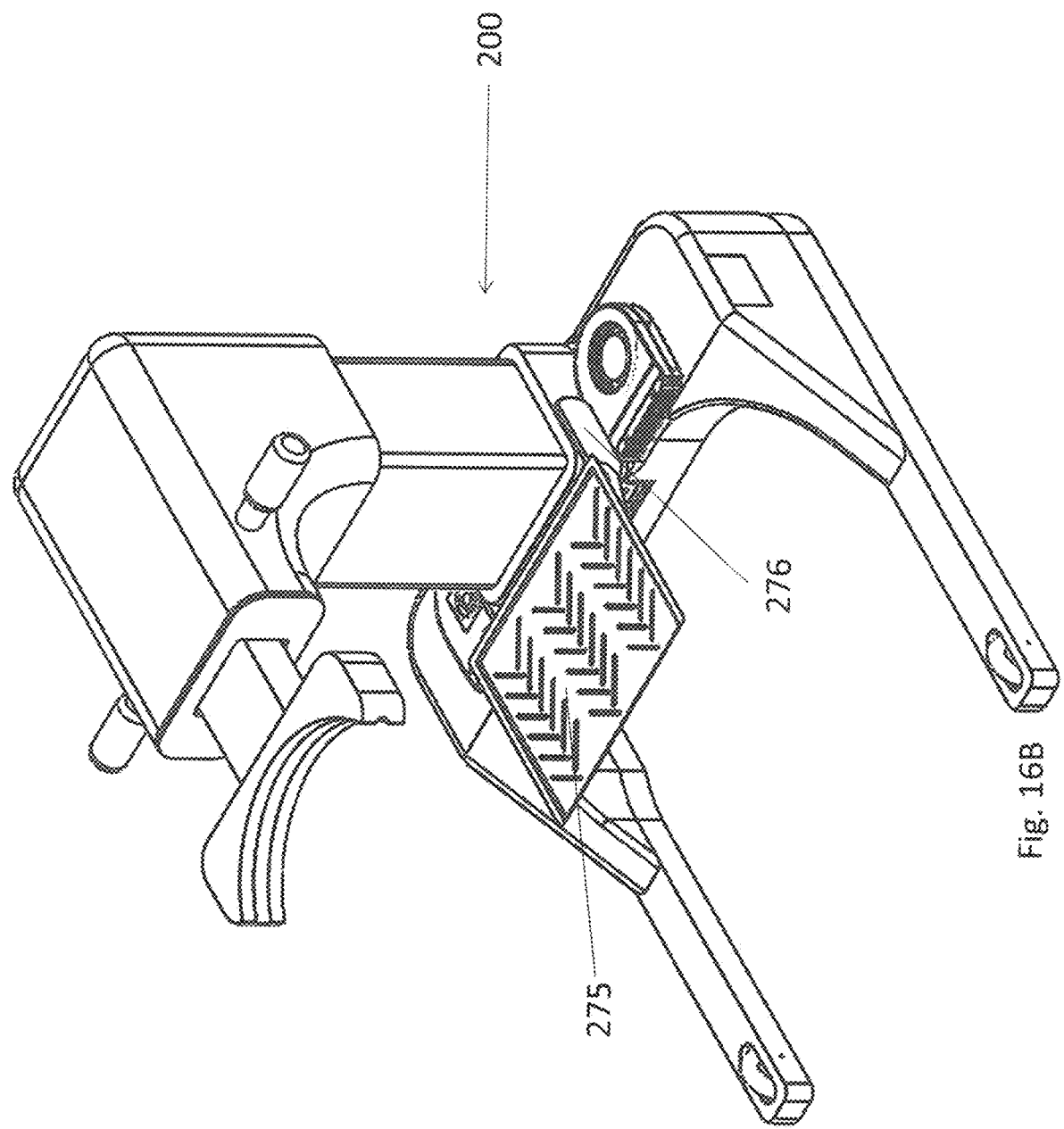

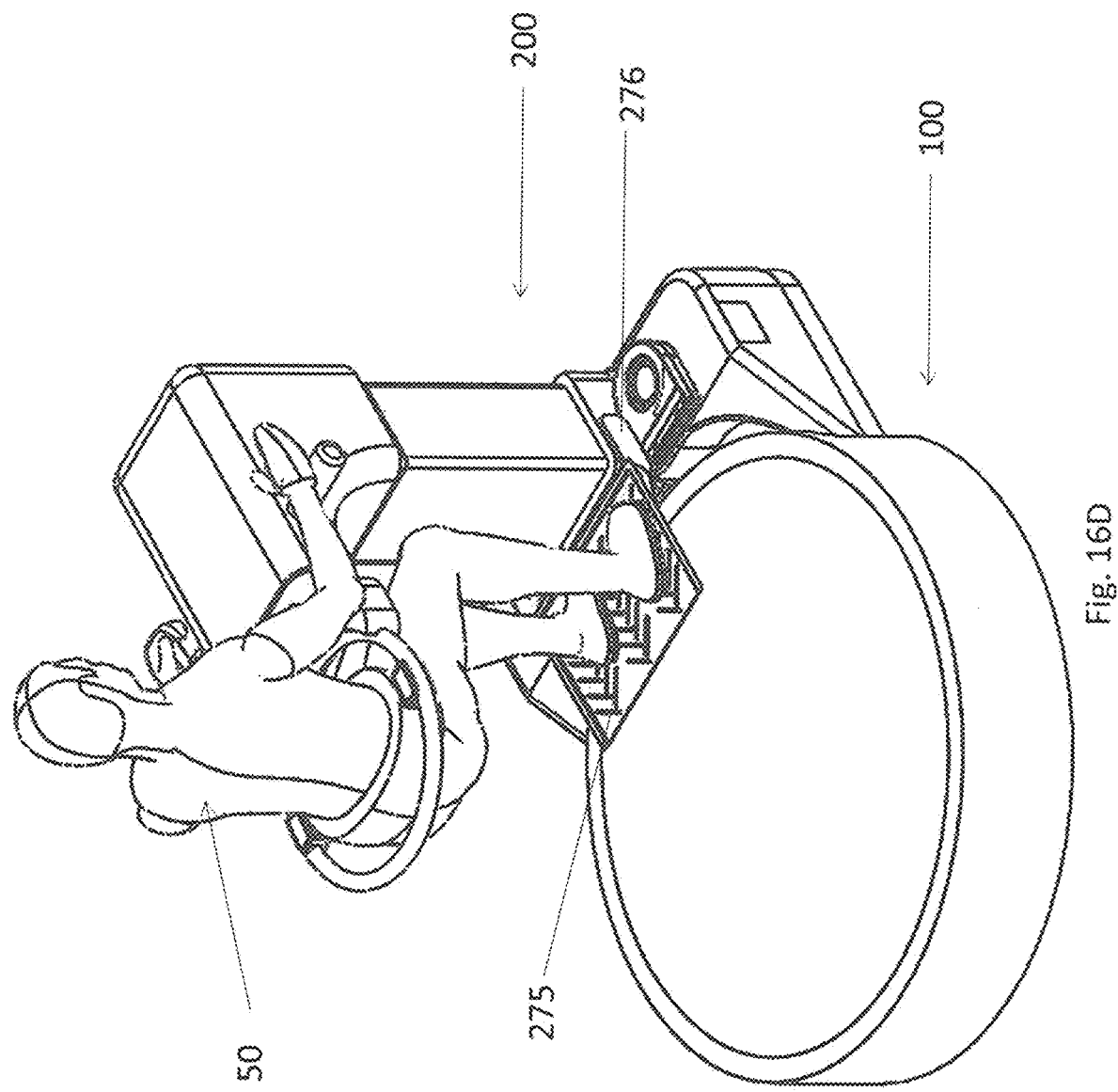

IMMERSIVE MULTISENSORY SIMULATION SYSTEM

CROSS-REFERENCES TO RELATED APPLICATIONS

This application is related to and claims priority from commonly owned U.S. Provisional Patent Application Ser. No. 62/382,279, entitled: Immersive Multisensory Simulation System, filed on Sep. 1, 2016, the disclosure of which is incorporated by reference in its entirety herein.

FIELD OF THE INVENTION

The invention relates to the field of immersive Multisensory Simulation Systems (MSS).

BACKGROUND OF THE INVENTION

Multisensory Simulation Systems are systems that stimulate many of the user's senses in order to simulate a novel environment or situation. As the number of user senses stimulated increases, so too does the fidelity of the simulation. Likewise, the accuracy with which each sense is stimulated increases the simulation fidelity.

SUMMARY OF THE INVENTION

The present invention provides an economical design for a Multisensory Simulation System (MSS), which includes multiple modular components.

Embodiments of the present invention include a Multisensory Simulation System, which may comprise: an Omni-Directional Treadmill (ODT), a Gravity Modification System (GMS), a Motion and gesture Tracking System (MTS), a Data Analytics System (DAS), a Visual Stimulation System (VSS), an Auditory Stimulation System (AUSS), an Operator Interface System (OIS), a User Harness System (UHS), a Tactile Stimulation System (TSS), an Atmospheric Simulation System (ATSS), a Neurological Stimulation System (NSS), an Olfactory Stimulation System (OSS), a Gustatory System Stimulation System (GSS), a User Monitoring System (UMS), a Controller, a Game Engine System (GES), database, a Communication Unit (CU), a User Safety System (USS), and a communication bus.

Embodiments of the present invention provide an Omni-Directional Treadmill (ODT) providing a physical apparatus within which the user may undergo the simulation. This ODT will allow the user to execute normal movements such as walking, running, jumping, crouching, and the like, in any direction while remaining within the space of the ODT. Such a device may be active or passive. The ODT may be integrated with the GMS, MTS, DAS, OIS, UHS, UMS, CONTROLLER (also referred to herein as Controller), GES, USS, or any other MSS subsystem(s).

Embodiments of the present invention provide a Gravity Modification System (GMS), which applies a force that is parallel or nearly parallel to the gravity vector, in the positive and/or negative directions, in order to simulate decreased or increased gravity, respectively. The GMS may be integrated with the ODT, MTS, DAS. OIS, UHS, UMS, Controller, GES, USS, or any other MSS subsystem(s).

Embodiments of the present invention provide a Motion and gesture Tracking System (MTS), whose function is to capture the user's movements, record them, and translate them into a useable data format that can be used by other subsystems of the MSS. Motion and gesture data may be integrated with the ODT, GMS. DAS, UHS, UMS, Controller, GES, USS, or any other MSS subsystem(s).

Embodiments of the present invention may include a Data Analytics System (DAS), whose function is to analyze data provided by other components of the MSS. Outputs from the DAS may or may not be used by other subsystems of the MSS.

Embodiments of the present invention provide a Visual Stimulation System (VSS), which presents visual stimuli to the user. These stimuli may correspond with the scene of the simulation. The visual data may be integrated with the ODT, GMS, MTS, Controller, GES, or any other MSS subsystem(s).

Embodiments of the present invention provide an Auditory Stimulation System (AUSS), which provides auditory stimuli to the user. These stimuli may correspond with the scene of the simulation. The auditory data may be integrated with the ODT, GMS, MTS, OIS, Controller, GES, or any other MSS subsystem(s).

Embodiments of the present invention may include an Operator Interface System (OIS), which provides an operator interface to control the MSS and its subsystems. The OIS allows for control of the simulated environment, hence may drive all of the MSS subsystems.

Embodiments of the present invention may include a User Harness System (UHS), which provides an interface between the user and the GMS.

Embodiments of the present invention provide a Tactile Stimulation System (TSS), which provides the user with tactile feedback from his/her interaction with the simulated environment. The tactile stimulation may correspond with the scene of the simulation. The tactile stimulation may be integrated with the ODT, GMS, MTS, OIS, Controller, GES, or any other MSS subsystem(s).

Embodiments of the present invention provide an Atmospheric Simulation System (ATSS), which simulates the atmospheric conditions in the scene of the simulation. The atmospheric simulation may correspond with the scene of the simulation. The atmospheric simulation may be integrated with the ODT, GMS, MTS, OIS, Controller, GES, or any other MSS subsystem(s).

Embodiments of the present invention provide a Neurological Stimulation System (NSS), whose function is to provide neurological stimulation to the user. The neurological stimulation may correspond with the scene of the simulation. The neurological stimulation may be integrated with the ODT, GMS. MTS, OIS, Controller, GES, or any other MSS subsystem(s).

Embodiments of the present invention provide an Olfactory Stimulation System (OSS), whose function is to provide olfactory stimulation to the user. The olfactory stimulation may correspond with the scene of the simulation. The olfactory stimulation may be integrated with the ODT, GMS, MTS, OIS, Controller, GES, or any other MSS subsystem(s).

Embodiments of the present invention provide a Gustatory System Stimulation System (GSS), whose function is to stimulate the gustatory system organs. The gustatory stimulation may correspond with the scene of the simulation. The gustatory stimulation may be integrated with the ODT, GMS, MTS, OIS, Controller, GES, or any other MSS subsystem(s).

Embodiments of the present invention may include a user monitoring system (UMS), whose function is to monitor parameters pertaining to the system's user. The UMS may be integrated with the, GMS, MTS, DAS, OIS, UHS, UMS, Controller, GES, USS, or any other MSS subsystem(s).

Embodiments of the present invention provide a MSS controller which provides initialization, configuration management, coordination and synchronization, logging, archiving, message delivery, load balancing, and security to the MSS and its subsystems.

Embodiments of the present invention provide a Game Engine System (GES), which provides the environment within which the simulation is conducted. The GES may be integrated with the GMS, MTS, DAS, OIS, UHS, UMS, Controller, GES, USS, or any other MSS subsystem(s). The GES may be driven by an MSS operator through the OIS, Controller or by the CU which sets the simulation environment parameters.

Embodiments of the present invention may include one or more databases, whose function is to store and allow access to data.

Embodiments of the present invention may include a Communication Unit (CU), whose function is to allow communication of the MSS, its systems, and subsystems with other MSSs and with any other external system(s).

Embodiments of the present invention may include a User Safety System (USS), whose function is to ensure the safety of user(s) and operator(s). The safety system may be driven by the GMS, MTS, DAS, OIS, UHS, UMS, Controller, GES, USS, or any other MSS subsystem(s).

Embodiments of the present invention may include a communication bus, whose function is to allow communication between any and all of the MSS systems and subsystems.

Embodiments of the present invention are directed to a gravity simulation system. The system comprises: a device for receiving a user, for example, a harness, belt or the like; and, a force applying unit in communication with the user receiving device, the force applying unit configured for applying positive and negative force to the user receiving device in a direction substantially parallel to a gravity vector.

Optionally, the gravity simulation system additionally comprises: a controller in communication with the force applying unit, the controller for controlling the amount of positive or negative force to simulate a predetermined force, and the predetermined force corresponding to at least one of a predetermined gravity or a predetermined body weight.

Optionally, the force applying unit is configured for applying a predetermined force, the predetermined force corresponding to at least one of a predetermined gravity or a predetermined body weight.

Optionally, the user receiving device is configured for allowing user movement in a 360 degree rotation.

Optionally, the user receiving device and/or the force applying unit are configured for allowing user movement in multiple degrees of freedom.

Optionally, the multiple degrees of freedom include angular degrees of freedom, defined by roll, pitch and yaw.

Optionally, the multiple degrees of freedom include linear degrees of freedom, defined by forward/backward, up/down and left/right.

Optionally, the gravity simulation system additionally comprises: a controller in communication with the force applying device for controlling at least one of the multiple degrees of freedom.

Optionally, the user receiving device includes a harness movably mounted in a support member.

Optionally, the harness is positioned above the support member.

Optionally, the user receiving device is configured to accommodate the user in the natural gait of the user.

Optionally, the user receiving device includes actuators, the actuators in communication with the harness and in pivotal communication with the support member.

Optionally, the user receiving device is configured to accommodate multiple user hip widths.

Optionally, the support member is mounted to an adapter member of the force applying unit.

Optionally, the adapter member is rotatably mounted on the force applying unit.

Optionally, the user receiving device includes a harness including motion tracking and/or physiological parameter (e.g., condition) sensors.

Optionally, the harness is inflatable.

Optionally, the force applying unit includes a vertically moving member in communication with the adapter member.

Optionally, the gravity simulation system additionally comprises: a locomotion support device including a surface for supporting the user in the user receiving device.

Optionally, the locomotion support device includes at least one of: a treadmill, an omnidirectional treadmill, and, a stepper.

Optionally, the surface of the locomotion support device is moveable.

Optionally, the surface of the locomotion support device is configured for changing at least one of: shape, texture and friction.

Optionally, the locomotion support device is separable to receive the user.

Optionally, the force applying unit is configured for moving between a first elevation, where the user is in a sitting position in the user receiving device, and a second elevation, where the user is in a standing position in the user receiving device.

Optionally, the gravity simulation system additionally comprises: a visual stimulation system for providing a visual environment.

Optionally, the user receiving device and/or the force applying unit are configured to accommodate the user in the natural gait of the user.

Optionally, the force applying unit is movable by the user in the user receiving device.

Optionally, the force applying unit includes a platform for supporting the user.

Embodiments of the present invention are directed to a gravity simulation system comprising: a device for receiving a user; a force applying unit in communication with the user receiving device, the force applying unit configured for applying at least one of a positive or negative force to the user receiving device in a direction substantially parallel to a gravity vector; and, an omnidirectional treadmill in communication with the force applying unit, the omnidirectional treadmill for supporting the user in the user receiving device and confining locomotion of the user to a predetermined area of the omnidirectional treadmill.

Optionally, the gravity simulation system additionally comprises: a controller in communication with the force applying unit, the controller for controlling the amount of positive or negative force to simulate a predetermined force.

Optionally, the predetermined force corresponds to at least one of a predetermined gravity or a predetermined body weight.

Optionally, the force applying unit is configured for applying a predetermined force, the predetermined force corresponding to at least one of a predetermined gravity or a predetermined body weight.

Optionally, user receiving device and/or the force applying unit are configured for allowing user movement in a 360 degree rotation.

Optionally, the user receiving device and/or the force applying unit are configured for allowing user movement in multiple degrees of freedom.

Optionally, the multiple degrees of freedom include angular degrees of freedom, defined by roll, pitch and yaw.

Optionally, the multiple degrees of freedom include linear degrees of freedom, defined by forward/backward, up/down and left/right.

Optionally, the gravity simulation system additionally comprises a controller in communication with the force applying device for controlling at least one of the multiple degrees of freedom.

Optionally, the user receiving device includes a harness movably mounted in a support member.

Optionally, the user receiving device includes a harness movably mounted in a support member.

Optionally, the user receiving device is configured to accommodate multiple user hip widths.

Optionally, the support member is mounted to an adapter member of the force applying unit.

Optionally, the adapter member is rotatably mounted on the force applying unit.

Optionally, the user receiving device includes a harness including motion tracking and physiological parameter (e.g., condition) sensors.

Optionally, the harness is inflatable.

Optionally, the harness is positioned above the support member.

Optionally, the user receiving device is configured to accommodate the user in the natural gait of the user.

Optionally, the force applying unit includes a vertically moving member in communication with the adapter member.

Optionally, the force applying unit is movable by the user in the user receiving device.

Optionally, the surface of the omnidirectional treadmill is moveable.

Optionally, the surface of the omnidirectional treadmill is configured for changing at least one of: shape, texture and friction.

Optionally, wherein the omnidirectional treadmill is separable to receive the user.

Optionally, the force applying unit is configured for moving between a first elevation, where the user is in a sitting position in the user receiving device, and a second elevation, where the user is in a standing position in the user receiving device.

Optionally, the gravity simulation system additionally comprises: a visual stimulation system for providing a visual environment.

Optionally, the user receiving device is configured to accommodate the user in the natural gait of the user.

Embodiments of the invention are directed to a harness unit. The harness unit comprises: a harness configured for receiving a user, first sensors including motion tracking sensors; and, second sensors including physiological parameter sensors.

Optionally, the harness is inflatable.

Optionally, the harness includes a plurality of inflatable internal compartments.

Optionally, the harness is configured for receiving a user at the midsection of the user.

Embodiments of the invention are directed to an omnidirectional treadmill (ODT). The ODT comprises: a base for supporting a surface, the surface defining an area in which locomotion of a user is confined, and, the surface is configured for changing one or more of shape, texture and friction.

Optionally, the surface is moveable.

Optionally, the ODT additionally comprises: a processor programmed for changing one or more of shape, texture and friction, of the surface.

Optionally, the ODT additionally comprises: at least one sensor associated with the surface for motion detection of a user.

Optionally, the ODT additionally comprises: an imaging system for imaging the user; and, a processor programmed to receive at least one image from the imaging system and the data from the at least one motion detection sensor to analyze motion of the user.

Optionally, the surface is separable to receive a user.

Optionally, the base includes a support member arranged in a honeycomb shape.

Optionally, the base includes a support member of foam.

Embodiments of the invention are directed to a gravity simulation system, which comprises: a device for receiving a user; a force applying unit in communication with the user receiving device, the force applying unit configured for applying at least one of a positive or negative force to the user receiving device in a direction substantially parallel to a gravity vector; and, a visual stimulation system for providing a visual environment.

Optionally, the gravity simulation system additionally comprises: a controller in communication with the force applying unit, the controller for controlling the amount of positive or negative force to simulate a predetermined force, and, the predetermined force corresponds to at least one of a predetermined gravity or a predetermined body weight.

Optionally, the force applying unit is configured for applying a predetermined force, the predetermined force corresponding to at least one of a predetermined gravity or a predetermined body weight.

Optionally, the user receiving device is configured for allowing user movement in a 360 degree rotation.

Optionally, the user receiving device is configured for allowing user movement in multiple degrees of freedom.

Optionally, the multiple degrees of freedom include angular degrees of freedom, defined by roll, pitch and yaw.

Optionally, the multiple degrees of freedom include linear degrees of freedom, defined by forward/backward, up/down and left/right.

Optionally, the gravity simulation system additionally comprises a controller in communication with the force applying device for controlling at least one of the multiple degrees of freedom.

Optionally, the user receiving device includes a harness movably mounted in a support member.

Optionally, the user receiving device is configured to accommodate multiple user hip widths.

Optionally, the support member is mounted to an adapter member of the force applying unit.

Optionally, the adapter member is rotatably mounted on the force applying unit.

Optionally, the user receiving device includes a harness including motion tracking and physiological parameter (e.g., condition) sensors.

Optionally, the harness is inflatable.

Optionally, the harness is positioned above the support member.

Optionally, the gravity simulation system is configured to accommodate the user in the natural gait of the user.

Optionally, the force applying unit includes a vertically moving member in communication with the adapter member.

Optionally, the gravity simulation system additionally comprises: a locomotion support device including a surface for supporting the user in the user receiving device.

Optionally, the locomotion support device includes at least one of: a treadmill, an omnidirectional treadmill, and, a stepper.

Optionally, the surface of the locomotion support device is moveable.

Optionally, the surface of the locomotion support device is configured for changing at least one of: shape, texture and friction.

Optionally, the locomotion support device is separable to receive the user.

Optionally, the force applying unit is configured for moving between a first elevation, where the user is in a sitting position in the user receiving device, and a second elevation, where the user is in a standing position in the user receiving device.

Optionally, the force applying structure is movable by the user in the user receiving device.

Embodiments of the invention are directed to a method for gravity modification. The method comprises: receiving a user in a user receiving device, the user receiving device in communication with a force applying unit; determining a force to be applied on the user; causing the force applying unit to apply the determined force to the user in the user receiving device, by applying the force in a direction of a gravity vector; continuously monitoring the force being applied; and, adjusting the force being applied such that the applied force remains constant on the user.

Optionally, the force applied is positive.

Optionally, the force applied is negative.

Optionally, the adjusting the force is performed dynamically and in real time.

Embodiments of the invention are directed to a method for performing therapy to treat a mammalian, e.g., human, condition. The method comprises: providing systems for stimulating senses, including: tactile senses, auditory senses, visual senses, vestibular senses and proprioceptive senses; and, coordinating the provided systems to simulate a real environment.

Optionally, the method for performing the therapy additionally comprises: providing at least one additional system for stimulating senses including neurological, olfactory, and gustatory, or nervous systems.

Optionally, the mammalian condition includes wherein the mammalian medical condition includes one or more of: neurological condition, cerebrovascular accident, Parkinson's disease, neurodegenerative disease, orthopedic conditions, cardiac conditions, respiratory conditions, vestibular conditions, and, musculoskeletal conditions.

Throughout this document, references are made to directions and orientations, such as top, bottom, upper, lower, front, back (rear), forward, backward (rearward), up, down, left, right, proximal, distal, in singular and plural forms, and derivatives thereof. The use of these terms is for explanation purposes, to show the invention in example orientations and positions, and are in no way limiting.

"Linked" as used herein includes both wired or wireless links, either direct or indirect, and placing the systems, subsystems, computers, controllers, processing units, processors, databases, components and the like, in electronic and/or data communications with each other, and also over communications networks, such as local area networks and wide area networks such as the Internet, to computers, systems and the like.

BRIEF DESCRIPTION OF THE DRAWINGS

Some embodiments of the present invention are described herein, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIGS. 3A, 3B, 4A and 4B are cross-sectional views of embodiments of the surface of the omnidirectional treadmill of FIG. 1A;

FIG. 12A is a perspective view of the harness unit in a deflated state;

FIG. 12B is a perspective view of the harness of the harness unit in an inflated state;

FIGS. 14A and 14B-1 are perspective views showing user operation of an apparatus in accordance with other embodiments of the invention;

FIG. 14B-2 is a front view of another embodiment of the GMS;

FIGS. 16A-16E are perspective views showing the GMS including a platform, and user operation of the apparatus;

FIGS. 22A-1, 22A-2 and 22B are a flow diagram of a simulation process performed by the apparatus and systems of the invention; and, FIGS. 23A and 23B are block diagrams of multi user simulation configurations.

DETAILED DESCRIPTION OF THE INVENTION

The present invention discloses a Multisensory Simulation System (MSS) 75, an apparatus and system, and methods for its use. The MSS 75 enables a user to experience the sensory inputs of a simulated environment at a high fidelity.

The invention includes multiple apparatus, defining subsystems that improve the simulation fidelity. The subsystems can be used in various arrangements, with various subsystems used together, depending on a particular application.

The invention may be used, for example, in applications such as: physiotherapy, astronaut training, education, travel and tourism, personnel training, research, museums, real estate, healthcare, exploration, military, resource exploitation, athletics, architecture, film production, search and rescue, video games, entertainment, design, space exploration, robotics.

The apparatus of the invention is such that the subsystems include: a) an Omni-Directional Treadmill (ODT), b) a Gravity Modification System (GMS), c) a Motion and gesture Trucking System (MTS), d) a Data Analytics System (DAS), e) a Visual Stimulation System (VSS), f) an Auditory Stimulation System (AUSS), g) an Operator Interface System (OIS), h) a User Harness System (UHS), i) a Tactile Stimulation System (TSS), j) an Atmospheric Simulation System (ATSS), k) a Neurological Stimulation System (NSS), l) an Olfactory Stimulation System (OSS), m) a Gustatory System Stimulation System (GSS), n) a User Monitoring System (UMS), o) a Controller, p) a Game Engine System (GES), q) a database, r) a Communication Unit (CU), and s) a User Safety System (USS).

Figure 1A:
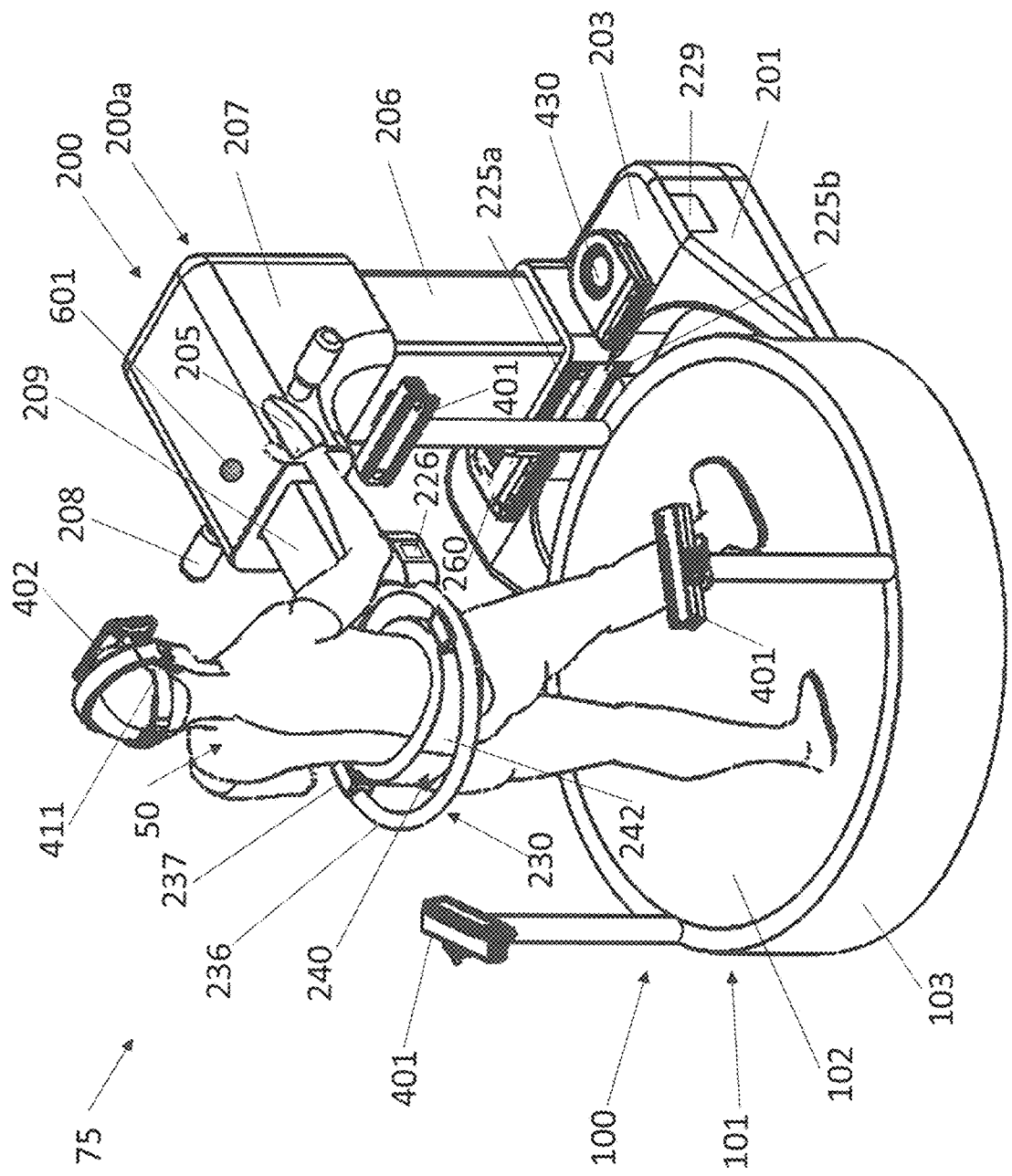
FIG. 1A is a perspective view of apparatus in accordance with embodiments of the invention.
Figure 1B:
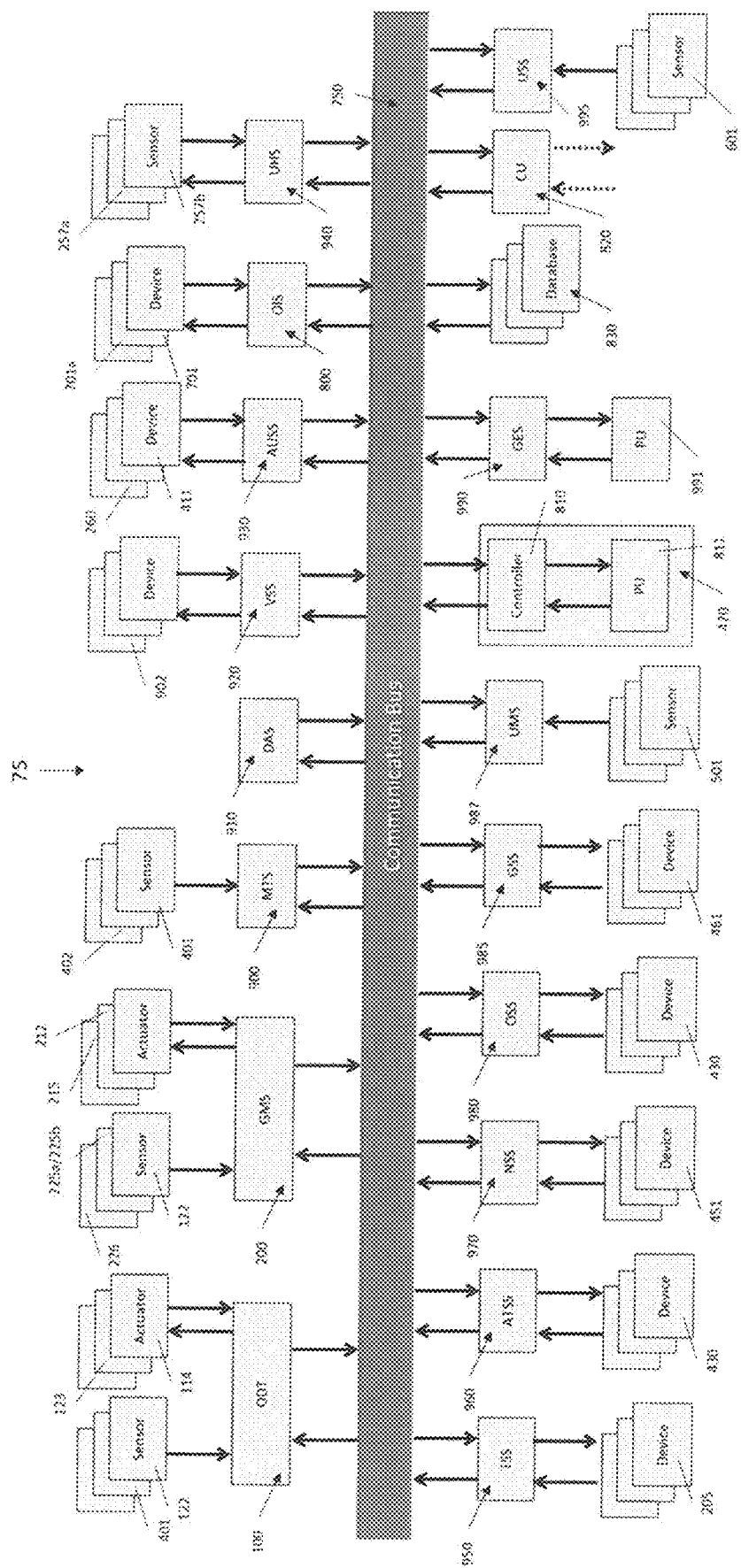
FIG. 1B is a block diagram of the systems of the apparatus of FIG. 1A.

FIG. 1A shows a user 50 in an embodiment of the MSS 75, comprising an ODT 100 in use with a mobile embodiment of a GMS 200. The GMS 200 is shown as a force applying unit 200a connected to a user harness system 940 (FIG. 1B), which includes a harness unit 240, which serves as a device for receiving the user 50 (also referred to as a user receiving device). The GMS 200 also includes, for example, systems such as a VSS 920, an AUSS 930, a USS 995, an ATSS 960, and an MTS 900, as shown in FIG. 1B. Together, these subsystems provide the user 50 with an immersive and safe simulation experience.

Attention is now also directed to FIG. 1B, a block diagram of the MSS 75 and its dataflow. The system includes a communication bus 750, which is linked to the operator interface 701 (also shown in FIG. 7), and the system computer 470 (also shown in FIG. 7), by wired and/or wireless links.

The operator interface 701 (FIG. 7) is part of an operator interface system (OIS) 800, which although the operator interface is shown as a touchscreen or being able to accommodate a keyboard for input entry, can also communicate electronically, by wired and/or wireless links, with a remote control unit 701a, from which operator input is received.

A system controller 810, formed of one or more processing unit(s) (PU) 811, 991, for example CPUs 811 and GPUs 991, is also linked to the communication bus 750. This system controller 810 controls the operations of the connected systems, including for example, the ODT 100, GMS 200, MTS 900, DAS 910, VSS 920, AUSS 930, OIS 800, UHS 940, TSS 950, ATSS 960, NSS 970, OSS 980, GSS 985, UMS 987, GES 990, Database(s) 830, communications unit (CU) 820, and USS 995. The system controller 810 synchronizes the systems and controls the devices associated therewith.

A communications unit 820 also links to the communication bus 750. This communications unit facilitates communications links to and from networks, such as the Internet and other online or offline links to network destinations. There is also one or more database(s) 830, wherein data is stored, linked to the communication bus 750. The database(s) 830 may be external to the computer 470.

The ODT 100 links to the communication bus 750. The ODT 100 receives input from sensors 122, and imaging units 401 (e.g., cameras), and inputs from and outputs to actuators 114 and voltage sources 123. The ODT 100 may receive data from and/or transmit data to any other MSS subsystems through the communication bus 750.

The GMS 200 links to the communication bus 750. The GMS 200 receives input from sensors 122, 225a, 225b, 226, 257a and 257b. The GMS 200 receives inputs from and sends outputs to motors 212, 215. The GMS 200 may receive data from and/or transmit data to any other MSS subsystems through the communication bus 750.

The Motion Tracking system (NTS) 900 links to the communication bus 750. The MTS 900 receives input from imaging devices 401, the VSS sensor(s) 402, and motion tracking sensor 257b. The MTS 900 may receive data from and/or transmit data to any other MSS subsystems through the communication bus 750.

A data analysis system (DAS) 910 links to the communication bus 750. The DAS 910 receives input for example, from the MTS 900, database 830, GES 990, controller 810. The DAS 910 operates to provide application specific data analysis and analytics to the other MSS systems, and/or the user, and/or the operator. The DAS 910 may also be external to the computer 470. The DAS 910 may receive data from and/or transmit data to any other MSS subsystems through the communication bus 750.

The Visual Stimulation System (VSS) 920 links to the communication bus 750. The VSS 920 sends output to a visual interface device, for example, a VR headset 402 (FIG. 1A). The visual outputs sent to the visual interface device may for example, correspond to the simulation and be driven by the controller or the GES. The VSS 920 receives inputs, for example, from the MTS 900, DAS 910, and GES 990. The VSS 920 may receive data from and/or transmit data to any other MSS subsystems through the communication bus 750.

The Auditory Stimulation System (AUSS) 930 links to the communication bus 750. The AUSS 930 sends output, for example, to the headset 411 and speakers 260. The AUSS 930 receives inputs, for example, from the MTS 900, and GES 990. The AUSS 930 may receive data from and/or transmit data to any other MSS subsystems through the communication bus 750.

The User Harness System (UHS) 940 links to the communication bus 750. The UHS 940 receives input as to conditions of the harness 242 and sensors 257a and 257b of the harness unit 240. The UHS 940 may receive data from and/or transmit data to any other MSS subsystems through the communication bus 750.

The Tactile Stimulation system (TSS) 950 links to the communication bus 750. The TSS 920 sends output to tactile actuators, for example, gloves 205. The TSS 950 receives inputs from the MTS 900, DAS 910, and GES 990. The TSS 950 may receive data from and/or transmit data to any other MSS subsystems through the communication bus 750.

The Atmospheric Stimulation System (ATSS) 960 links to the communication bus 750. The ATSS 960 sends output to the actuators, emitters, absorbers, as represented by port 430. The ATSS 960 receives inputs from the MTS 900, DAS 910, and GES 990. The ATSS 960 may receive data from and/or transmit data to any other MSS subsystems through the communication bus 750.

The Neurological Stimulation System (NSS) 970 links to the communication bus 750. The NSS 970 sends output to stimulators, for example, the electrodes 451 for stimulating the nervous system of a user. The NSS 970 receives inputs from the MTS 900. DAS 910, and GES 990. The NSS 970 may receive data from and/or transmit data to any other MSS subsystems through the communication bus 750.

The Olfactory Stimulation System (OSS) 980 links to the communication bus 750. The OSS 980 sends signals the emitter 430 for stimulating the olfactory system of a user. The OSS 980 receives inputs from the MTS 900, DAS 910, and GES 990. The OSS 980 may receive data from and/or transmit data to any other MSS subsystems through the communication bus 750.

The Gustatory System Stimulation System (GSS) 985 links to the communication bus 750. The GSS 985 sends output to gustatory stimulators, for example the electrode 461 for stimulating the tongue of a user. The GSS 985 receives inputs from the MTS 900, DAS 910, and GES 990. The GSS 985 may receive data from and/or transmit data to any other MSS subsystems through the communication bus 750.

The User Monitoring System (UMS) 987 links to the communication bus 750. The UMS 987 receives input from one or more sensor(s), for example electrodes 501 from various locations on the body of a user. The UMS 987 may receive data from and/or transmit data to any other MSS subsystems through the communication bus 750.

The Game Engine System (GES) 990 links to the communication bus 750. The GES 990 receives inputs from the operator, via operator interface 701, runs a desired simulation, and sends outputs, for example, to the DAS, database (s), and stimulation devices. The GES 990 includes one or more processing unit(s) (PU) 991. The GES 990 receives inputs from the MTS 900, DAS 910, GMS 200, ODT 100, and UHS 940 The GMS 990 may receive data from and/or transmit data to any other MSS subsystems through the communication bus 750.

The User Safety System (USS) 995 links to the communication bus 750. The USS 995 receives inputs from sensors and actuators throughout the MSS 75, for example, the emergency shut off button 601 or other emergency shut off, from the USS 995, as well as from the UMS 987 as to an unsafe condition with the user, e.g., high/low heart rate, high/low blood pressure, high/low temperature, malfunctioning machinery, and the like. The USS 995 further receives input from the MTS 900 as to an unsafe position or movement of the user. The USS 995 may receive data from and/or transmit data to any other MSS subsystems through the communication bus 750.

Omnidirectional Treadmill

FIGS. 1A, and 2A-2D show the omnidirectional treadmill (ODT) 100, which is a subsystem of the invention. The omnidirectional treadmill 100 is shown in FIG. 1A in use with a gravity modification system (GMS) 200, which is detailed below.

The user 50, for example, in a harness 242 of a harness unit 240 of a human interface assembly (HIA) 230 associated with the GMS 200, performs locomotion, e.g., walks, runs, jogs, jumps, skips, bends, crouches, kneels, and perform numerous other positions or actions in an uninhibited manner, on the base 101. The surface 102 shape and/or texture, and resulting friction may be related to the simulation being undertaken, or in accordance with objectives set forth by the operator.

Imaging apparatus 401, such as cameras, for example, mounted on supports at along the base 101 (and in communication with the base 101), form part of the motion tracking system (MTS) 900 detailed below. Also the user 50, may wear a headset 402, which forms part of a visual stimulation system (VSS) 920, detailed below, and headphones 411, which form part of an Auditory stimulation system (AUSS) 930, detailed below. The user 50 also may wear gloves 205, which form part of a Tactile Stimulation System (TSS) 950, detailed below.

The ODT 100 includes a base 101 upon which the user may walk in all directions (360 degrees) with the user's 50 motion uninhibited. The base 101 includes a surface 102, on which the user 50 contacts the base 101, with an underlying support 104. A sidewall 103 forms the perimeter of the surface 102 of the base 101. The surface 102 of the ODT 100 is, for example, either active or passive. The shape and/or texture of the surface 102, is changeable, and, for example, can be done dynamically (on the fly), as shown in FIGS. 4A and 4B as detailed below. Embodiments of active, passive, and dynamic surfaces 102 are described below. The surface 102 can also move by rotation and the like, for example, by motors 113 (FIG. 14A), which may be linked to the system computer 470. This is further described below.

A user 50, as shown in FIG. 1A, interfaces with the ODT 100 as his feet contact the passive surface 102 of the ODT 100. This passive interface makes use of kinetic friction, providing predefined static and kinetic coefficients of friction, allowing the user's feet to slide across the surface 102 using kinetic friction. The predefined coefficients of friction may be related to the simulation being undertaken, or it may be related to objectives set forth by the operator. The desired friction at the interface may be achieved by controlling the material properties of the surface 102, or of the user's footwear, for example, through the introduction of low friction coatings or lubricants such as Teflon®, PTFE, Wax and the like.

Alternatively, a passive surface may use rolling friction to allow the user's feet to roll across the surface 102. This may be achieved, for example, by introducing wheels, rollers, or other similar components into the user's footwear and/or the surface 102.

Figure 2A:
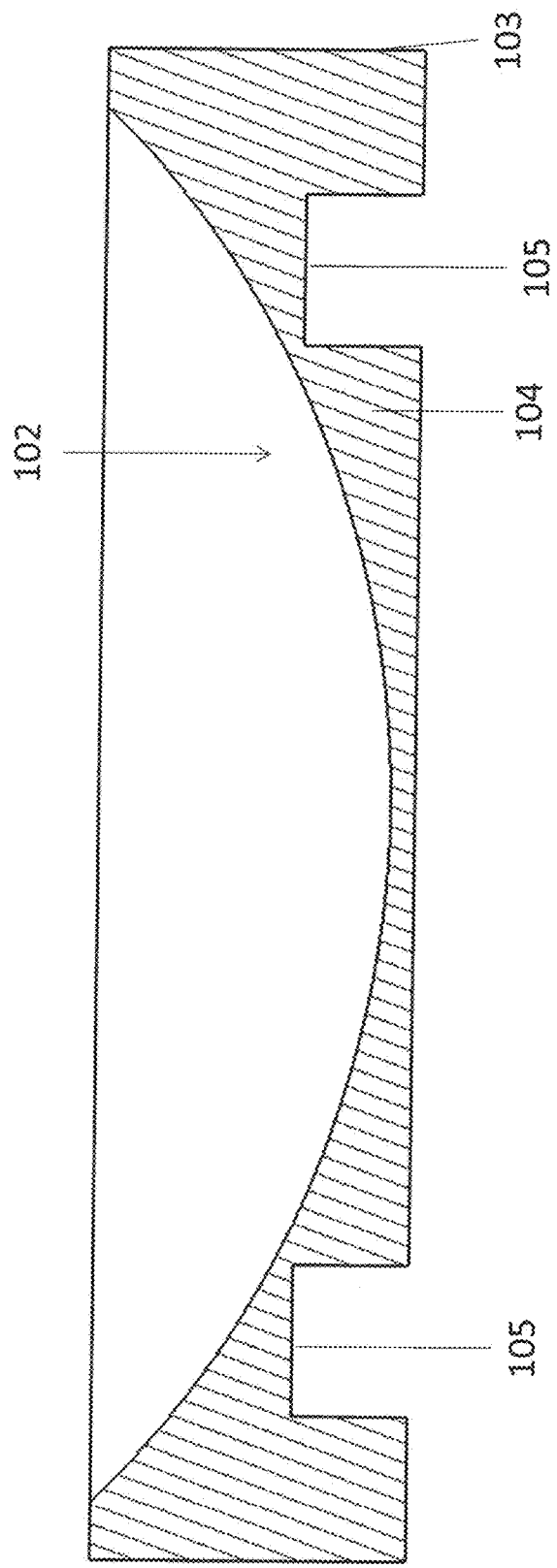
FIGS. 2A and 2B are cross-sectional views of embodiments of the omnidirectional treadmill of FIG. 1A.

The ODT 100, as shown in FIG. 2A, for example, has a concave surface 102. However, the surface 102, may also be, for example, a flat, or convex, or any combination of concave, convex and/or flat. The surface 102, is constructed of materials, including, for example, metals, plastics, Plexiglas, carbon fiber, fiberglass, Styrofoam, wood, rubber, polymers, fabrics, Kevlar, Shape Memory Alloy (SMA), Electro Active Polymer (EAP). The surface 102 rests upon a support 104 of the base 101. The support 104 is such that forces from the surface 102 are transferred through the surface 102 to the underlying floor, or other surface, upon which the base 101 rests. The support's 104 shape and design are determined by the shape and material of the surface 102.

In FIG. 2A, the support structure 104 is of a material whose upper surface is shaped similar to the overlying surface 102. This configuration is such that the surface 102 is supported by the support structure 104, providing even distribution and transfer of forces from the surface 102 to the support structure 104. For example, the support structure 104 is of a foam material, and may be, for example Styrofoam. This material provides lightweight but stiff properties. The support structure 104 includes cut-out portions or cut-outs 105, which extend through the support structure 104, to receive the legs 202 of the GMS 200.

Figure 2B:
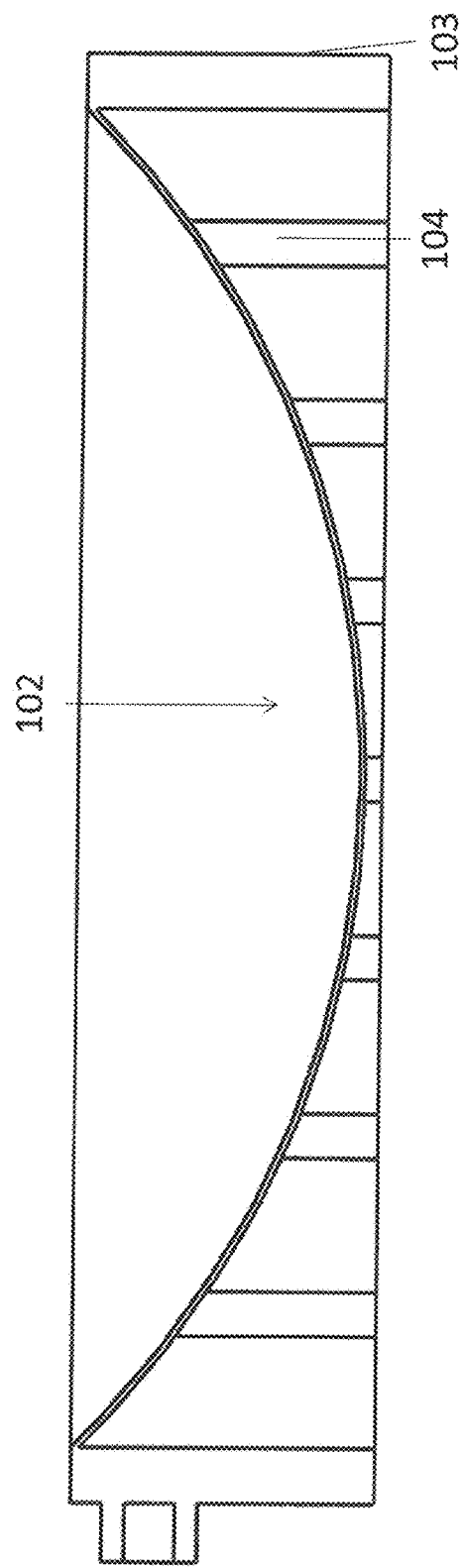

As shown in FIG. 2B, the support structure 104 is of honeycomb structure. This honeycomb shaped support structure 104 provides a highly stiff and lightweight structure.

The surface 102 may be fixed to the base 101, using for example, mechanical fasteners, adhesives, magnets, or any other means of restricting movement between the surface 102 and the underlying base 101.

The components of the ODT 100 may be modular in nature. For example, a foam support structure 104 may be divided into two or more pieces, which are assembled prior to use.

While the base 101 is shown as circular, it may be in other shapes, such as oval, rectangular, triangular and the like, and combinations thereof.

FIGS. 3A and 3B detail the ODT 100 including sensors 122. The sensors 122 are integrated into the ODT 100 in order to provide data, for example, to the Motion Tracking System (MTS) 900 and Data Analytics System (DAS) 910, or any other MSS systems. These sensors 122 include, for example, pressure plates, magnetic sensors, load cells, resistors, thermocouples, tactile sensors, photo sensors, light sensors, proximity sensors, limit switches, cameras, laser scanners, laser trackers, and all other sensors or instruments that may provide data to the any MSS subsystem. The data from the sensors 122 is, for example, stored within the ODT 100, or may be transferred to one or more processing units 811, 991 within the ODT 100, GMS 200, or other part of the MSS 75.

The ODT 100 may also have a dynamic surface, which may change its shape. Such a surface may be used, for example, to enable safe ingress and egress from the ODT 100, without requiring the user to take a large step into the ODT 100; an otherwise concave, convex, irregular, or a combination thereof, slippery surface, increasing safety, and safely accessible for disabled users. In one embodiment, the surface may be flat or nearly so, and very low to the underlying ground. A user would then safely position himself at or near the center of the surface. The surface may subsequently be actuated to change shape such that it assumes its desired shape, allowing the user to begin using the ODT as described above.

In one embodiment, the surface 102 itself may be the actuator and apply the necessary force, as in the case of Shape-Memory Alloys. Here, the surface 102 changes its shape from curved (FIG. 3A) to flat (FIG. 3B), or vice versa, in response to a voltage application, from a voltage source 123. Both the sensors 122 and voltage source 123 are controlled by the system computer 470. In another embodiment, a current source may be used (not shown). A dynamic surface may also simulate changes in slope by tilting the surface (either in its entirety or partially) using similar actuators.

FIGS. 4A and 4B show the ODT 100 with an adjustable surface 102, which, for example, is dynamically adjustable "on the fly," and for example, in real time. Within the base 101 are actuators 114 or other lift and/or retraction members 114, placed at various locations beneath the surface 102, to raise and depress the surface, resulting in changes, e.g., elevations, in the surface 102. The actuators 114 are under the control of a controller 810 of the system computer 470. Alternatively, the actuators may be manually operated.

The resultant dynamic surface simulates changes in terrain as the user advances through the simulated environment. This is achieved through the application of force to a semi- or variably-rigid surface. Example actuators 114 include, servos, motors, hydraulic or pneumatic actuators.

These actuators 114, for example, change the texture of the overlying surface dynamically upon receiving such data from the Controller 810 of the system computer 470 (described below).

Figure 5:
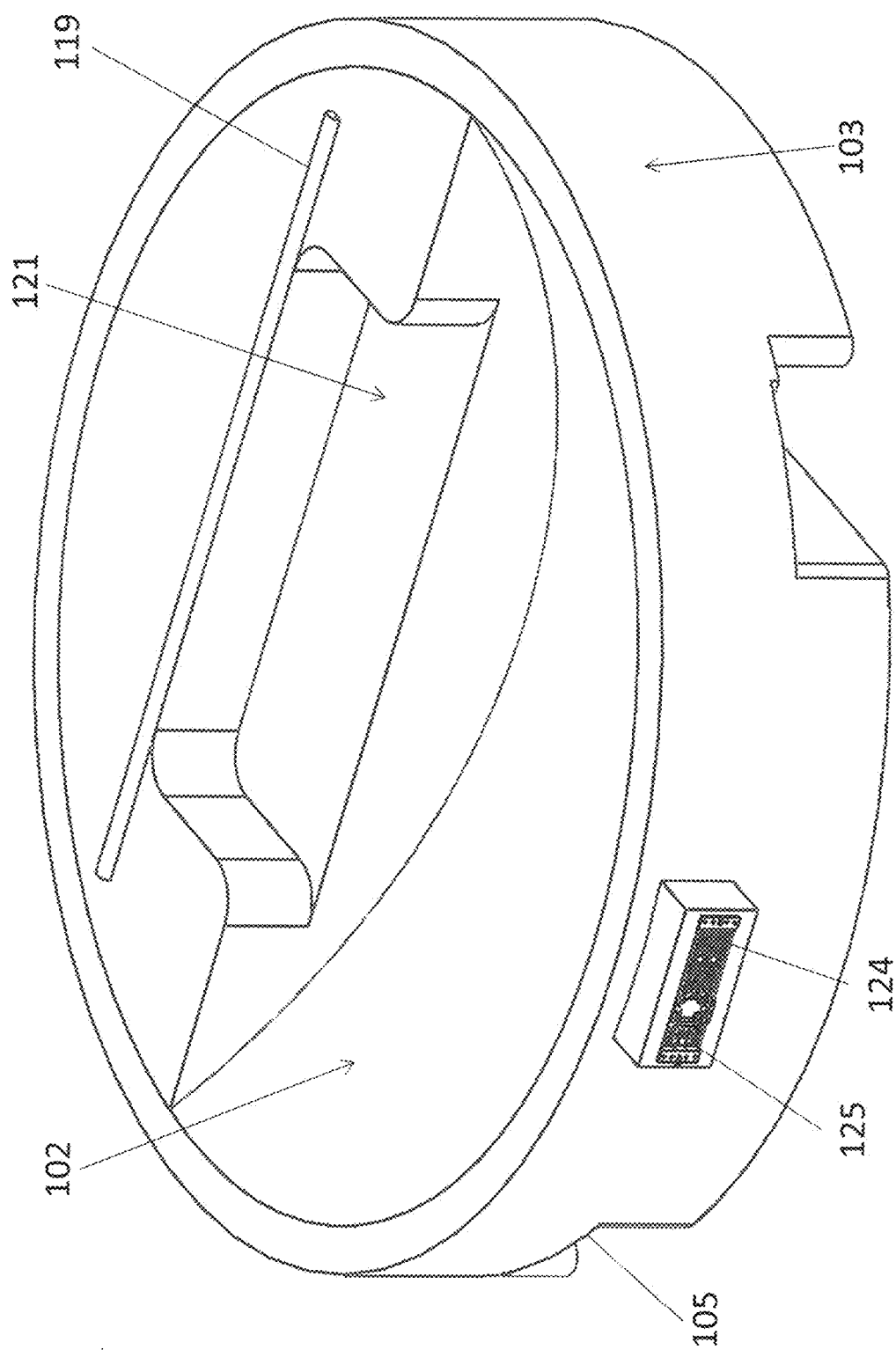
FIG. 5 is a perspective view of another embodiment of the omnidirectional treadmill of FIG. 1A.

FIG. 5 shows the ODT 100 with a rigid interface or locking mechanism 124, which connects the GMS 200 to the ODT 100. The locking mechanism is, for example, one or more of (electro)magnet(s), hook(s), clip(s), vice(s), clamp(s), screw(s), ratchet(s), strap(s), belt(s). The ODT 100 typically also includes an electrical and/or electronic interface 125 with the GMS 200, such that when the GMS 200 is physically interfaced with the ODT 100, the electrical and/or electronic interfaces are also engaged, and data may be transferred uni- or multi-directionally between the ODT 100, GMS 200, and other MSS subsystems wired or wirelessly through a communication bus. The ODT 100 may be driven by the GMS 100, MTS 900, Controller 810, GES 990, MSS operator, or any other MSS subsystem.

Figure 6:
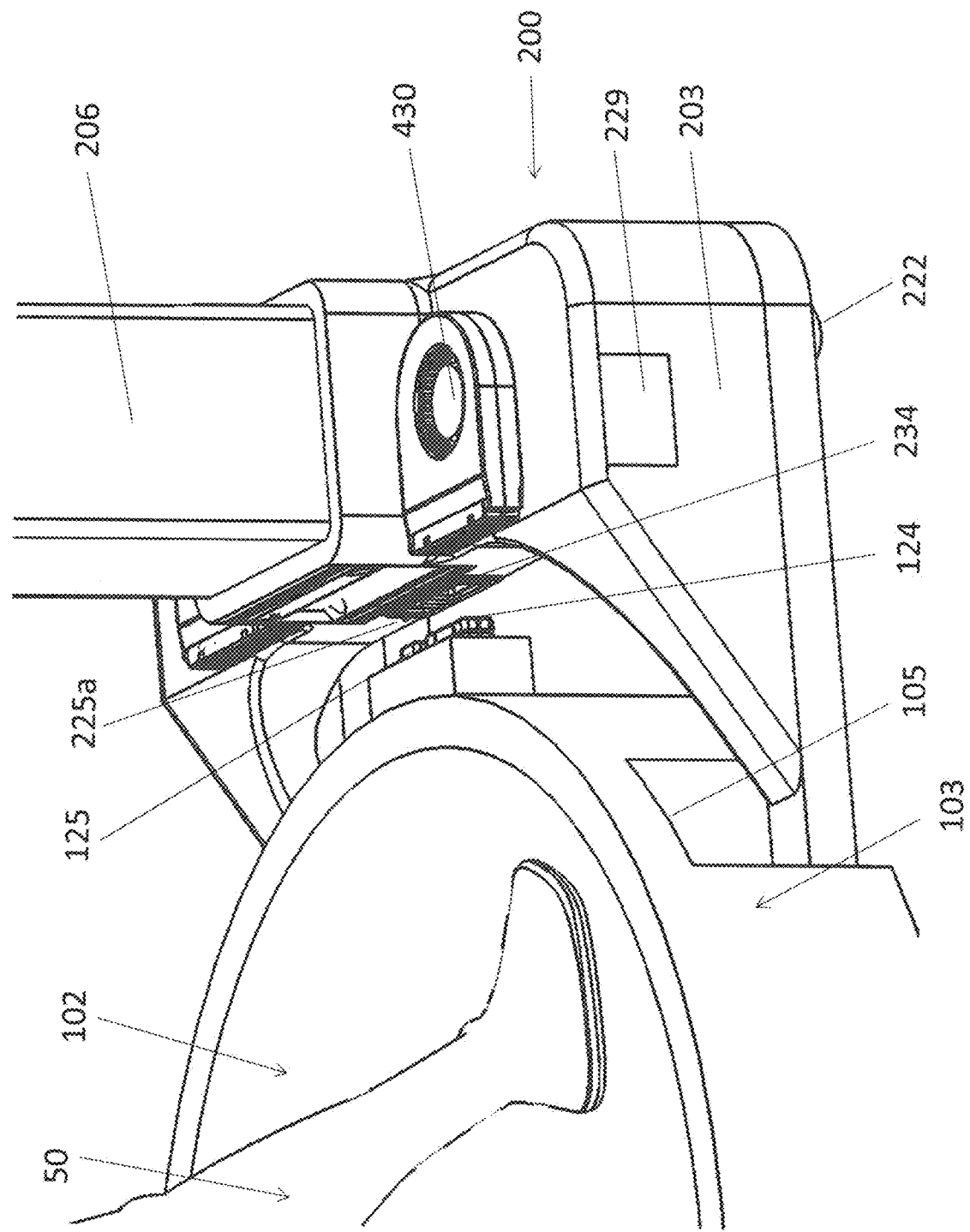
FIG. 6 is a perspective view of the apparatus of FIG. 1A showing the components for mechanical, electrical and/or data connections.

FIG. 6 shows the connection of the locking mechanism 124 of the ODT 100 to a correspondingly configured receiver 234 of the GMS 200; and the electrical and/or electronic interfaces 125 and 225a, of the ODT and GMS, respectively. The GMS is described in detail below.

Figure 13A:
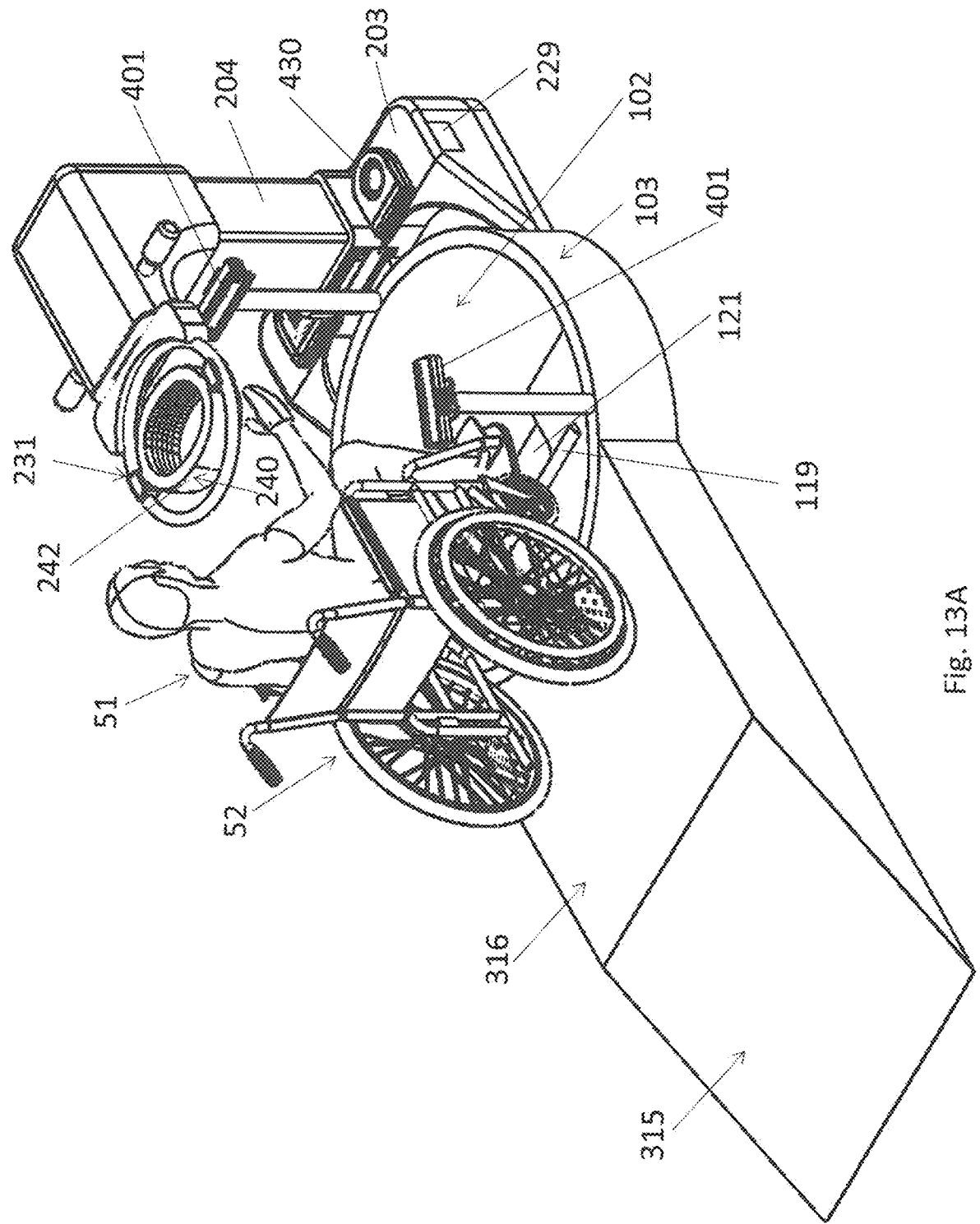
FIGS. 13A-13D are perspective views detailing access and use of the apparatus of FIG. 1A by a wheelchair user.

FIGS. 13A-13D and 5 show the ODT 100 for use by a disabled user 51. In FIG. 13A, the ODT 100 is accessed by a ramp 315 and a platform 316, or steps (not shown). On the platform 316, the wheelchair 52, may safely come to rest prior to the user entering the ODT 100. The ramp 315 and platform 316 may be bounded by one or more rails (not shown) for safety. There may also be a stop member 119, on the ODT 100, platform 316, and/or ramp 315, to prevent the wheelchair from rolling onto the ODT 100. An ODT ramp (not shown) or one or more steps 121 (FIG. 5) may lead the user towards the center of the ODT 100, allowing for safe ingress and egress. The ramp (not shown) and/or steps 121 may retractable, removable, or movable, such that once the user is in place in the ODT 100, they may be positioned such that they do not interfere with the prescribed use of the ODT 100.

Alternatively, a disabled user 51 may access the ODT whereby a portion of the ODT 100 surface 102 is removable, retractable, or movable, allowing the user to step on the underlying floor until the user 51 is close to the center of the ODT 100, and subsequently takes a small step into the center of the ODT 100. The complementary portion of the ODT 100 is then replaced to complete the surface 102 of the ODT 100.

Figure 13B:
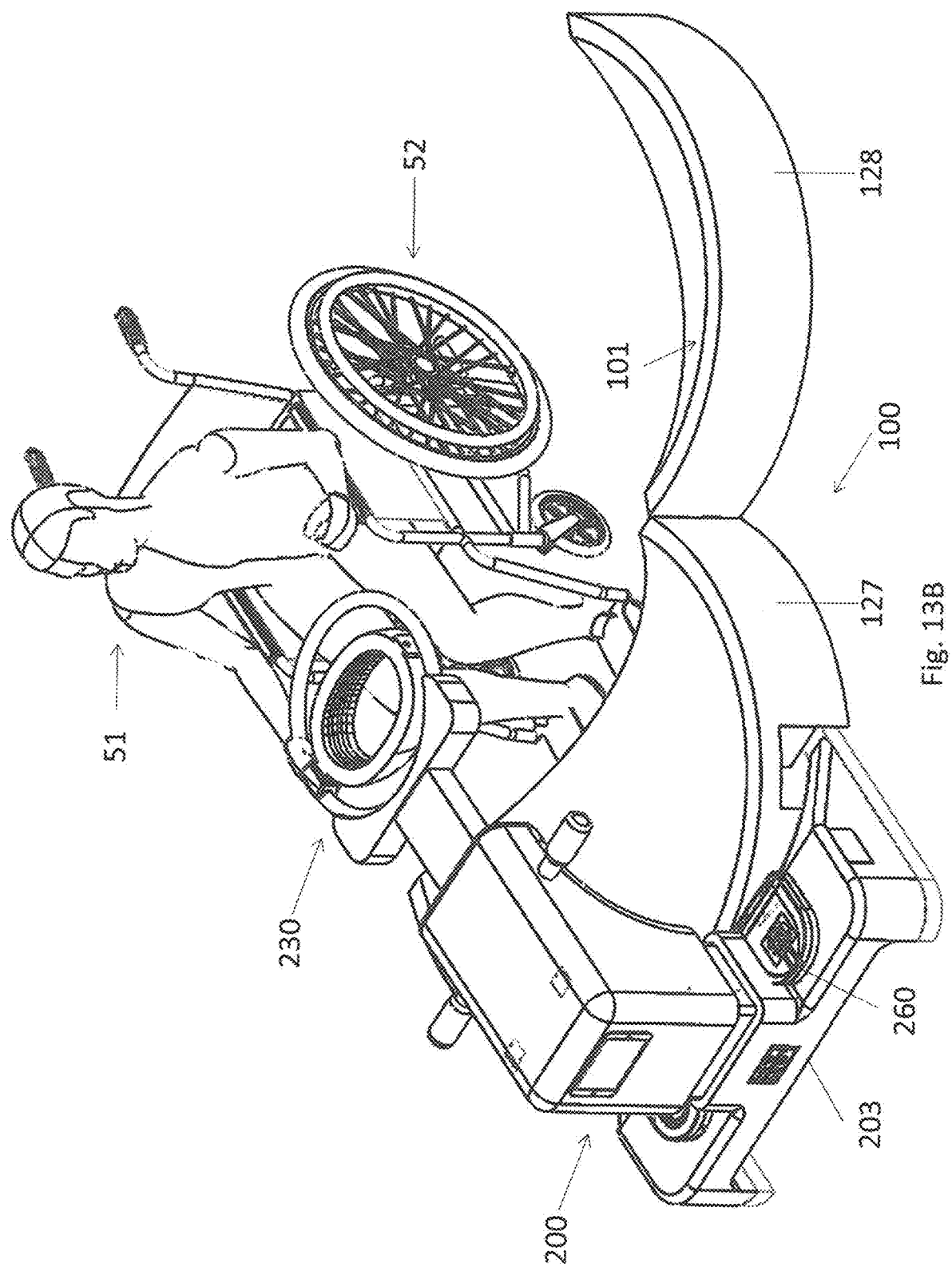
Figure 13C:
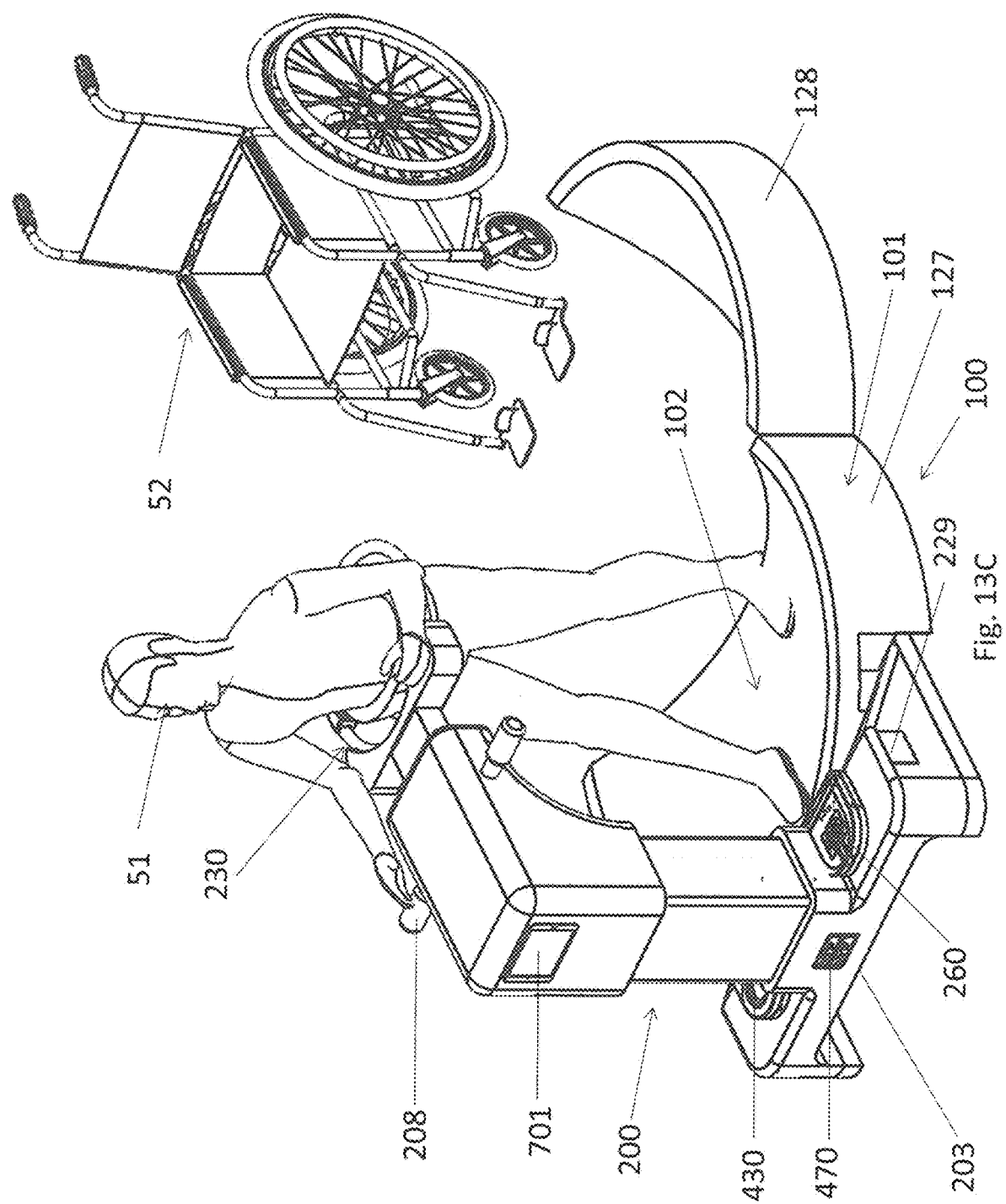

In FIG. 13B, a wheelchair user 51 approaches the ODT 100 from along a surface, such as a floor. The base 101 opens as into section 127, 128 to accommodate the wheelchair 52 and position the user 51 for pickup by the HIA 230. FIG. 13C shows the user 51 now in the HIA 230, with the wheelchair 52 out of the range of the base sections 127, 128.

Figure 13D:
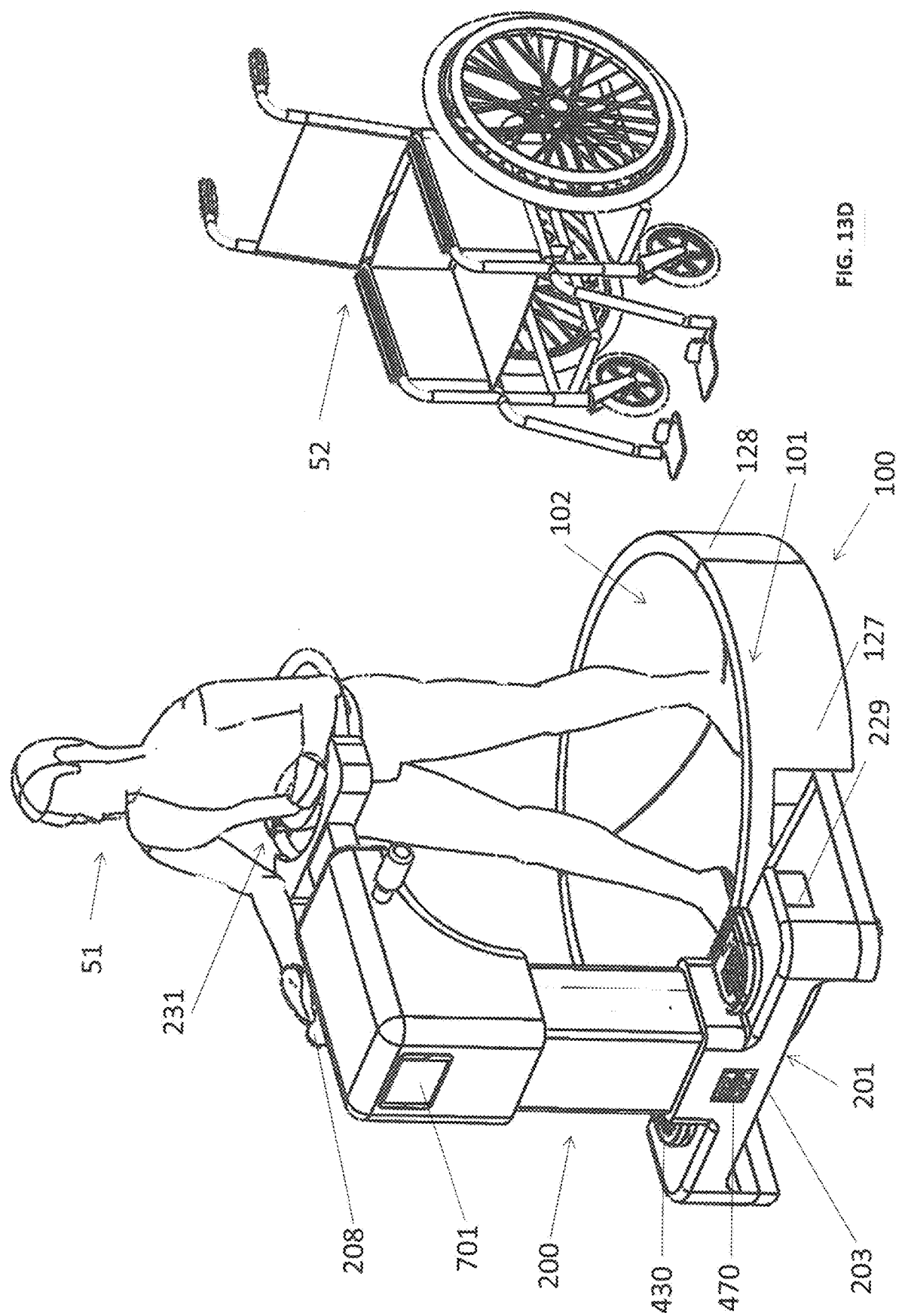

In FIG. 13D, the base 101 of the ODT 100 has its sections 127, 128 rejoined, such that the user may performs various actions, as described previously.

An alternative to the passive and dynamic surfaces described previously is an active surface. In order to facilitate walking and other actions performed by the user, an active surface 102 may provide a fixed contact between the user's foot or footwear and the surface 102. This is achieved, for example, by ensuring that the static friction between the user's feet or footwear is high enough such that the user's foot cannot slide along the surface. Static friction is achieved, for example, in ways including the use of a powered belt (similar to traditional treadmills), as shown in FIG. 14A. In this embodiment, the surface is moved at a similar speed to the user's foot (as with a traditional treadmill), such that the contact between the user's feet and the surface remains static and unbroken during each step. The movement of the surface requires one or more actuators, as in a traditional treadmill.

In one embodiment, omni directionality is achieved by using a traditional linear treadmill belt 111 (FIG. 14A) and providing it with a degree of freedom in the yaw axis. This may be achieved by housing the treadmill belt on a structure 112, which may be moved by an actuator 113, for example, a motor. In one embodiment, the treadmill belt would be moved in yaw to match the user's direction of travel, as identified by the Motion Tracking System 900 described herein.

Figure 7:
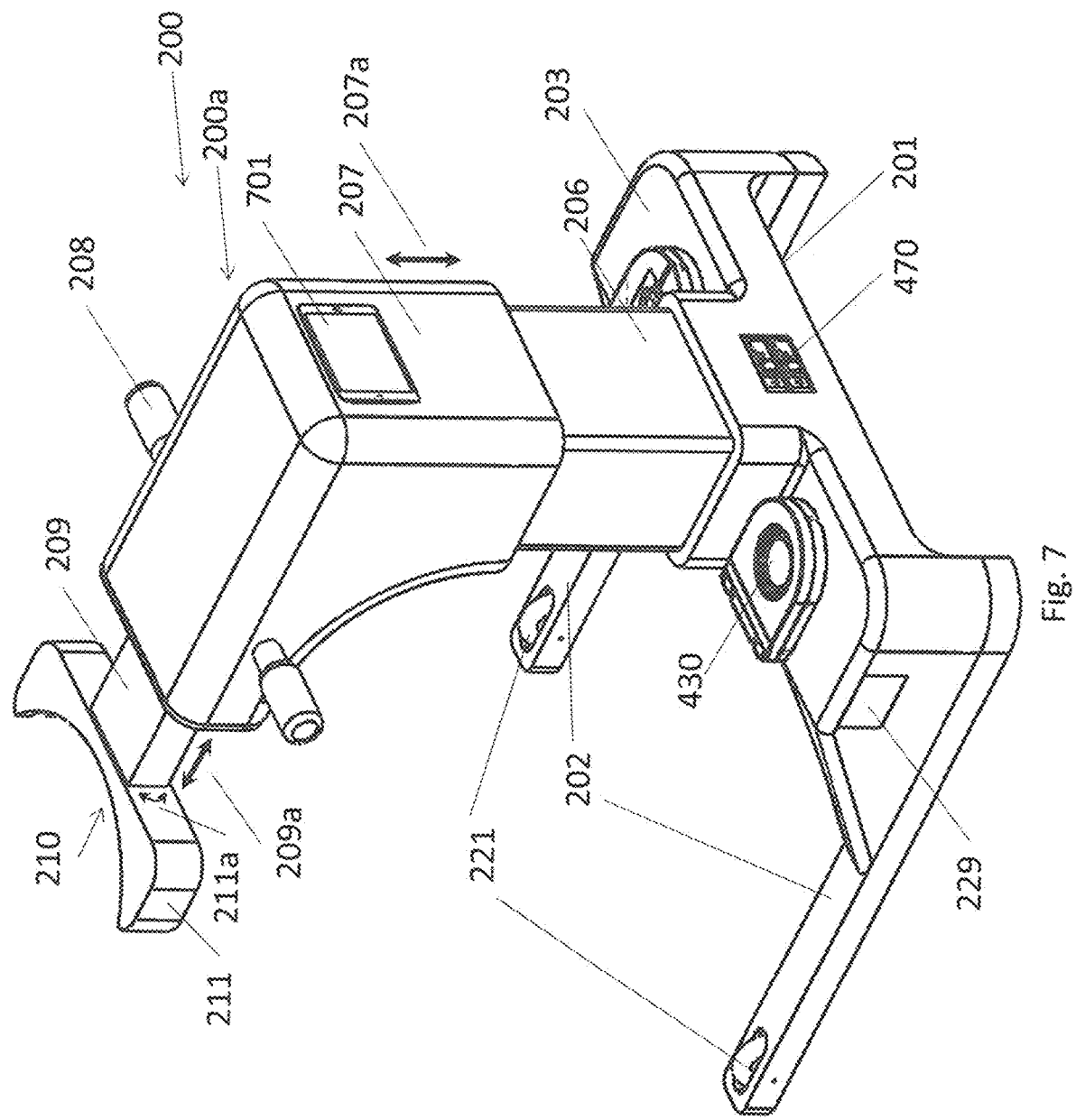
FIG. 7 is a perspective view of a gravity modification system (GMS) in accordance with embodiments of the invention.
Figure 8:
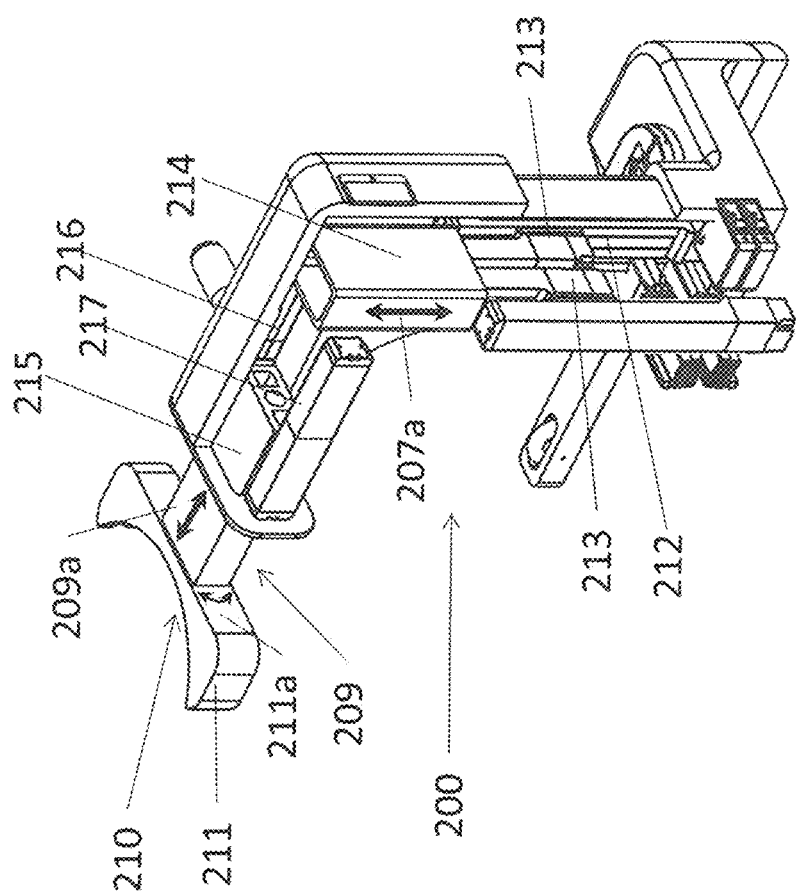
FIG. 8 is a cut-away view of the GMS of FIG. 7.

Gravity Modification System (GMS) Continuing with FIGS. 1A and 1B, and turning also to FIGS. 7 and 8, there is shown the gravity modification system (GMS) 200. The GMS 200, as a force applying unit 200a, is a subsystem which applies a positive (upward) or negative (downward) force (e.g., represented, for example, by double headed arrow 207a) on the user (in a harness 242 or other receiving device), parallel or substantially parallel to a gravity vector, thereby increasing or decreasing the weight being home by the user 50. The GMS 200, for example, may be driven by the ODT 100, MTS 900, Controller 810, GES 990, MSS operator, or by any other MSS subsystem. The simulated gravity may be related to the simulation being undertaken, or it may be related to objectives set forth by the operator.

GMS Structure

The GMS 200 enables the user to move naturally while increased or decreased gravity on the user is simulated. The GMS 200 is such that it does not restrict natural gait.

Figure 15:
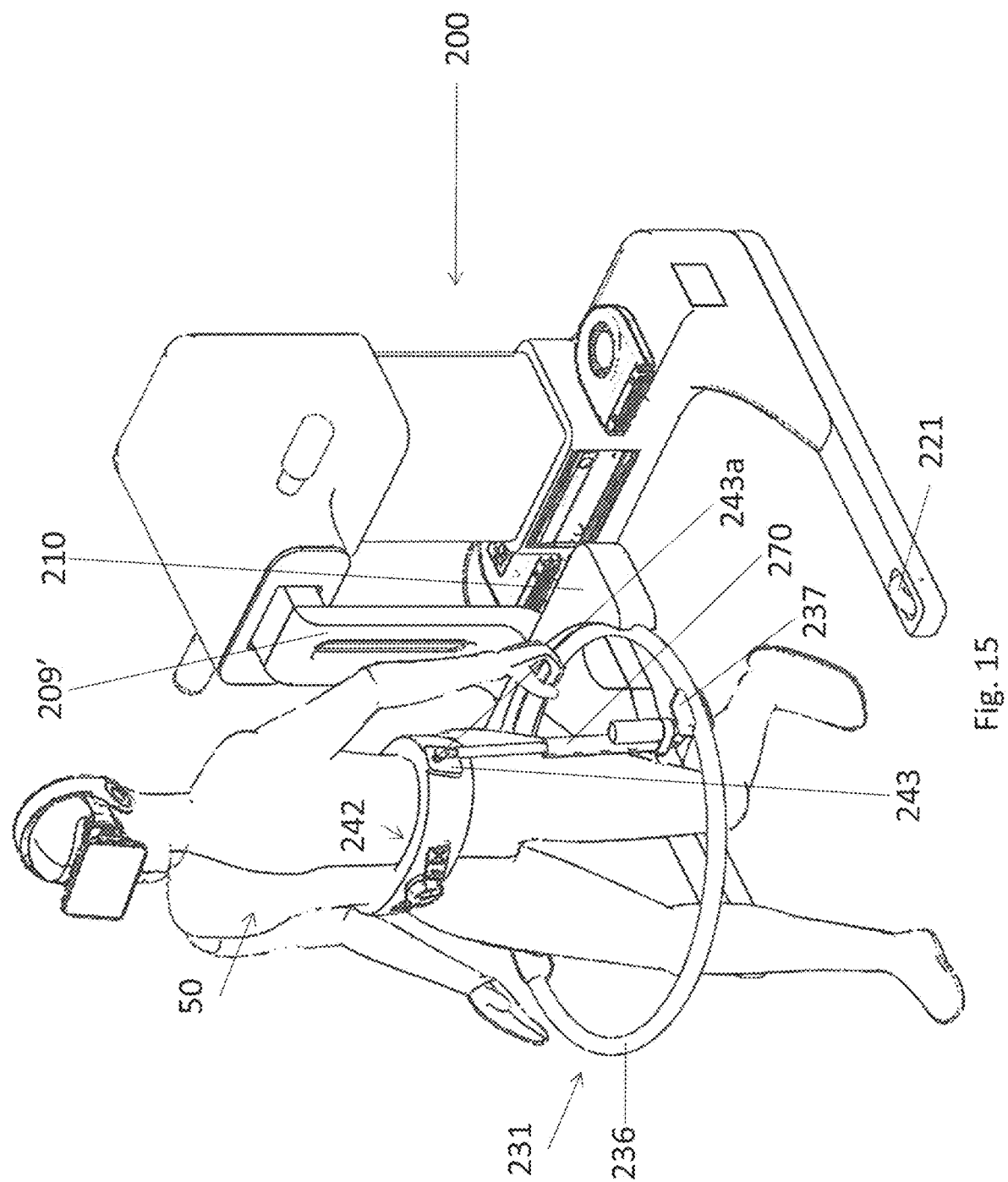
FIG. 15 is a perspective view showing a user operating the apparatus of FIG. 14B-2.
Figure 18:
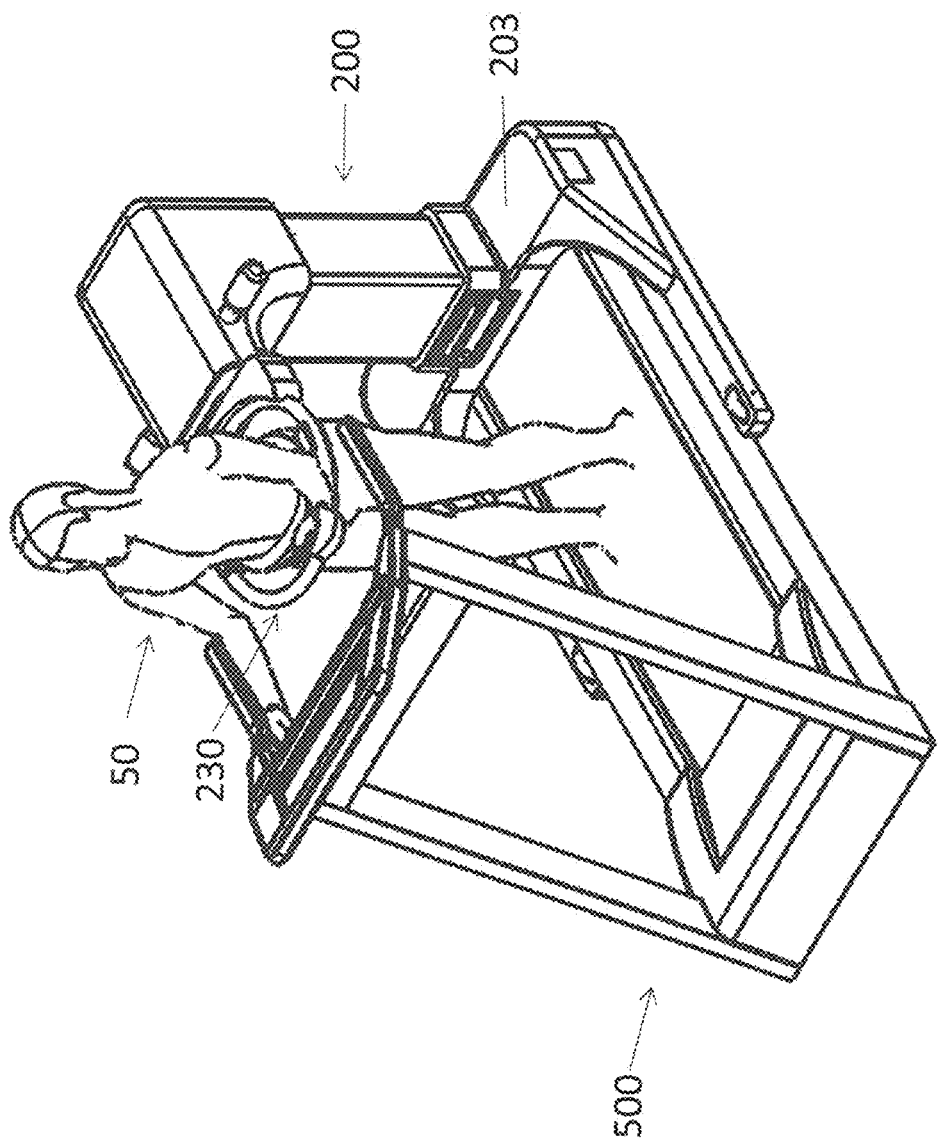
FIG. 18 is a perspective view showing the GMS in use with a conventional treadmill.

The GMS 200 includes a base 201, with oppositely disposed legs 202 connected by a crossbar support 203 of the base 201. The legs 202 and crossbar support 203 support and stabilize the GMS 200 on a surface, such as a floor. The crossbar support 203 may be elevated in order to accommodate objects beneath it, for example, a treadmill. The legs 202 are spaced apart from each other, such that the area between the legs 202 is of a size and dimensions to accommodate a human user using the GMS 200, for example, as shown in FIG. 15, or the ODT 100 occupying the area, as shown, for example in FIG. 1A, and may, for example, be far enough apart to accommodate for other equipment, such as a treadmill, between them, as shown in FIG. 18. The legs 202 are designed to fit into cutouts 105 in the base 101 of the ODT 100.

A vertical support 206 is mounted on the crossbar support 203. A vertically movable (retractable/extendable) arm support 207 is movably mounted on vertical support 206. The vertical movement of the arm support 207 (as shown by the double headed arrow 207a) is controlled by actuators, which apply the desired force on the arm support 207. Such actuators include for example, motors (not shown), and for example, screw members 212, which rotate to move elevators 213, which connect to a block 214, that moves the arm support 207 vertically. The actuators (not shown) are, for example, under the control of the system computer 470.

Further examples of force application and transmission methods to the arm support 207 include but are not limited to: electric motor(s), torque motor(s), servo motor(s), stepper motor(s), linear motors, hydraulic actuators, pneumatic actuators, electromagnetic actuators, rack and pinion, ball screw(s), belt(s), cable(s), pulley(s), gearbox(es), and the like.

An arm support 207 connects to the vertical support 206 at its upper end. Handles 208 attach to the arm support member 207. An arm 209, moveable into and out from the arm support 207, for example, horizontally (as shown by the double headed arrow 209a), is movably mounted in the arm support 207. The arm 209 is moved, in and out of the arm support 207, by an actuator (not shown), which is, for example, under the control of system computer 470. The arm 209, at its distal end, attaches to an adapter 210, which in turn connects with a Human Interface Assembly (HIA) 230. The adapter 210 is rotatable (double headed arrow 211a) about the arm 209.

Figure 9:
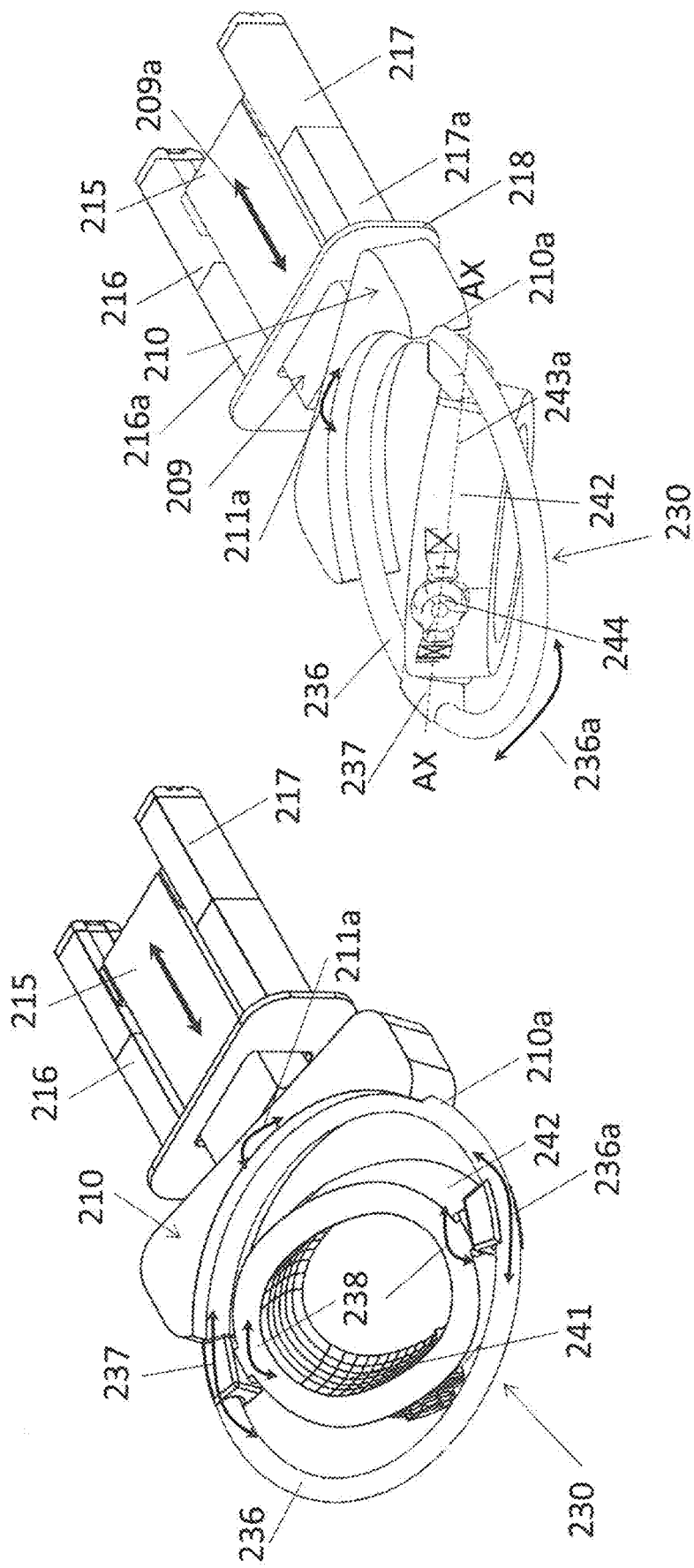
FIGS. 9A, 9B, 10A are perspective views of a harness system and its connection to a portion of the GMS, in accordance with embodiments of the invention.
Figure 10:
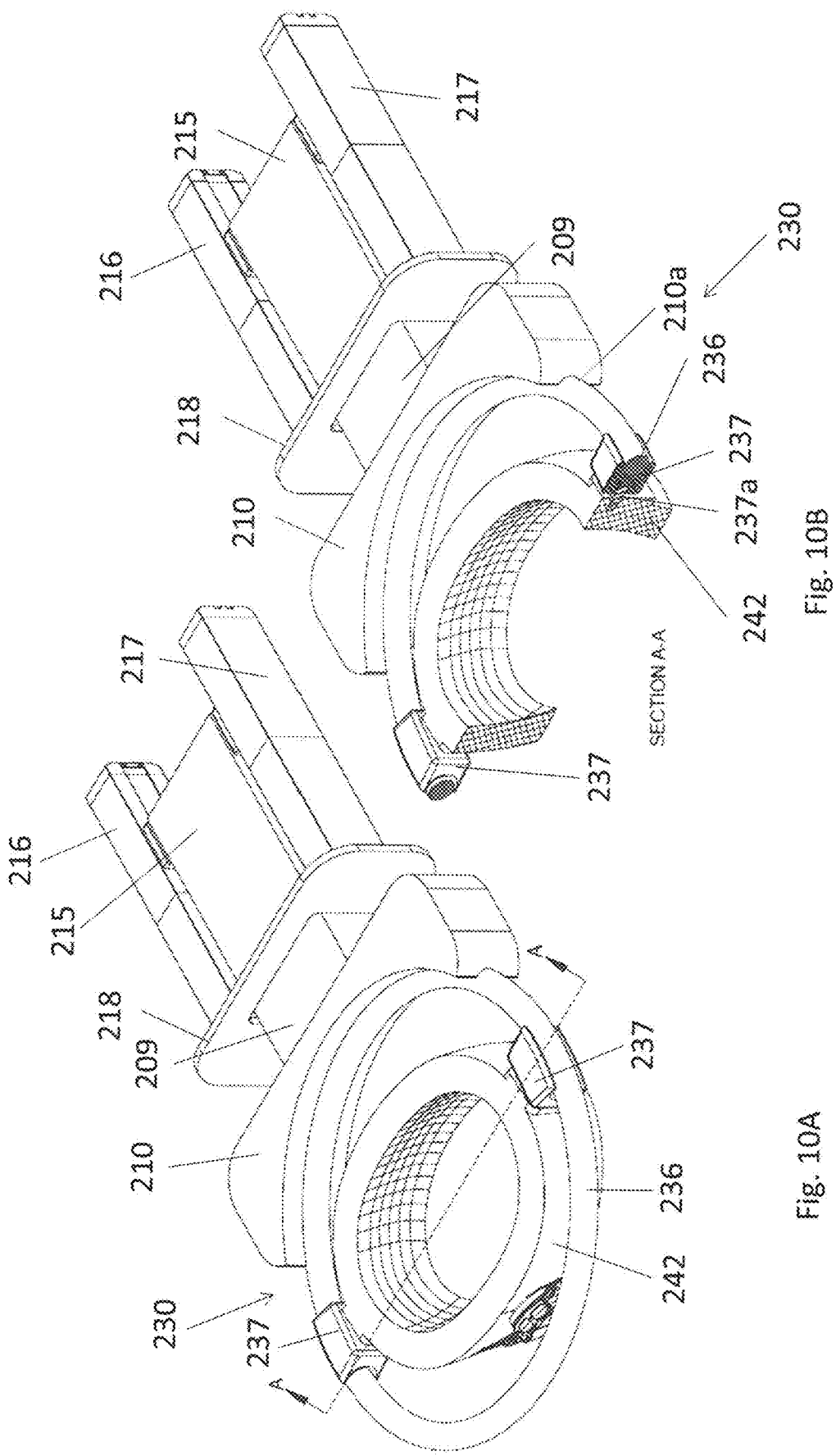
FIG. 10B is a cross-sectional view taken along line A-A of FIG. 10A.

Turning now to FIGS. 9A and 9B, the arm 209 connects to a pushing member 215, which is driven by actuators, for example, motors 216 and 217. The columns 216a and 217a which support the screws or drive shaft (not shown) of the motors end in a column plate 218. The column plate 218 serves as an inward limit of travel for the arm 209. The motors 216 and 217 are, for example, under the control of the system computer 470.

The base 201, the legs 202 and crossbar 203, for example, includes wheels 221, 222, rollers or the like. This allows for mobility and portability of the GMS 200.

There is also a battery 229, which provides power to all of the electrical components of the GMS 200. There is also a speaker 260, which is part of the AUSS 930.

There is also a port 430, which functions, for example, as an emitter, through which various scents, substances and the like can be emitted into the surrounding environment. Furthermore, this port/emitter 430 is part of the olfactory stimulation system OSS 980 as described further below. The port/emitter 430 is part of the atmospheric stimulation system 960, as described below.

There is an emergency shut off button 601, for example, at the arm support 207, which is part of the USS. There are cameras and sensors 225a, 225b on the GMS 200, which are linked to the system computer 470. These cameras and sensors 225a, 225b are used for tracking the user's motion and physiological parameters, and provide data, for example, to the MTS 900 and UMS 987, respectively. One or more sensor(s) 226 may be included on the GMS structure, for example, in the arm support 207. These sensors are used, for example to measure motion or position. Such a sensor is, for example, an IMU (Internal Measurement Unit), an accelerometer, a gyroscope, a magnetometer, or the like. This sensor 226 is linked to the system computer 470 shown in FIG. 1B.

FIGS. 9A, 9B, 10A, 10B, 11, 12A and 12B show the HIA 230 and UHS 940. The HIA 230 provides an interface between the user 50 and the GMS 200. The HIA 230 is designed to connect to a harness 242 of a harness unit 240. In one embodiment, the HIA 230 is designed to connect to the harness at two points 243a, located proximate to the user's hips.

The adapter 210 receives a user receiving device, for example, a ring 236 of the HIA 230 in a groove 210a, in a frictional engagement. This frictional engagement may be supplemented with, or replaced by mechanical fasteners, such as screws, bolts, as well as adhesives, welds and the like. An assembly provides rotational motion of the harness 242 within the user receiving device (ring) 236. For example, a slider 237 movably mounts a harness 242 to the ring 236, so as to be rotatable about the ring 236 (the rotation in accordance with the double headed arrow 236a). The slider 237 includes pins 237a, which fit into apertures 237b on the slider 237 and apertures 243a on the receivers 243 of the harness 242. The harness 242 is rotatably mounted between the center of the sliders 237 about the axis AX-AX 243x as per arrow 238 (FIGS. 9A, 9B). The rotational movement of the adapter 210, provides a degree of freedom as per arrow 211a, as well as the rotation of the sliders 237 along the ring 236.

Figure 11:
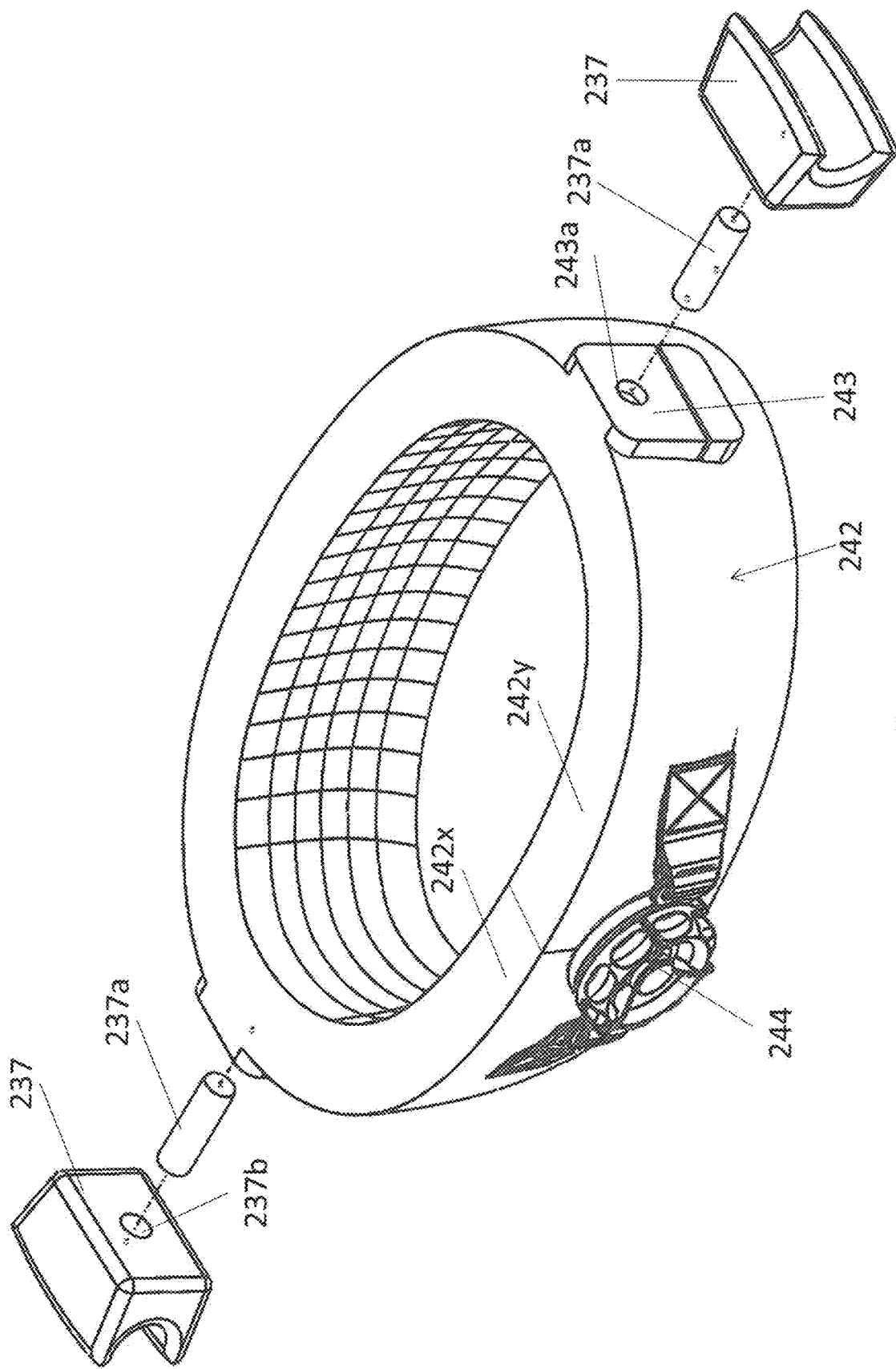
FIG. 11 is an exploded view of a harness unit from the system shown in FIGS. 9A, 9B, 10A and 10B.

The harness 242 may have separable parts that can be rejoined and tightened to fit the user. FIG. 11 shows an example of a harness 242 with two ends 242x and 242y, which are spreadable, allowing for wearing by the user. The ends 242x, 242y can be rejoined and tightened, to fit the user, by the joining mechanism 244.

FIG. 13D also shows a computer 470, which controls, for example, a combination of the ODT 100, GMS 200 and other systems within the MSS, these additional systems detailed herein. The computer 470 is processor/microprocessor based and includes one or more central processing unit (CPU), graphics processing unit (GPU), collectively processing unit (PU), as used herein. The computer 470 links to various networks, such as local and wide area networks, such as the Internet, by various links, including on line links and the like. These links may be facilitated by a communications module 820 or the like. There is also an operator interface 701 for the MSS, from which the GMS 200, ODT 100 and all other systems detailed herein can receive inputs or otherwise be user, administrator or otherwise controlled.

Figures 1, 14B:
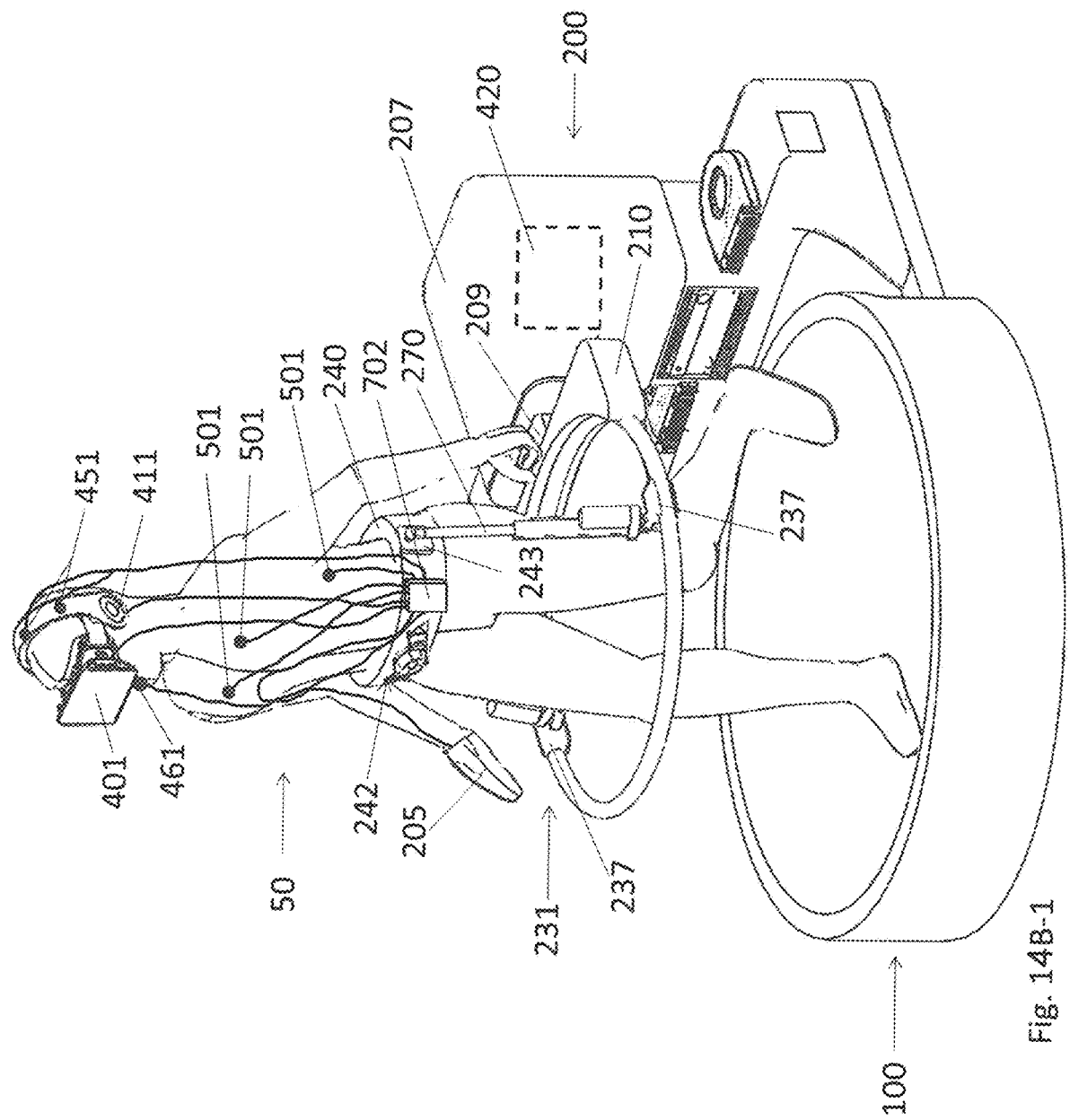

Attention is now directed to FIGS. 14A and 14B-1 which show the GMS 200 used with an alternate HIA 231, with the ring 236 located below fingertips of an extended arm of the user 50. In FIG. 14A, the arm 209 includes an extension 209', allowing the adaptor 210 to receive the ring 236 below the user's fingertips. In FIG. 14B-1, the arm support 207 remains low, such that the ring 236 is below the user's fingertips. This ensures that the user may ambulate normally, without the HIA 230 or any part thereof interfering with arm-swing movements which characterize normal human gait patterns, and are important in the maintenance of balance and natural gait, by reducing the angular momentum and rotational motion of the body. This is important in order to increase the fidelity of simulation for ambulation, in all applications where more accurate gait patterns are beneficial. Furthermore, in this embodiment the user may ambulate normally with natural arm-swing, is provided full 360 degree motion in the yaw axis, and there are no structures or components above the user's midsection.

Additionally, in FIG. 14A, the ODT 100 includes a linear treadmill 111, on which the user is ambulating. In order to provide omnidirectionality, as described above, the linear treadmill is located on a rotatable surface 112, which is rotated by one or more actuators, for example, a motor 113. This rotation is executed, for example in accordance with the user's rotation within the HIA 231, such that the orientation of the treadmill matches the locomotion direction of the user.

Figures 2, 14B:
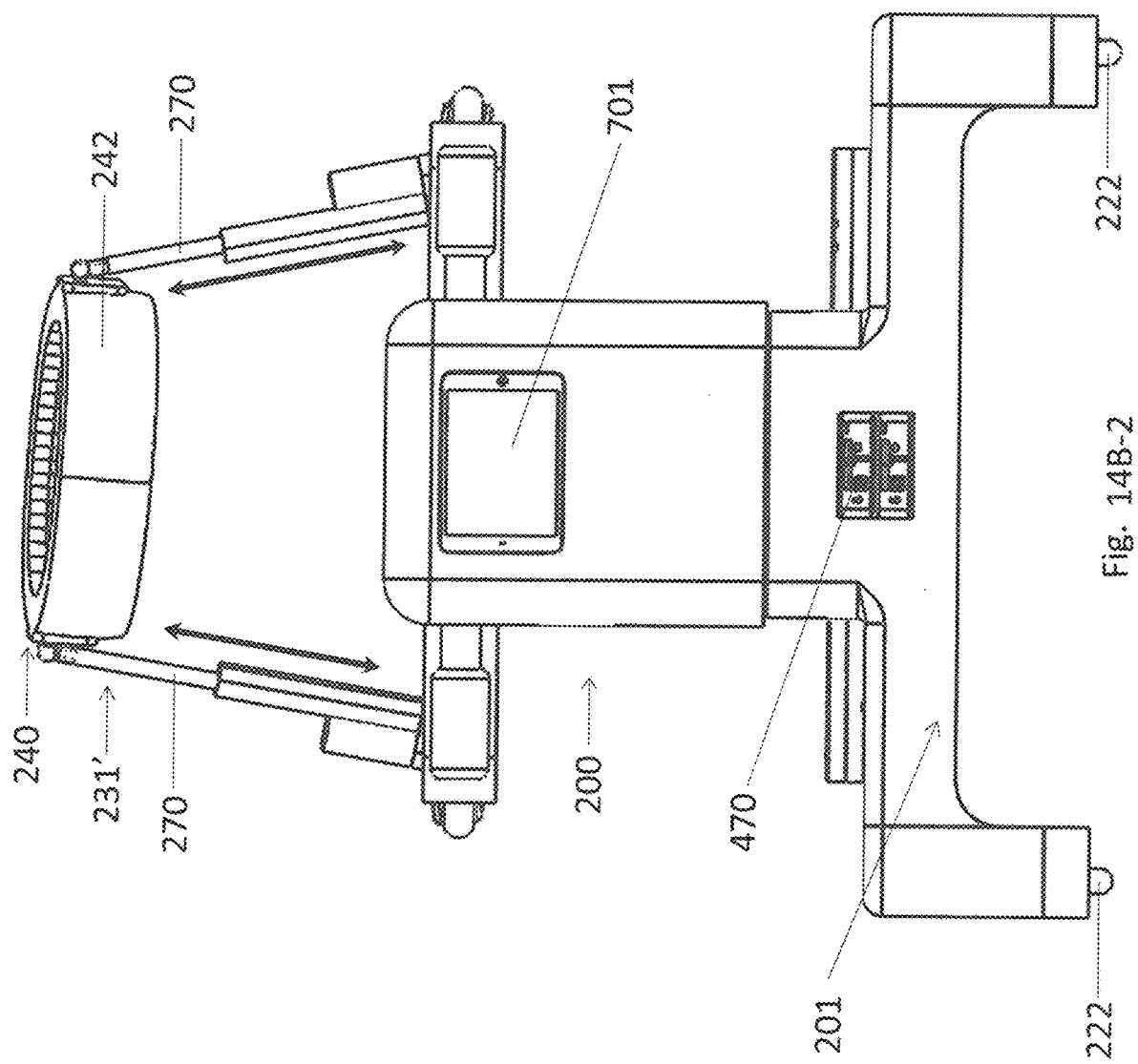

In FIGS. 14A and 14B-1, the HIA 231 includes the harness 242, to which actuators, for example, pistons 270 or similar mechanisms are attached (for example, movably), via the apertures 243a in the receivers 243 of the harness 242, providing the user a degree of freedom in the pitch axis. The opposite ends of the pistons 270 mount to the slider 237, for example, by pivots or hinges, with the sliders 237 movably mounted to the ring 236 as detailed above, allowing for rotation about the ring 236, or yaw. The pistons 270 allow for vertical movement of the user, as well as roll, if the pistons 270 are not compressed or extended symmetrically, in the HIA 231', as shown in FIG. 14B-2. The adapter 210 is rotationally mounted to the arm 209. This allows for motion by the user in at least three degrees of freedom. Additionally, as the ring 236 is lowered to below the fingertips of the user 50, the user 50 has locomotion with uninhibited arm swing.

The actuators 270 may include, for example, tubes, rods, or take on various other shapes, and for example, are made from any of the aforementioned materials, so long as they provide a rigid interface between the harness 240 and the HIA 230. The interface between the HIA 230 and the actuators 270 may, for example, be rigid, or include a joint or hinge allowing the harness support to pivot up and down. This accommodates users with varying hip widths.

As shown in FIG. 14B-1, sensors, such as electrodes 451, 461, 501 are connected by leads (wires) to an interface 702, which links by wired or wireless links to the system computer 470. Electrodes 451, for example, located on the user's head, are part of the neurological stimulation system (NSS) 970, detailed below. Electrode 461 is used to stimulate the tongue for example, as part of the gustatory system stimulation system 985, as detailed below. Electrodes 501 are sensors associated with the user monitoring system (UMS) 987, detailed below. These electrodes 501 are used in measuring physiological parameters, such as heart rate, blood pressure, skin temperature, body temperature, galvanic skin response, and others, as detailed below.

FIG. 15 shows a user 50, using the GMS 200, as shown in FIG. 14B-2 for walking over a substantially flat surface (floor). In this configuration, the GMS can, for example, be moved by the user as the user walks, due to the wheels 221 and 222 (not shown) in the GMS.

Figure 16A:
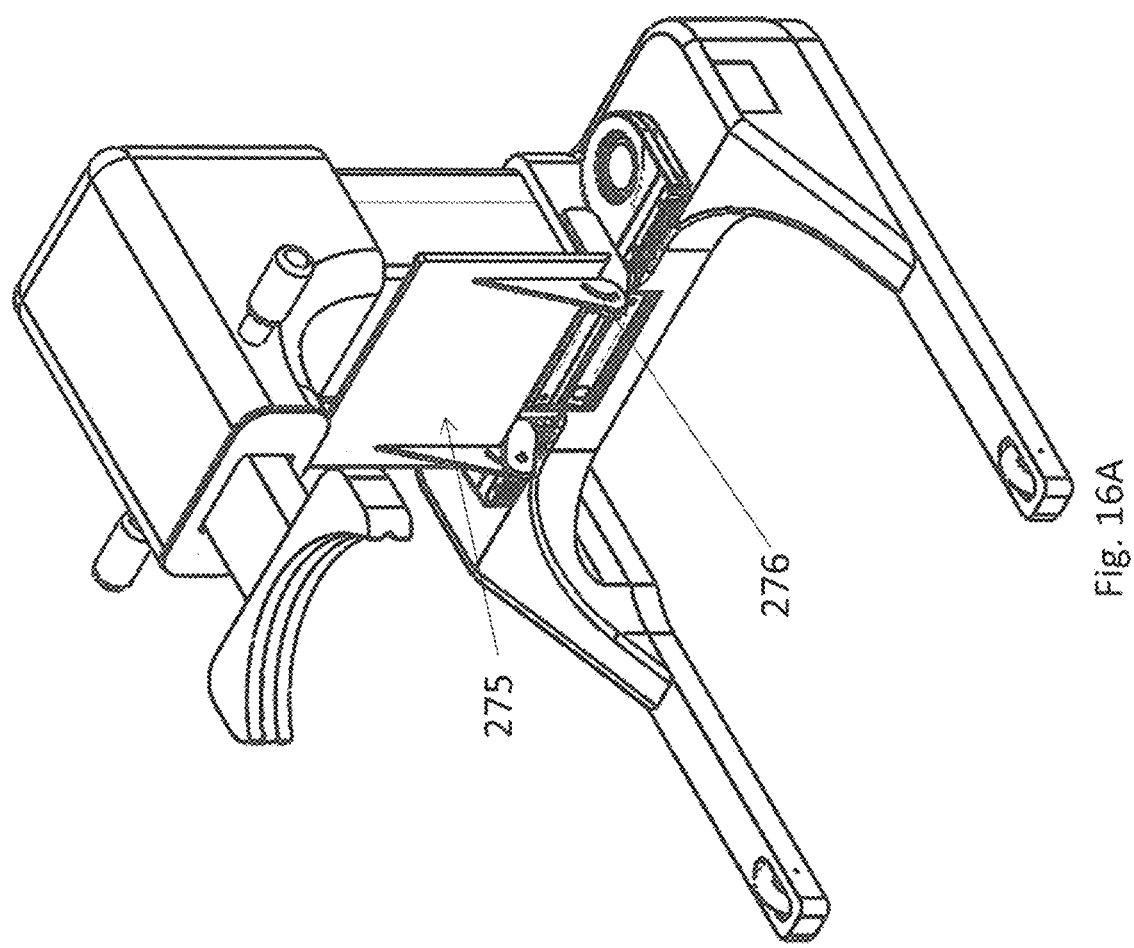

FIGS. 16A-16E show the GMS 200 equipped with a platform 275. The platform 275 is mounted to the GMS, for example using hinges 276, and is moveable from a non-use or storage position, as shown in FIG. 16A, to a use position, as shown in FIG. 16B. The platform may also include one or more steps (not shown). This platform allows for safe and simple transportation of a user, and also ingress and egress into and from to the ODT 100 without the use of ramps, stairs, or other similar devices, as described previously.

Figure 16C:
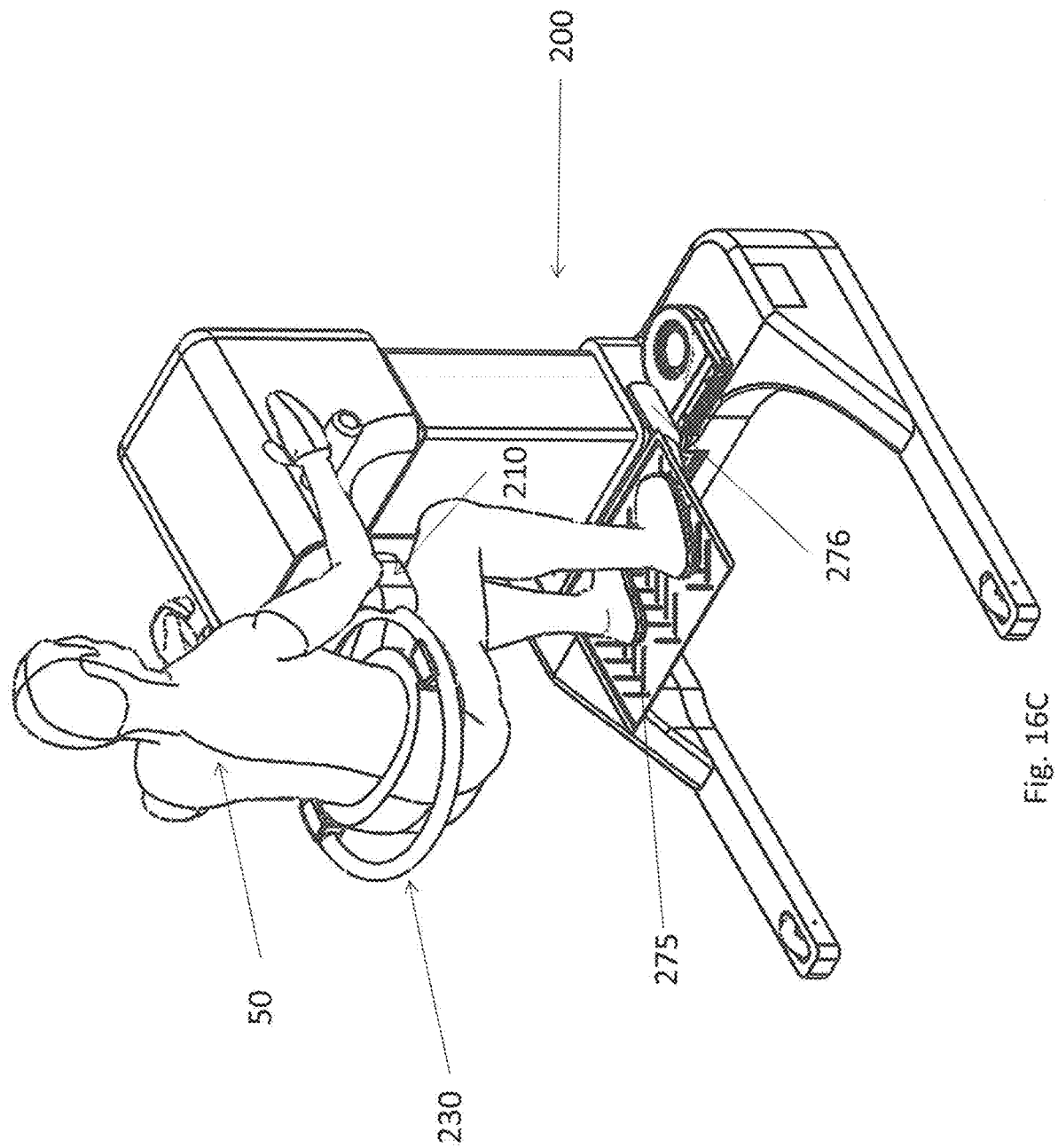
Figure 16E:
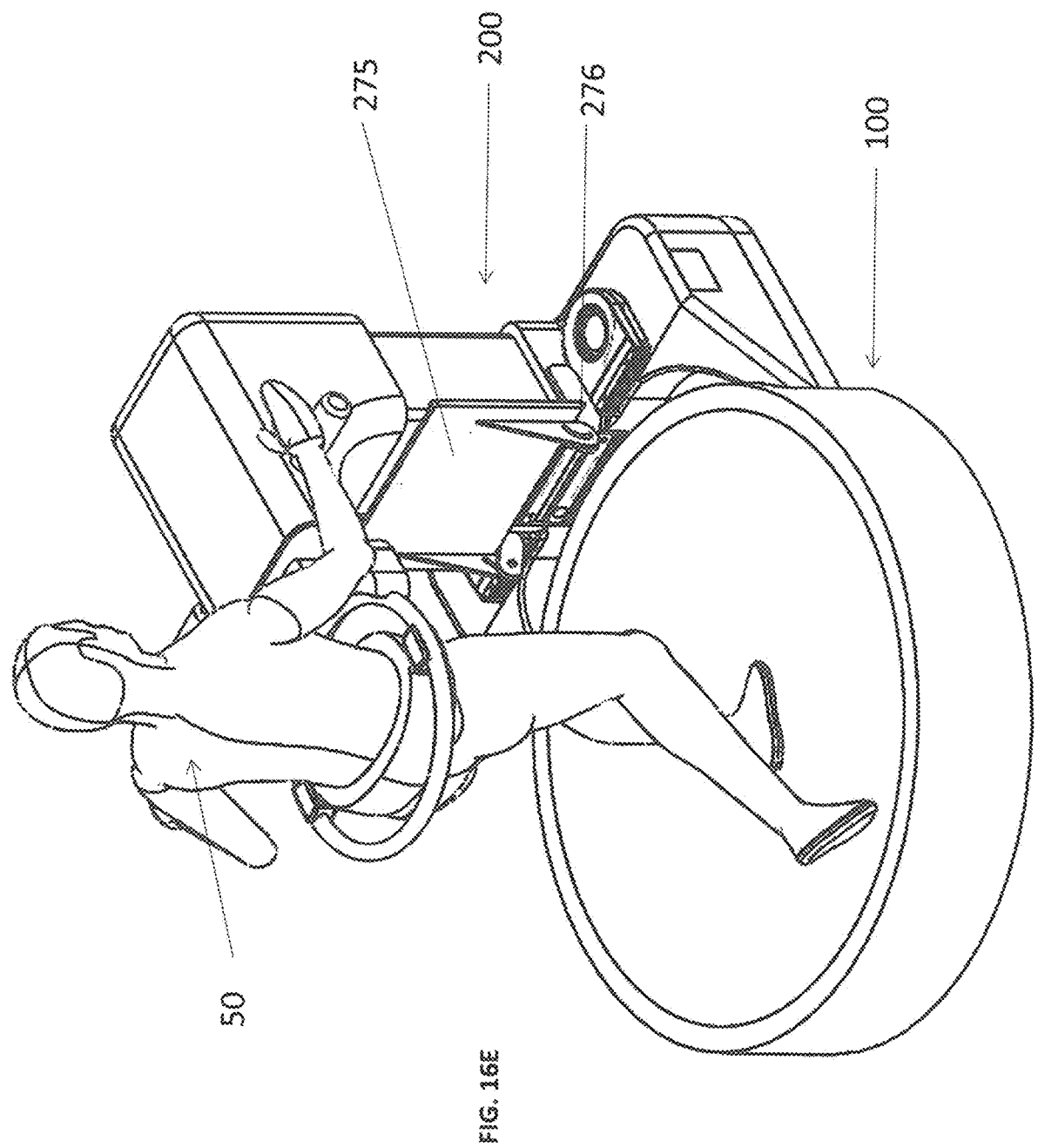

FIG. 16C shows a user 50 supported by the platform 275 and held by the HIA 230, which is attached to the adapter 210. FIG. 16D shows the user 50 in the GMS 200 of FIG. 16C, where the GMS has been moved by an operator to interface with the ODT 100, safely positioning the user over the useful area of the ODT 100. FIG. 16E shows the user 50 using the GMS 200, after having stepped into the ODT 100 from the platform 275. The platform 275 is returned to its stowed position, while the user ambulates and uses the ODT 100 and the GMS 200 as described previously.

Figure 17A:
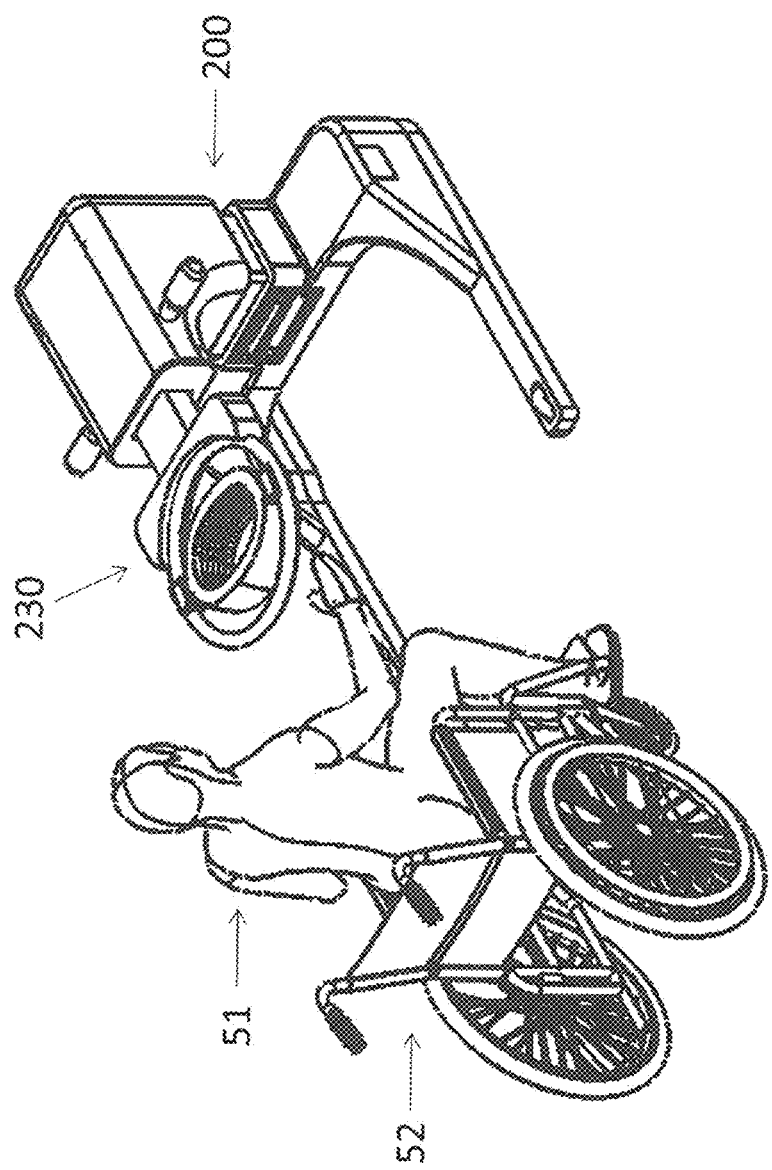
FIGS. 17A-17C are perspective views showing the GMS in operation to receive a wheelchair user.
Figure 17B:
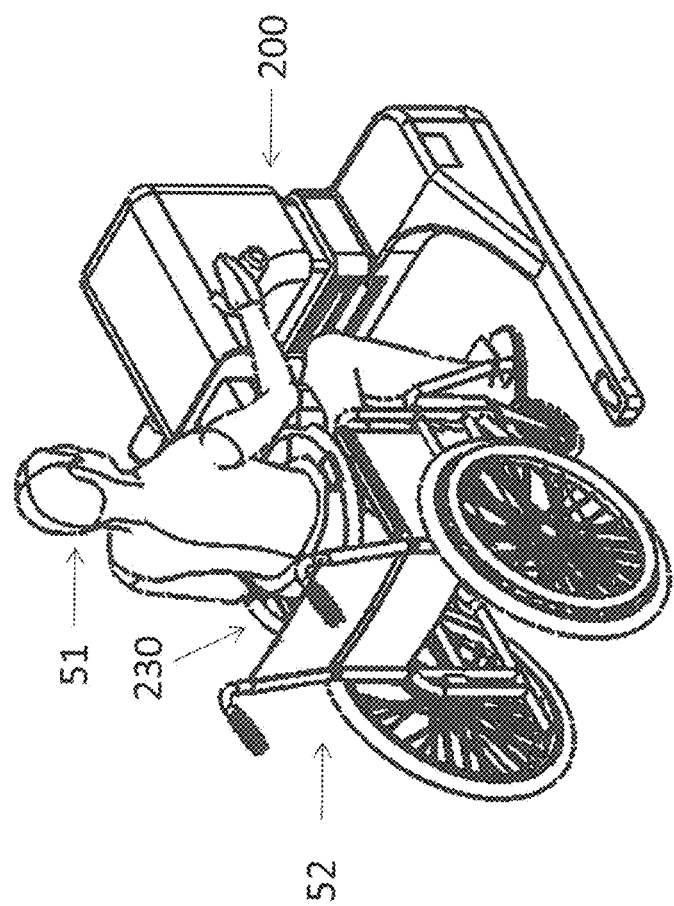
Figure 17C:
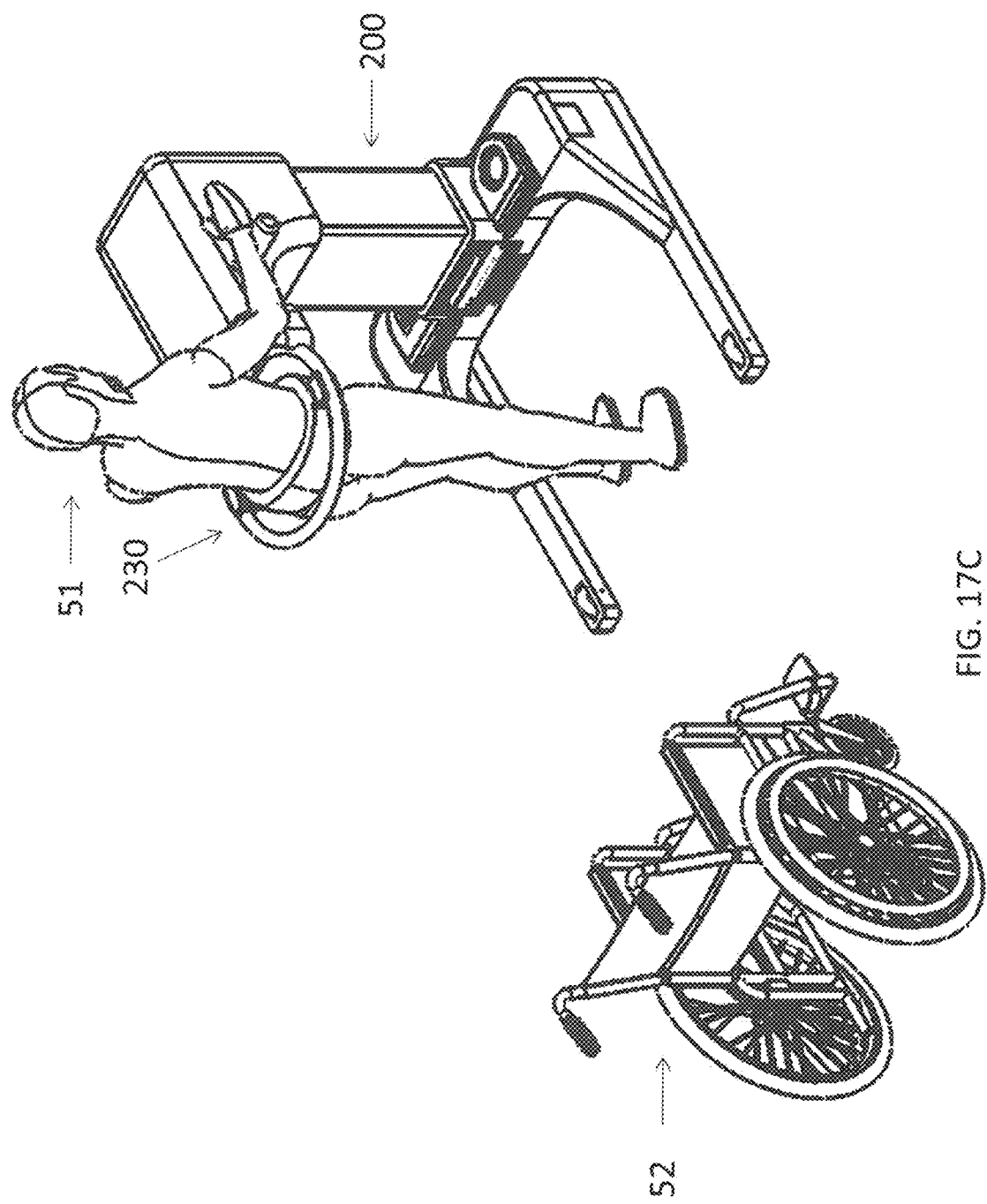

FIG. 17A shows a wheelchair bound user 51 accessing the GMS 200. The HIA 230 is, for example, lowered by the arm support 207 to a position accommodating wheelchair access by the user 51. In FIG. 17B, the user 51, seated in the wheelchair 52, has the HIA 230, in particular, the harness 242, around his midsection, for example, at the waist. The arm support remains at the same position as per FIG. 17A, or it has been adjusted slightly to accommodate the wheelchair user 51. In FIG. 17C, the user 51 is now standing in the HIA 230, and using the GMS 200, after having been, for example, assisted in standing up from the wheelchair. The wheelchair has been cleared from the immediate and operative area of the GMS 200.

FIG. 18 shows a user 50 using the GMS 200 while walking on a treadmill 500, where the crossbar support 203 is elevated such that it can accommodate the treadmill underneath it.

Figure 19:
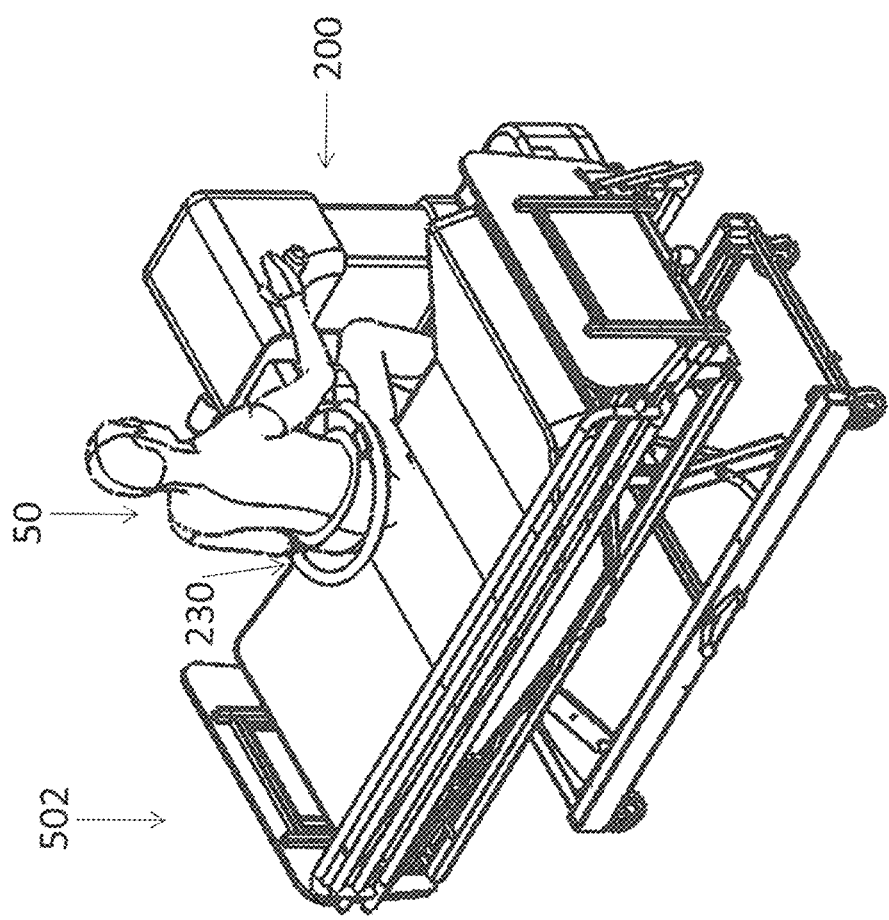
FIG. 19 is a perspective view showing the GMS in use with lifting a user from a bed.

FIG. 19 shows a user in an HIA 230 connected to the GMS 200, on a bed 502. As described in FIGS. 17B and 17C, the GMS may for example, assist the user in standing up and walking over ground, as described in FIG. 16.

Figure 20A:
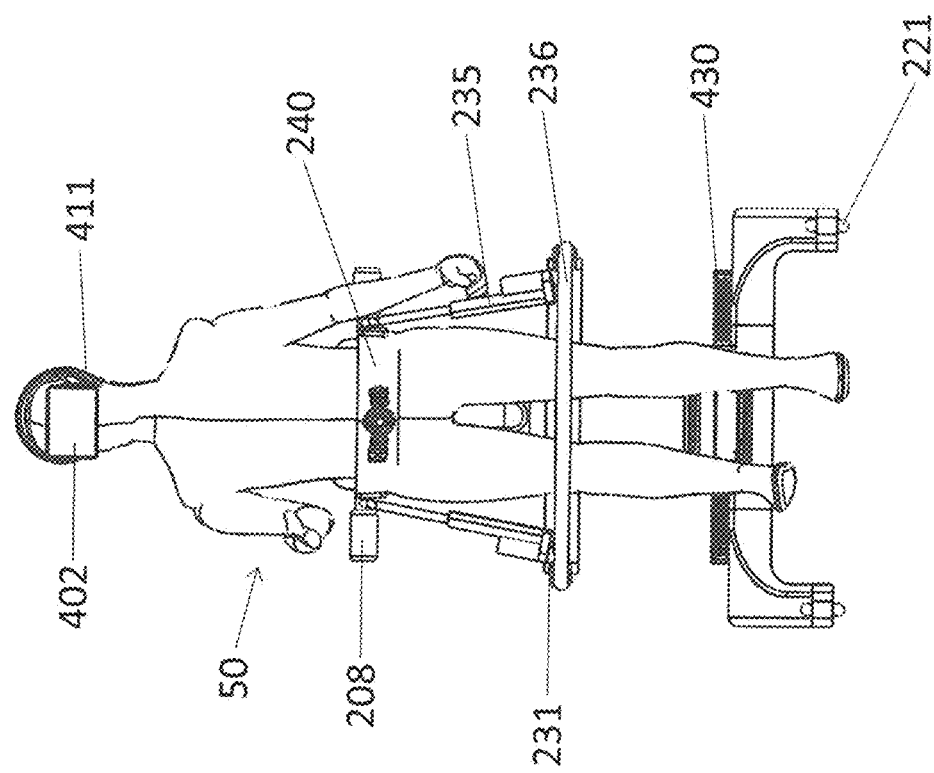
FIG. 20A is a front view of a user operating a mobile GMS.
Figure 20B:
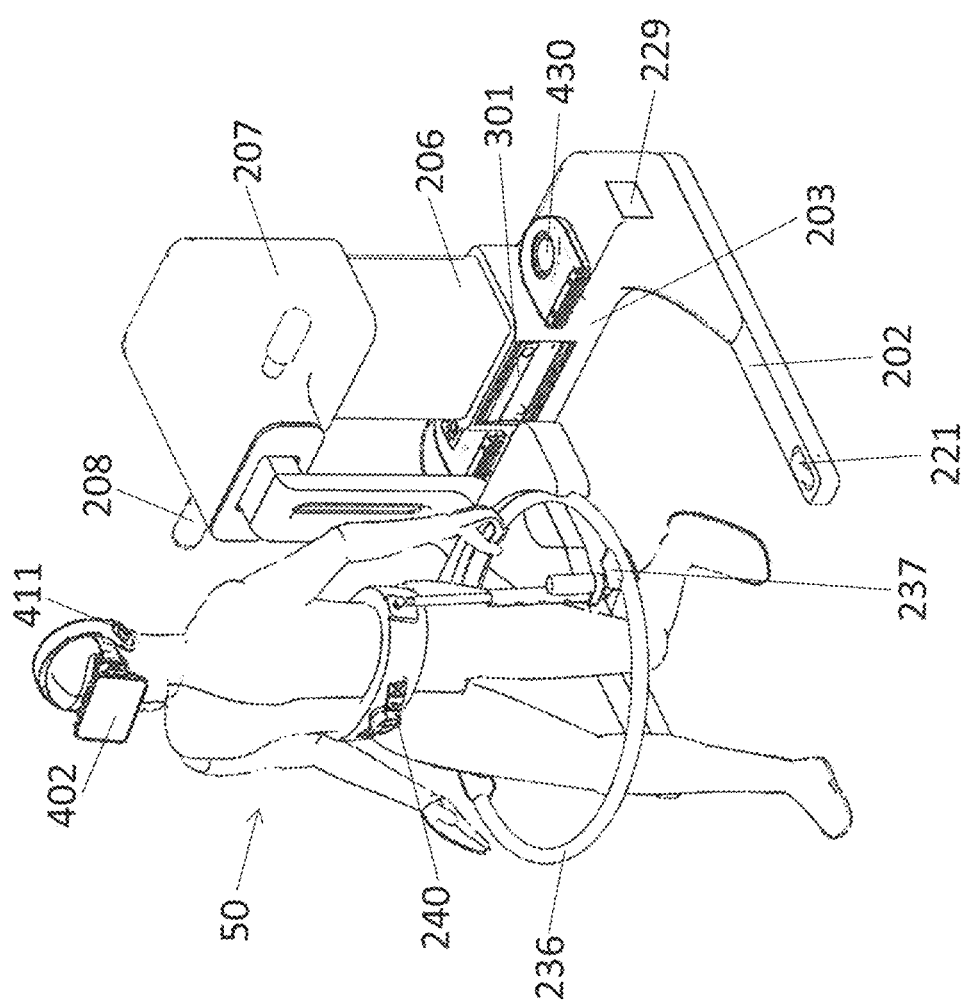
FIG. 20B is an isometric view of a user operating a mobile GMS including an Atmospheric Simulation System (ATSS)

FIGS. 20A and 20B show the user 50 in the GMS 200 with the ring 236 of the HIA 230 below the user's fingertips. Here, the user 50 is wearing a virtual reality headset 402 as part of the VSS 920 and earphones 411 as part of the AUSS 930. The port 430 of the ATSS 960 simulates the desired atmospheric conditions for a simulation, as discussed below.

The GMS structure and HIA together provide, for example, one or more degrees of freedom (DoFs). The mechanisms enabling said DoFs may be located at various points within the GMS and/or HIA. Each DoF may or may not have a) actuators; b) sensors; c) components providing elastic support, or flexure; d) a control system which realizes an open or closed control loop.

In a one embodiment, the GMS may have a subassembly introduced into the structure, allowing the GMS to be mobile. This includes, for example; a) one or more wheels 221, 222; b) one or more elements for vibration damping/reduction (not shown); c) a mobile power subsystem, depicted by the battery 229. In another embodiment, the mobility subassembly may also include: d) a mobile computing platform 470; e) support for sensors, enabling them to be used on a mobile platform (e.g. mechanical, electrical, electronic); f) support for electronic devices (e.g., HMD 402) allowing them to be used on a mobile platform; g) an actuated motion system, for examples, motors (not shown) for driving the wheels 221 and 222.

The mobility subassembly may be controlled or uncontrolled. In an uncontrolled embodiment, the lateral (forward/backward, left/right) forces applied by the user are those that move the entire structure. In a controlled embodiment, actuators may apply force to the mobility subassembly components, for example wheels 221 and 222, and assist the user in moving with the device. The actuators may be controlled by user or operator input, for example, a hand control, or may be for example, controlled by a control system, which may use sensors to acquire data and generate commands for the mobility subassembly. Components of the mobility subassembly include for example, motors, brakes, gears, bearings, motion sensors, position sensors, and a control system.

In order to provide unlimited range of motion to the user in the yaw axis, a cable management solution must be implemented to prevent twisting and tangling of cables connected to the user from any of the MSS subsystems or components. These could include for example: HMD 401, biomedical sensors 501, actuators, headphones 411. In one embodiment, all such hardware worn by the user 50 or connected to the user is connected to a wearable pack 702, which is worn by the user 50; for example, attached to the harness 242. Cables from worn hardware may be connected to the pack 702, which may transmit data wirelessly to the MSS computer(s) 470. In another embodiment, all such data may be transmitted via a slipring (not shown).

GMS Control

The GMS 200, as a force applying unit 200a, may apply an upward or downward force on the user, thereby offloading or overloading a portion of the user's weight. This may be done to offload or overload a portion of the user's weight by percentage, mass, or in order to simulate environments with a smaller or larger gravitational force (e.g. Mars). Alternatively, this may be done to allow the user to perform the actions described previously, such as walking, with the perception of more or less weight. This force is, for example, constantly maintained, as the intention may be to simulate a constant gravitational force that, for example, Mars, would have on a user, regardless of whether the user is standing, running, jumping, or performing any other action. In an environment with greater than 1G, the GMS must apply a downward force on the user. In one embodiment, where the desired simulation environment is in 1G, the GMS 200 may apply a force of or near zero Newtons upon the user.

Many control approaches may be used, such as position, torque, force, and hybrid. Examples of hybrid control approaches include: force-position, torque-position.

One or more sensors, for example, 225a, 225b, 226, 257a, 257b, may be used to obtain measurement(s), which may be used to control force being applied by the GMS 200. Such sensors may include but are not limited to: force sensors, load cells, tension cells, optical sensors, position sensors.

In one embodiment, one or more sensors are used to measure the force being applied to the user at a frequency of at least 1 Hz. This device provides data to, for example, the GMS controller 810, the DAS 910, or any other MSS subsystem, such that they may compute the required output the actuator(s) in the GMS 200 in order to maintain the desired force. Numerous force measuring devices are suitable, for example, torque cells and linear load cells (tension, compression). Force may also be deduced through proxy measurements, such as position. In one embodiment, one or more optical sensors may be used to determine the user's position.

The force to be applied by the GMS 200 is calculated as follows:

$$F_a = M_u \cdot g_E - (M_u \cdot g_{sim})$$

where:

$F_a$ is the force to be applied by the GMS (kg·ms$^{-2}$)

$M_u$ is the mass of the user (kg)

$g_E$ is the Gravitational acceleration on Earth (ms$^{-2}$)

$g_{sim}$ is the Gravitational acceleration at the desired simulation location (ms$^{-2}$)

Alternatively, the following equation is usable to determine the force to be applied by the GMS using the multiple of Earth's gravity at the desired simulation location:

$$F_a = M_u \cdot g_E - (M_u \cdot g_E \cdot g_{Frac})$$

where:

$g_{Frac}$ is the ratio of Earth's gravity and the desired simulation location

Alternatively, the following equation may be used to determine the force to be applied by the GMS using a percentage of the user's terrestrial weight:

$$F_a = M_u \cdot g_E \cdot (1 - P_D \div 100)$$

where:

$P_D$ is the desired percentage of the user's weight

If the desired simulation location is Mars, with a Gravitational acceleration of 3.711 ms$^{-2}$, and the user mass 60 kg, the force to be applied as per the aforementioned equations is 365.76 kg·ms$^{-2}$.

In an alternative embodiment of the GMS 200, the user may wear one or more magnetic elements. A magnetic field may be induced and controlled, such that it generates the desired force on the various magnets the user is wearing, thereby providing a higher-fidelity simulation. Alternative embodiments for the GMS include the use of acoustic and other force-generating systems.

Motion and Gesture Tracking System (MTS)

The Motion and Gesture Tracking System (MTS) 900 captures the user's motions and gestures for use by the various MSS systems. This is achieved by using at least one sensor, for example, a camera 401. The type of sensor(s) to be used includes for example: IMU, accelerometer, gyroscope, magnetometer, GPS, IPS (indoor positioning system), and other localization, positioning, and tracking sensors. The sensors, for example, may include one or more of sensors 225a, 225b, 226, 257a, 257b, 401. The sensor(s) may be mounted on the ODT 100, GMS 200, harness 240, user 50, or any other component of the MSS 75. The term "camera" herein refers to many sensory devices, including, for example, visible-light cameras, IR (infra-red) cameras, UV (ultraviolet) cameras, laser scanners, and any other device that may be used for tracking the user's body.

The camera or sensor data may read by the computer 470, recorded, and for example, may be used at by other parts of the MSS 75, for example, the Data Analysis System 910, or any other MSS subsystem.

The MTS 900 may take on a variety of embodiments, and the sensor configuration may depend on the region of interest.

Data Analytics System (DAS)

The Data Analytics System 910 analyzes data coming from various components within the MSS 75. The analysis may serve a wide variety of functions, including for example: motion analysis, gesture analysis, gait analysis, motion smoothness, and kinetic parameters for any part of the body, including for example: position, distance, speed, acceleration, force, energy. This initial analysis can serve as the basis for further, more specific analysis depending on the use case or application. For example, in conducting gait analysis, the positions of all joints may be known from the MTS 900. The DAS 910 may then calculate such parameters as stride length, velocity, and the likes.

Visual Stimulation System (VSS)

The Visual Stimulation System (VSS) 920 provides the user visual input corresponding to the desired simulation. The visual stimulation may be related to the simulation being undertaken, or not; in which case, they may be related to objectives set forth by the operator. The VSS 920 includes, for example, one or multiple devices, including but not limited to a Virtual Reality (VR) headset 402, Artificial/Augmented Reality (AR), Mixed Reality (MR), Hybrid Reality (HR), television(s), monitor(s), projector(s) with projection surface(s), holographic display(s), heads-up display(s), or any other type of visual display.

The VSS 920 may display different types of information, which are, for example, separated into layers, which may or may not be related or connected to one another. In one embodiment, the background layer is a content layer, where a chosen environment is displayed for the user. The background layer may contain static, dynamic, or interactive content. Static content may be content which is simply displayed for the user. Dynamic content may be content that changes over time, but is not influenced by the user's action(s). Interactive content is content that may change in response to the user's action(s). The foreground layer may be a feedback layer, providing specific inputs to the user, relevant to their simulation. For example, if the simulation is being used as a physiotherapy tool, the foreground layer may provide corrective feedback to the user in real-time, helping to improve their motions or gestures.

In one embodiment, a VR headset 402 is used as part of the VSS 920, displaying one or more layers of data, for example, a background layer and a foreground layer; one or more of which may be interactive. The user may, for example, need to kick a virtual ball in one of the layers with every stride, and the ball may pop or have its path diverted in accordance with the kicking action executed by the user. Furthermore, one of the layers, for example the foreground layer, provides analysis metrics to the user, for example, gait analysis metrics such as stride length, symmetry, speed, and the like.

Game Engine System (GES)

A Game Engine System (GES) 990 provides software which may include, for example, a graphics engine, a physics engine, a scripting engine, a suite of visual development tools, a suite of audio development tools, a suite of tactile feedback tools, development tools and a large set of reusable software components. The GES 990 abstraction may be in the form of software framework. The GES is, for example, used to a) design the simulation environment in which the user is immersed; b) control the physics of the simulation; c) appropriately design the interactivity of the user with the immersive environment.

The GES 990, for example, interfaces with the ODT 100, GMS 200, MTS 900, Controller 810, GSS 985 or with other MSS systems through the communication bus 750.

The GES may be driven by the ODT 100, GMS 200, MTS 900, Controller 810, GSS 985, or by other MSS subsystem in order to allow the user to interact with a scene through use of motion or gestures. The GES may be driven by the MSS operator.

Controller

The controller 810 provides, for example, the following services:

Initialization: Starts all relevant processes and checks that they are running nominally.

Simulation configuration management: Manages the simulation configuration, including all relevant parameters for all relevant systems and subsystems.

Coordination and synchronization: Coordinates and synchronizes all relevant systems and subsystems.

Logging and archiving: Ensures that data from all relevant systems and subsystems is logged and archived, where relevant.

Message delivery and format integrity: Ensures that messages are not lost or duplicated and that they are delivered uncorrupted.

Load balancing: Redistributes the processing load to allow load balancing over the available processing units.

Security: Ensures security of communications using appropriate security protocols.

The controller 810 may communicate with database(s) external to the MSS, for example Electronic Health Records (EHR), Electronic Medical Record (EMR) using the CU 820.

Figure 23A:
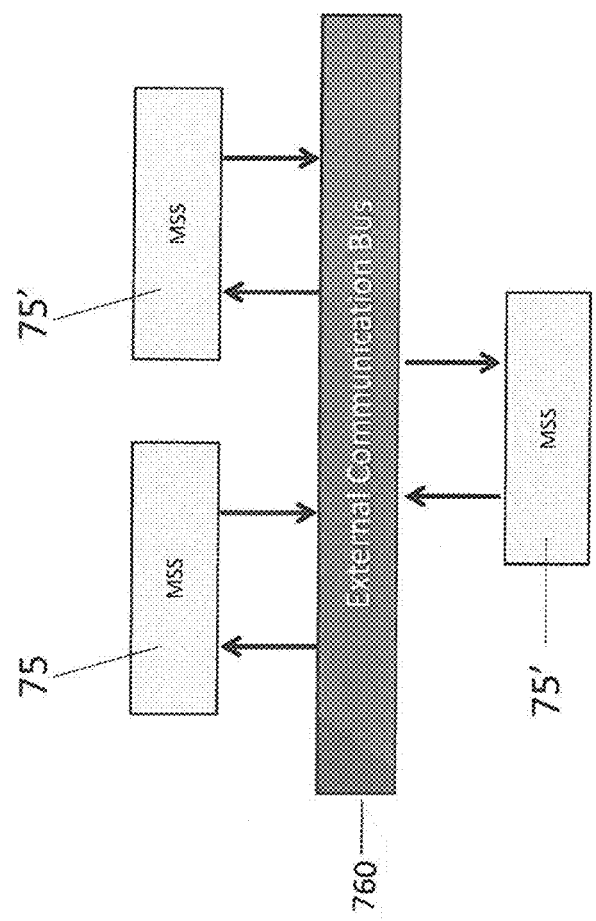
Figure 23B:
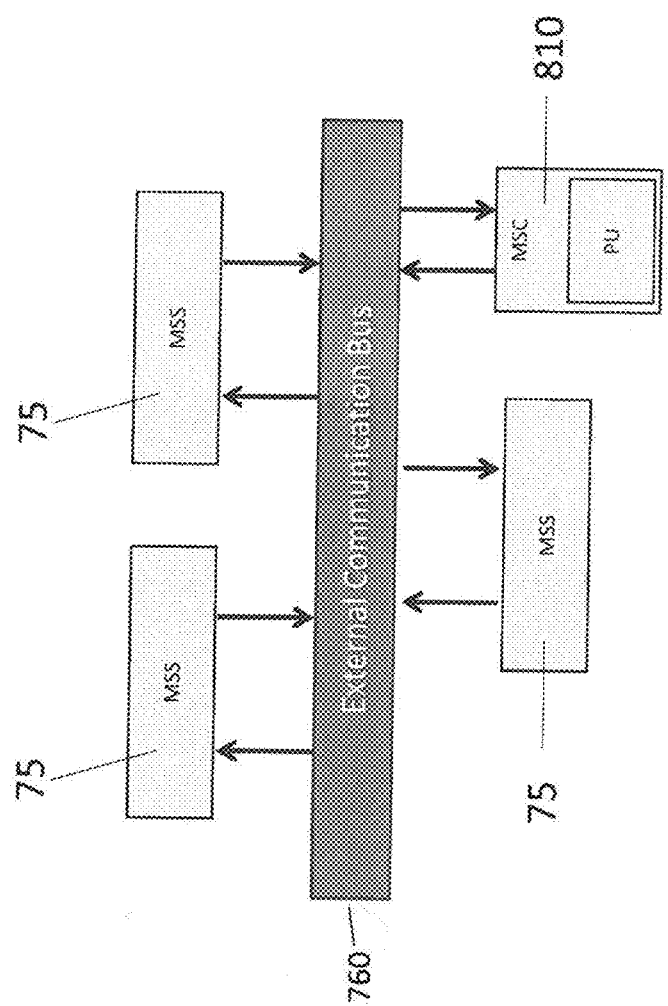

The controller may communicate with other MSS 75/75' units, allowing a multi user simulation environment. This is achieved, for example, using a master 75/slave 75' configuration, via an external communication bus 760, as shown in FIG. 23A. In another embodiment, a Controller 810 may be used to control the multiple MSS 75 units, via an external communication bus 760, as shown in FIG. 23B.

Auditory Simulation System (AUSS)

The AUSS 930 simulates the auditory inputs to be perceived by a user in the simulated environment. These may be related to the simulation being undertaken, or not; in which case they may be related to objectives set forth by the operator. The auditory data may be driven by the ODT 100, GMS 200, MTS 900, Controller 810, GES 990, or by other MSS 75 subsystems. The auditory data may be driven by the MSS 75 operator.

The audio signal may be supplied via a communication bus 750. Audio devices include, for example, speakers 260, headphones 411, and any other device that may be used to generate auditory stimulation in the user.

The speakers 260 are, for example, integrated into the structure of the ODT 100 or GMS 200. The system may provide a 3D audio signal for higher simulation fidelity. In one embodiment, the auditory stimulation is provided via headphones 411 worn by the user 50 (FIG. 1A).

Operator Interface System (OIS)

The OIS 800 provides, for example, a user interface for the provision of input to the system by a user/operator, and for the display of data and or feedback from the system to the user/operator.

Such an interface may be housed on any component of the MSS 75. The interface includes, for example, one or more of the following: touch screens 701, push buttons, dials, digital or analog displays, switches. Furthermore, the user or operator may be able to control and monitor the MSS 75 and receive all relevant data via external devices, including for example, Personal Computers (PCs), tablets, such as iPads®, smartphones, laptops. The interface between the MSS and MSS subsystem(s) and these devices may be wireless or wired.

In one embodiment, the user interface is provided via a touch screen 701 mounted onto the GMS 200 structure, shown for example, in FIG. 7.

User Harness System (UHS)

The User Harness System (UHS) 940 provides an interface between the user and the HIA 230. The UHS 940 comprises, for example, a harness assembly 240, sensors 257a and 257b, and actuators 258.

FIGS. 12A and 12B show an inflatable embodiment of the harness 242 in a deflated (FIG. 12A) and an inflated (FIG. 12B) configuration. The harness 242 may contain one or more bladder(s) 250, which may be divided into compartments (not shown). The harness 242 may also include a pump 258 for filling the bladder(s) 250 with fluid for example, via tube 258a. The fluid used may include gases and liquids, for example: atmospheric air, nitrogen, carbon dioxide, water, and various gels. The filling fluid may be actively moved between the bladder(s) 250 and reservoir(s) (not shown) via one or more tubes, hoses or pipes (not shown), such that a desired pressure is achieved, using for example, a pump 258. Pressure in the bladder(s) 250 and/or between the bladder(s) 250 and the harness material, and/or between the harness 242 or bladders 250 and the user may be measured using a variety of sensors, including pressure sensors. One or more valve(s) 259 may be introduced to the bladder(s) 250, between multiple bladders, and between the bladder(s) and the supply hose 258a and pump 258, in order to regulate fluid flow and/or regulate pressure. In this embodiment, the bladder(s) 250 are, for example, contained within the harness construction. The UHS 940 includes, for example, rigid members (not shown) providing stiffness to an inflatable harness, preventing it from rolling up or down the user's body with the application of positive or negative force on the harness by the GMS 200.

Sensors included in the UHS 940 are for example, sensor 257a, which is used for measuring the user's physiological parameters such as heart rate, pulse, skin temperature, waist width, waist circumference, and the likes. Sensor 257h is for example, a motion, position, and/or length measurement sensor, such as an IMU, accelerometer, magnetometer, gyroscope, strain gauge, pressure sensor, tension sensor, photosensor, and the likes. This sensor allows motion tracking of the user's hips, measuring the user's waist width, waist circumference and other similar parameters. Furthermore, the belt may include markers (not shown), which may be passive or active, for motion tracking.

The advantages of such a harness design are that it: a) Can conform to a very wide range of user shapes and sizes with minimal adjustment; b) distributes the forces being applied to the user evenly or nearly evenly over a large area, thereby ensuring a better grasp on the user, and reducing discomfort, pain, and potential adverse effects to the user's Circulation, Sensation, and/or Motion; c) reduced donning and doffing times.

The harness 242 is designed to fit very snugly, for example, almost exactly, such that the harness and user move in unison, and the user cannot slip, rotate, slide, or otherwise move within the harness. The harness should, to the greatest extent possible, not impair the user's ability to perform any natural movement, action, or assume any position. Furthermore, to the greatest extent possible, the harness should not cause pain or discomfort, or have any adverse effects on the user's circulation of fluids (such as blood and lymph), sensation, or motion (CSM); particularly, but not exclusively, distal to the harness. Many harness designs and materials can be used. One example of such is a commercially available lower-body stunt harness. Full and partial body suits and various other garments are also suitable to perform the desired functions, as do various physical therapy harnesses for lower body, upper body, and combinations thereof, and for the purposes of this document, are included in the definition of 'harness' throughout the document.

Tactile Stimulation System (TSS)

The tactile stimulation system (TSS) 950 reproduces the physical sensations a user perceives in a given simulation environment. These may be related to the simulation being undertaken, or not; in which case they may be related to objectives set forth by the operator. The stimulated sensations, for example, include: pressure, force, vibration, hardness, texture, and temperature of surfaces. The TSS 950 comprises, for example, wearable actuators, such as gloves 205 (FIG. 14-B). The tactile stimulation system 950 may be integrated with the ODT 100, GMS 200, MTS 900, Controller 810, GES 990, or any other MSS subsystem(s).

These components include for example: electrodes, heaters, chillers, inflatable bladders, servos, ultrasonic actuators, acoustic actuator, Eccentric Rotating Mass (ERM), Linear Resonant Actuator (LRA), Piezoelectric, Electro-Active Polymer (EAP), Shape Memory Alloy (SMA) and any other device that may be used to provide tactile stimulation to the user. Electrodes are used to simulate pain, temperature differences, surface contact, but also to stimulate muscles and simulate muscle fatigue.

The stimulation provided by the TSS may or may not be induced by direct physical contact.

Atmospheric Simulation System (ATSS)

The atmospheric simulation system (ATSS) 960 simulates the desired atmospheric conditions in the simulation. These may be related to the simulation being undertaken, or not; in which case they may be related to objectives set forth by the operator. The ATSS may be integrated with the ODT 100, GMS 200, MTS 900, Controller 810, GES 990, or by any other MSS subsystem. Its components, for example, include but are not limited to: fans, heaters, air conditioners, humidifiers, dehumidifiers, radiators, mist generators, and spotlights.

User Monitoring System (UMS)

The UMS 987 monitors user-specific parameters. The parameters are for example, recorded and logged, used as inputs for other MSS subsystems, including but not limited to, the USS 995, the DAS 910, the VSS 920. The UMS 987 may collect a wide variety of parameters, for example: Heart rate (HR), invasive or non-invasive blood pressure (IBP or NIBP, respectively), galvanic skin response (GSR), respiration rate (RR), respiratory volume (RV), oxygen saturation (SpO2), oxygen perfusion (perf), oxygen consumption, skin color, skin temperature, skin texture, metabolic rate, pupil dilation, blood glucose level (BGL), blood gases, protein levels, electrocardiogram (ECG), electromyograph (EMG), electroencephalogram (EEG), cutis anserine (goosebumps), cardiac output, digestive system function.

The aforementioned parameters, and others, may be monitored and measured by various sensors and methods. They may be monitored using sensors that are, or are not, in contact with the user. In one embodiment, these sensors for any given parameter may be integrated into the present invention, and made to interface with the UMS 987 through a communication bus 750.

Neurological Stimulation System (NSS)

The Neurological stimulation system (NSS) 970 provides neurological stimuli to the user. These may be related to the simulation being undertaken, or not; in which case they may be related to objectives set forth by the operator. For example, such an objective may be clinical in nature, in the case of physical therapy, where neurological stimulus may be used in conjunction with the remainder of the simulation for improved clinical outcomes, resulting from the synergies between the modalities. The neurostimulation may be invasive or non-invasive in nature. An example of an invasive technique is the use of electrodes to provide the neurostimulation, as in Deep Brain Stimulation (DBS), whereas non-invasive techniques include Transcranial Magnetic Stimulation (TMS) and Transcranial Electric Stimulation (tES), which may use DC or AC current (tDCS, tACS, respectively) passed through electrodes 451.

The neurological stimulation may be integrated with the ODT 100, GMS 200, MTS 900, Controller 810, GES 990, or by any other MSS subsystem. The neurological stimulation may be driven by the MSS operator.

Olfactory Stimulation System (OSS)

The Olfactory Stimulation System (OSS) 980 produces an olfactory input for the user. This may be achieved through the storage and release or synthesis of odor molecules from one or more reservoir(s) 430, emitters, or other elements. These molecules may be released in conjunction with the simulation the user is undergoing, in order to increase the fidelity of the simulation that the user is undergoing. Dosage of the odor molecules may be controlled by the operator. In one embodiment, the OSS 980 is used to help treat an Alzheimer's disease patient; whereby the VSS 920 and the OSS 980 are used together to provide coordinated inputs relating to a particular scene, in order to improve memory, reduce anxiety, reduce depression, and/or improve cognitive function in the user.

The olfactory stimulation may be related to the simulation being undertaken, or not; in which case they may be related to objectives set forth by the operator. The olfactory stimulation may be driven by the ODT 100, GMS 200, MTS 900, Controller 810, GES 990, or by any other MSS subsystem. The olfactory stimulation may be driven by the MSS operator.

Gustatory System Stimulation System (GSS)

The Gustatory System Stimulation System (GSS) 985 operates to: simulate tastes, and to stimulate the tongue and gustatory system as a sensory input, leveraging its relatively large representation in the cortex. The stimulations may be achieved, for example, through the use of electrical stimulation by one or more electrodes 461 and temperature variations in the tongue, both in order to achieve taste simulation and also stimulation for other purposes. There are a wide variety of other purposes for stimulating the tongue, since it has a large cortical representation, and can therefore be used for numerous clinical and other applications. In one embodiment, electrical stimulation of the tongue is used to treat patients with gait disability, where the GSS is used in conjunction with the GMS, MTS, VSS, and OSS in order to provide coordinated inputs to the user. This use of coordinated inputs may be used, for example, to improve postural and gait stability.

The gustatory stimulation may be related to the simulation being undertaken, or not; in which case they may be related to objectives set forth by the operator. The gustatory stimulation 985 may be driven by the ODT 100, GMS 200, MTS 900. Controller 810. GES 990, or by any other MSS subsystem(s). The gustatory stimulation may be driven by the MSS operator.

User Safety System (USS)

The User Safety System (USS) 995 is responsible for ensuring the safety of the user while in the MSS 75. It operates by analyzing inputs from the various MSS subsystems and other sensors of the MSS 75, and upon detection of an anomaly, or situation defined as unsafe, it produces for example, a specific response, making the system safe. Input sources to the safety system include but are not limited to: optical sensors, force sensors, temperature sensors, motion sensors, electrical sensors, and others. Once acquired, the safety system may use a processing unit to evaluate normalcy of the sensor parameters. If a situation defined as unsafe is detected, the safety system may take action to render the system safe. Such action includes, for example: changing supplied power to given components of the system, activating actuators (such as brakes) in order to reduce or eliminate motion of given components in the system, activate other actuators (such as motors) in order to move given components of the system to safe configurations, and the like.

In order to improve the performance of the user safety system 995 with respect to existing systems, and to reduce false negatives, the USS 995 may be augmented by motion inputs. In one embodiment, these inputs may emanate from the DAS 910 and the MTS 900.

The USS may or may not be independent from all other MSS subsystems, and may have built-in redundancy to improve reliability.

The USS 995 may be driven by the ODT 100, GMS 200, MTS 900. Controller 810, GES 990, MSS operator, or any other MSS subsystem.

Processing

Attention is now directed to FIGS. 21, 22A-1, 22A-2 and 22B which show flow diagrams detailing computer-implemented processes in accordance with embodiments of the invention. Reference is also made to elements shown, for example, in FIGS. 1A and 1B. The process and subprocesses of FIGS. 21, 22A-1, 22A-2 and 22B are computerized processes performed, for example, by processor(s) 811, 991 of the system computer 470. The aforementioned processes and sub-processes can be, for example, performed manually, automatically, or a combination thereof, and, for example, in real time.

Figure 21:
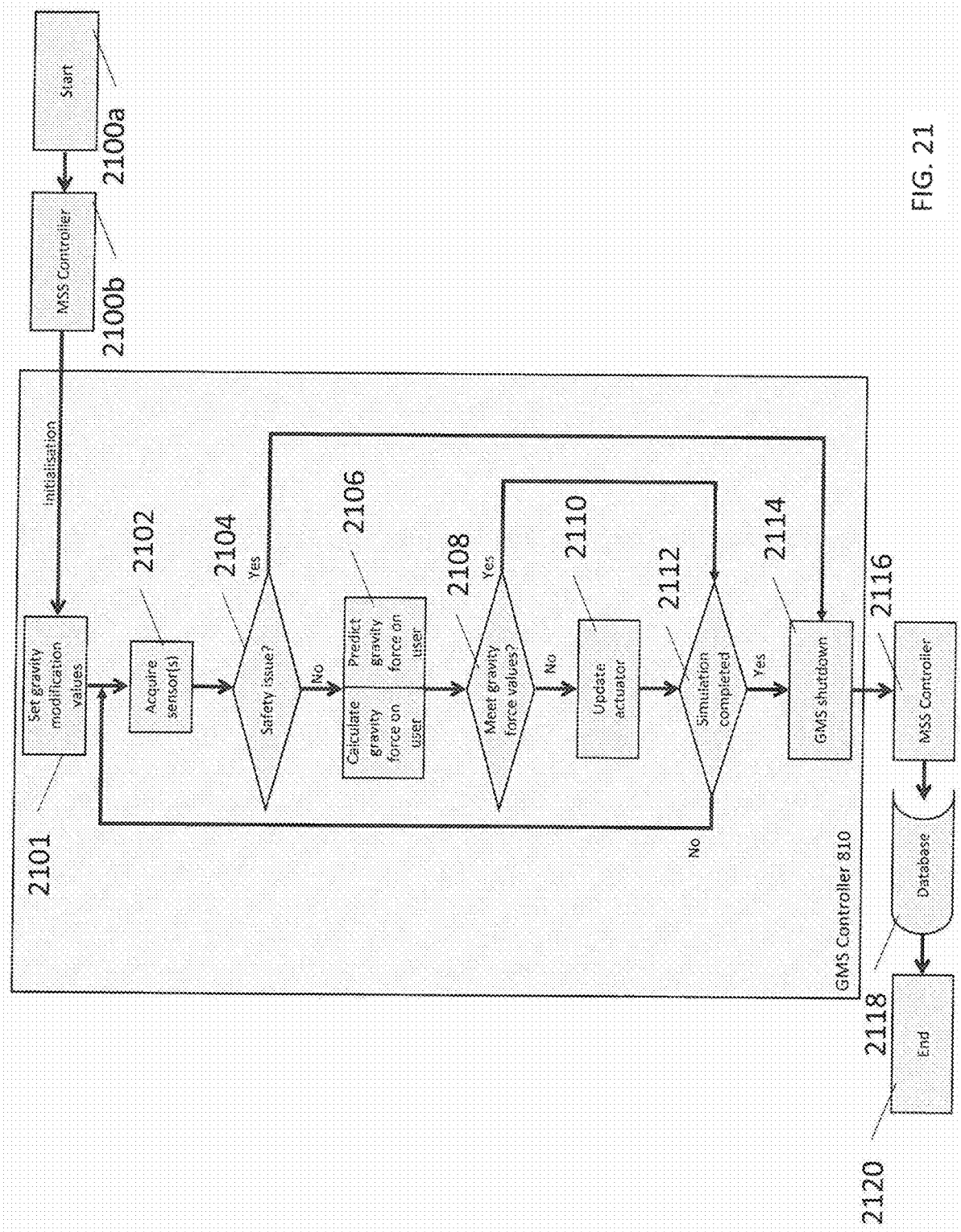
FIG. 21 is a flow diagram for a process performed by the GMS.

The process of FIG. 21 starts at block 2100*a*, and then moves to block 2100*b*, where the MSS controller sends an initialize command to the GMS controller 810. At block 2101, gravity modification values are set, for example, by being entered into the operator interface 701. These gravity modification values are the forces for which the gravity modification will be performed. The process moves to block 2102, where sensor values are acquired, for example, from the sensors 225*a*, 225*b*, 226 of the GMS 200 and 257*a*, 257*b* of the harness 242 (of the harness unit 240). These sensors indicate various forces, positions, movements and the like on the GMS 200, as well as body movement and orientation of the user and physiological data, indicative of physiological conditions of the user, in the harness 242, which communicates with the GMS 200. Safety sensors, for example, 601 of the USS 995, are also acquired.

The process moves to block 2104, where the sensor data is analyzed for safety conditions, such as a user is not present in the harness 242, the physiological data is indicative of a physiological problem, and/or the user is above/below acceptable use thresholds, as well as any malfunctions of the GMS 200, or any safety event sensed by the USS 995. Should there be a safety issue, at block 2104, the process moves to block 2114, where the GMS 200 shuts down. Should there not be a safety issue at block 2104, the process moves to block 2106.

At block 2106, a gravity force on the user is calculated, as described above, and a gravity force on the user is predicted. The predicted gravity force is based on, for example, the user's jumps/jerks, the acceleration first derivative, which can be calculated from the acceleration measured by the sensor 257*b*. The process moves to block 2108, where it is determined whether measured and predicted gravity force values have been met by the actuators. If yes, at block 2108, the process moves to block 2112. If no, at block 2108, the process moves to block 2110.

At block 2110, the actuators, for example, the motors providing the forces in the GMS 200, as well as actuators 114 and other components for changing the surface of the ODT 100 (if an ODT 100 is linked to the GMS 200) are updated with force values from the system computer 470.

The process moves to block 2112, where it is determined whether the simulation is completed. If no, the process moves to block 2102, from where it resumes. If yes, the simulation is complete, and the process moves to block 2114, where the GMS 200 shuts down.

From block 2114, the process moves to block 2116, where the process moves back to the MSS controller 810. The process then moves to block 2118, where the data from the simulation is stored. The process then moves to block 2120, where it ends.

FIGS. 22A-1, 22A-2 and 22B detail a process for performing a simulation. The process starts at the START block 2200. At block 2202, the controller 810 initializes, and at block 2204, the systems, including, ODT 100, GMS 200, MTS 900, DAS 910, VSS 920, AUSS 930, UHS 940, OIS 800, TSS 950, ATSS 960, NSS 970, GSS 985, UMS 987, GES 990 and CU 820, initialize. The process moves to block 2206, where the system computer 470 determines whether the initialization of block 2204 has succeeded.

At block 2206, if no, the initialization has not succeeded, the process moves to block 2224, where the simulation shuts down. From block 2224, the process moves to blocks 2226 and 2228. At block 2226, the data associated with the simulation is stored in a data base, such as database 830, for archiving. Also, the process moves to block 2228, where it ends. If yes, at block 2206, initialization was successful, and the process moves to block 2208. At block 2208, operator input for the simulation, from block 2209, is entered into the OIS 800. The data, including the input from the OIS 800 for the simulation, moves to the controller 810, at block 2210. Parameters for the systems, including, ODT 100, GMS 200, MTS 900, DAS 910, VSS 920, AUSS 930, UHS 940, OIS 800, TSS 950, ATSS 960, NSS 970, GSS 985, UMS 987, GES 990 and CU 820, are updated at block 2212. With the parameters updated, the simulation begins, at block 2214.

Data from sensors, for example, 122, 401, 225*a*, 225*b*, 402, 257*a*, 257*b*, 601, and 501, is acquired, and the process moves to block 2216, where systems, including the ODT 100, GMS 200, MTS 900, UHS 940, UMS 987 and USS 995 are processing the data. Then at block 2218 safety checks are performed. Should a safety issue be detected at block 2218, the process moves to block to block 2224, where the simulation shuts down. From block 2224, the process moves to blocks 2226 and 2228. At block 2226, the data associated with the simulation is stored in a data base, such as database 830, for archiving. Also, the process moves to block 2228, where it ends. Should there not be a safety issue at block 2218, the process moves to block 2220, a simulation block, representing the performance of the simulation. The simulation block 2220 is shown in detail in FIG. 22B.

The process moves to block 2222, where it is determined whether the simulation is completed. If no, the process moves to block 2216 (with a previous acquire sensors step), from where the process resumes. If yes, the process moves to block 2224, where the simulation shuts down. From block 2224, the process moves to blocks 2226 and 2228. At block 2226, the data associated with the simulation is stored in a data base, such as database 830, for archiving. Also, the process moves to block 2228, where it ends.

Figures 1, 22A:
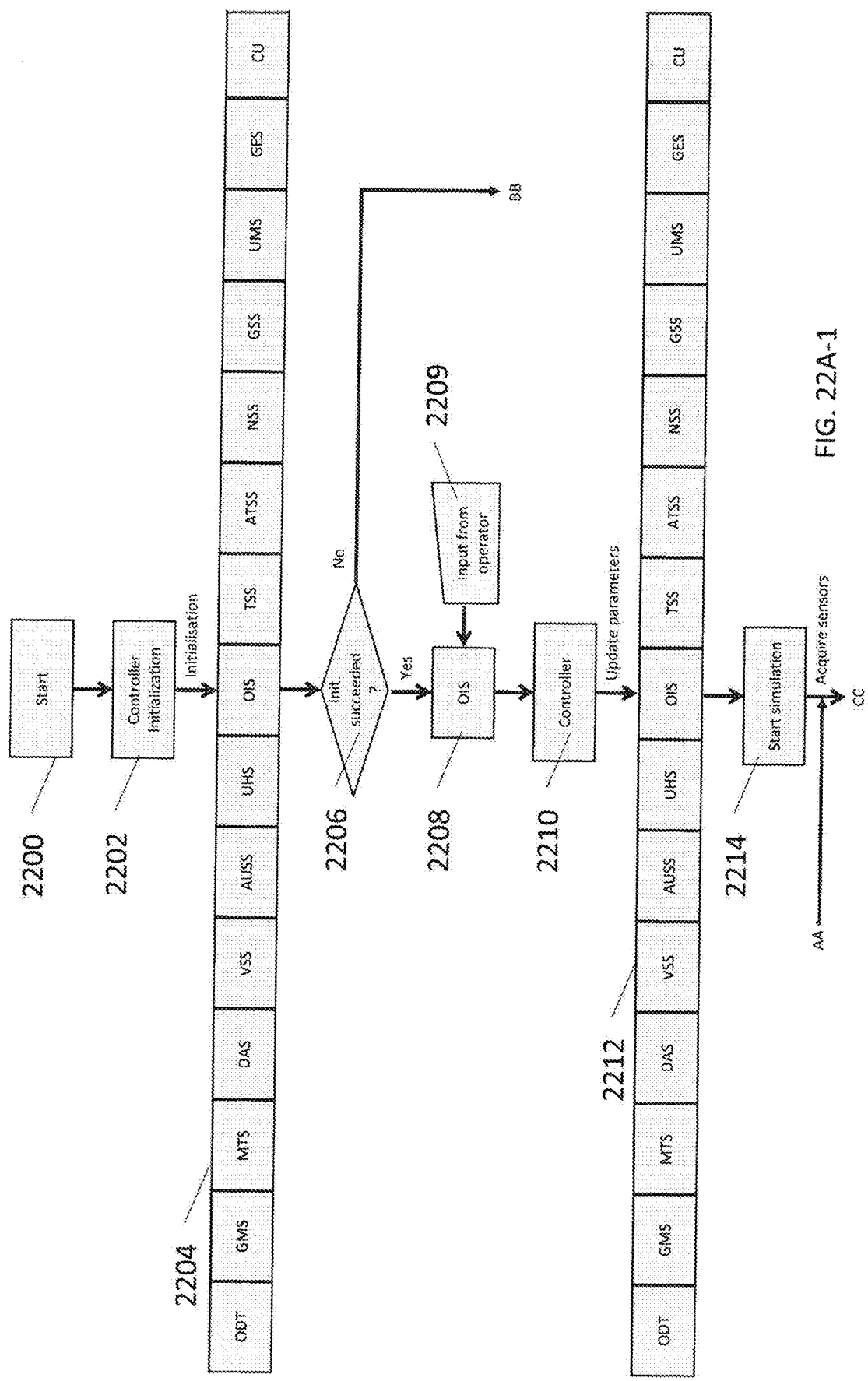
Figures 2, 22A:
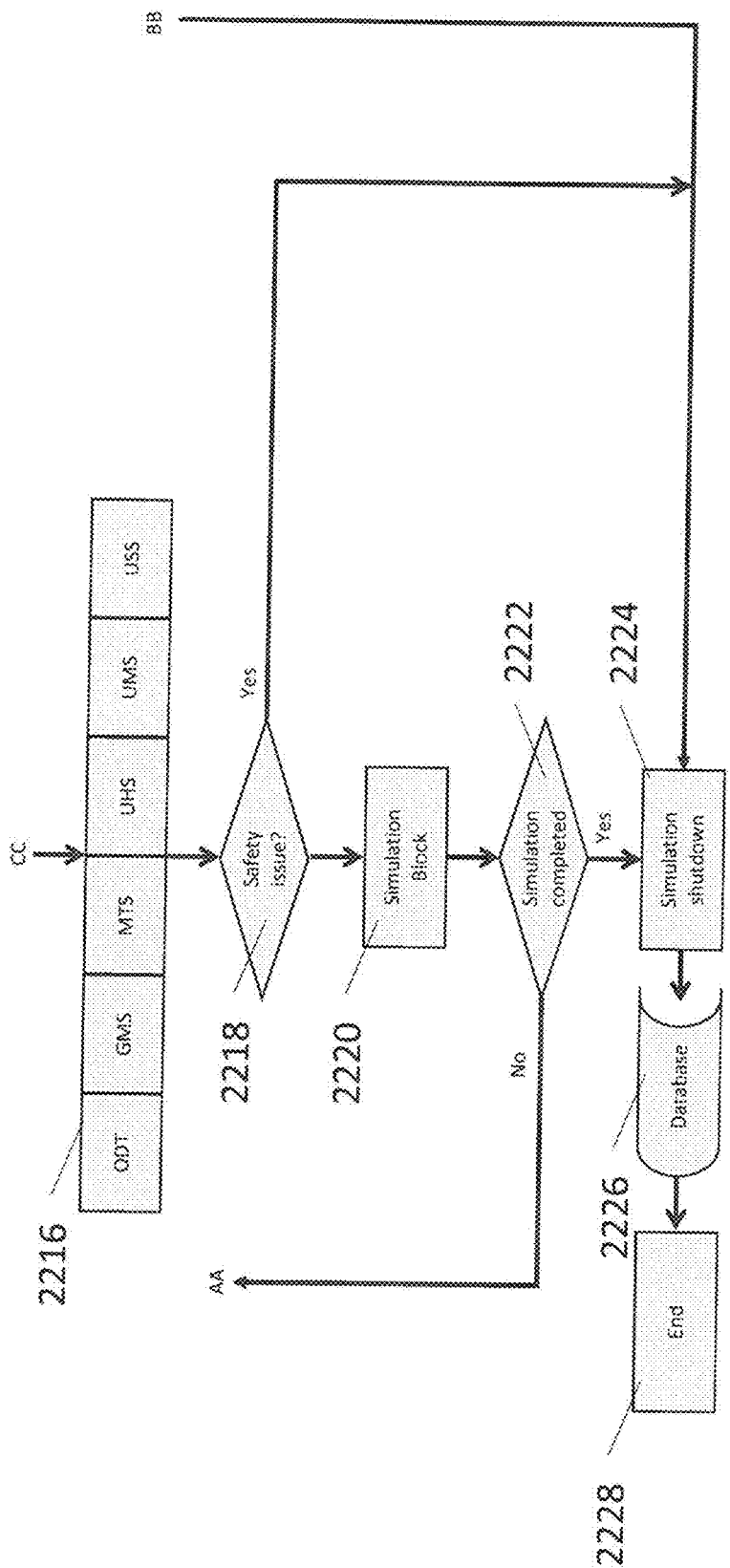
Figure 22B:
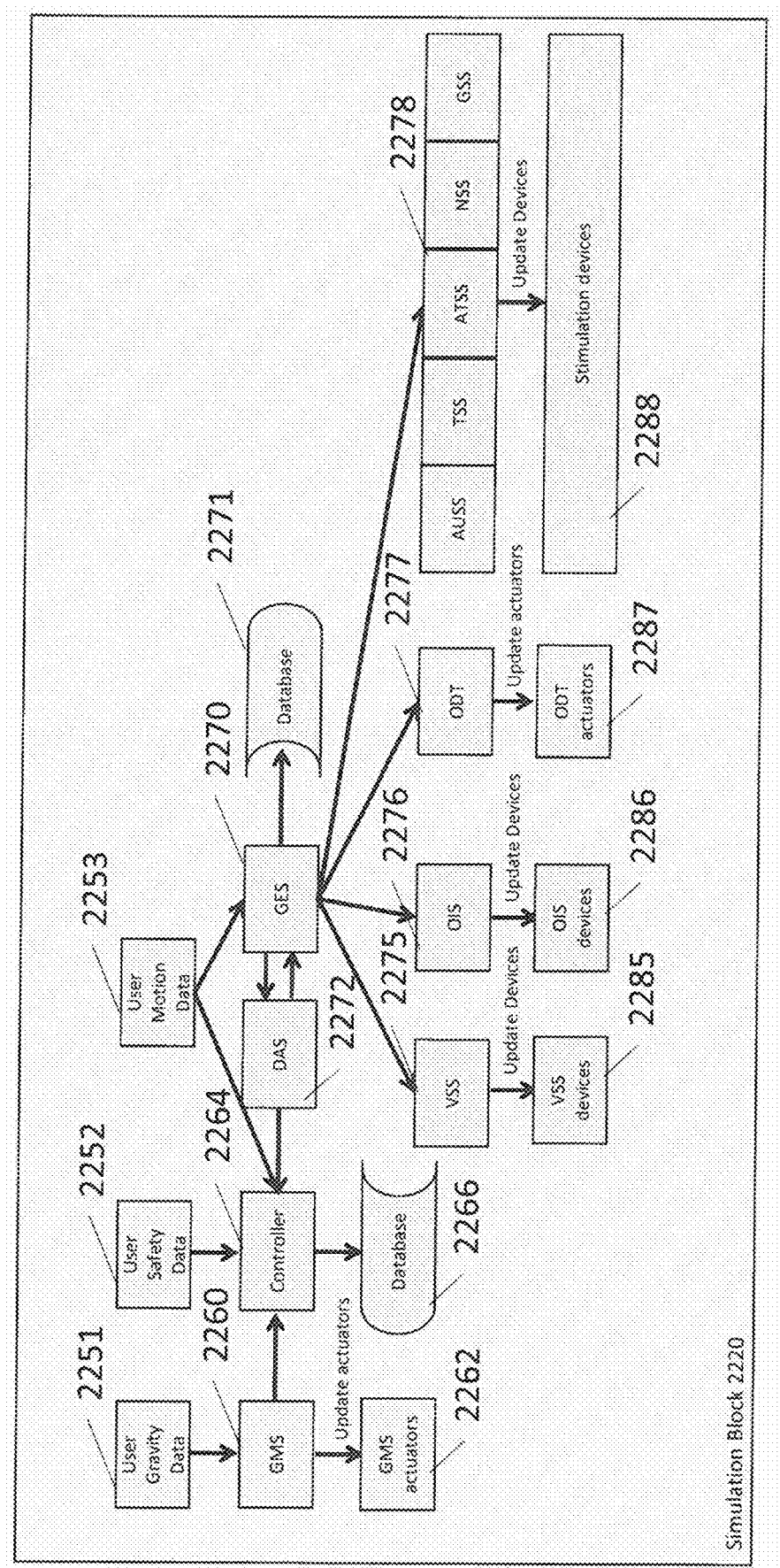

FIG. 22B shows block 2220 in detail. Initially, from block 2218, three strings of data from systems ODT 100, GMS 200, MTS 900, UHS 940, UMS 987 and USS 995 (at block 2216) are acquired as User gravity data, at block 2251, user safety data, as block 2252 and user motion data, at block 2253.

From block 2251, the data is used to update the GMS 200, at block 2260, which updates the GMS 200 actuators, for example, an algorithm running the GMS 200, at block 2262.

The user safety data, from block 2252 and the GMS data, from block 2260, are fed into the controller, at block 2264. This data then goes to the database 830, where it is stored, at block 2266.

The user motion data of block 2253 is sent to the GES 990, at block 2270. This data is fed to the database 830 at block 2271. This data is fed to the DAS 910, at block 2272, where it is processed and then sent back to the GES 2270 block. From the DAS at block 2272, the data is sent to the controller, at block 2264, from where the process continues as detailed above.

The user motion data is used to update the simulation in the GES, at block 2270. Then an output is sent to the VSS 920, at block 2275, to the OIS, at block 2276, the ODT 100, at block 2277 and other systems (AUSS 930, TSS 950, ATSS 960, NSS 970 and GSS 985), at block 2278. From block 2275, VSS devices, e.g. VR headsets, screens and the like, used in the simulation, are updated with data, at block 2285. From block 2276. OIS devices, e.g., laptops, computers and the like, used in the simulation, are updated with data, at block 2286. From block 2277, ODT actuators, e.g., surface actuators, used in the simulation, are updated with data, at block 2287. From block 2278, the devices corresponding to the AUSS 930, TSS 950, ATSS 960, NSS 970 and GSS 985, used in the simulation, are updated with data, at block 2288. With the aforementioned processes complete, the simulation block ends and the process moves to block 2222.

Communication Bus

The communication bus 750 allows the transfer of data between MSS components and subsystems. This covers all related hardware components, software, and middleware. The communication bus may be based on analog and/or digital signal, with various communication buses, for example: Ethernet, CAN bus, SATA, eSATA, IEEE 1394, RS-232, RS-485, USB, IEEE 488, CONTROLLERI, and I2C.

The communication bus 750 may be internal, external, or a combination thereof, and may be integrated with all MSS 75 systems and subsystems. The communication bus 750 may be driven, for example, by the system computer 470, or Controller 810. It may also be driven by external users, operators, or processes.

Database

The database 830 stores data from all MSS systems and provides access to it via the communication bus 750. A database, as used herein, may refer to one or more databases, which may be similar or dissimilar. For example, different types of data from various MSS 75 systems and subsystems may be best suited to databases with different characteristics. As such, the database 830 refers to the plurality of databases used in relation with the MSS 75.

The database 830 may be internal, external, or a combination thereof, and may be integrated with all MSS 75 systems and subsystems. The database 830 may be driven, for example, by the system computer 470, or Controller 810. It may also be driven by external users, operators, or processes.

The implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A system comprising:
a user receiving device to receive a user;
a force applying unit in communication with the user receiving device, the force applying unit including:
a first support operatively coupled to a base that is deployable on a surface that is substantially perpendicular to a gravity vector, the first support extending vertically relative to the surface when the base is deployed on the surface, and
a second support operatively coupled to the first support and substantially perpendicular to the first support, the second support being in communication with the user receiving device and being vertically moveable relative to the base to provide at least one of a positive force or a negative force to the user receiving device in a direction substantially parallel to the gravity vector, wherein the second support remains substantially perpendicular to the first support during vertical movement of the second support relative to the base; and
a mobility arrangement in communication with the base and configured for allowing movement of the user together with the user receiving device and the force applying unit in multiple degrees of freedom defined by: i) forward/backward, ii) left/right, and iii) 360-degree rotation about a yaw axis parallel to the gravity vector,
wherein the movement of the user allowed by the mobility arrangement is unrestricted by the system.

2. The system of claim 1, further comprising:
one or more sensors configured to obtain measurement data of forces being applied to the user in the user receiving device;
a controller configured to receive the measurements data from the one or more sensors; and
one or more actuators controlled by the controller and operating based on the measurements from the one or more sensors, the actuators configured to control vertical movement of the second support relative to the base so as to maintain the forces on the user.

3. The system of claim 2, further comprising:
at least one sensor of the one or more sensors electronically linked to the controller for measuring at least one of the motions, gestures, expression, gait, balance, posture, or stability, of the user.

4. The system of claim 1, wherein the at least one of the positive force or the negative force correspond to increased or decreased user bodyweight.

5. The system of claim 1, wherein the at least one of the positive force or the negative force is a predetermined force that corresponds to at least one of a predetermined gravity or a predetermined body weight.

6. The system of claim 1, wherein the user receiving device is configured for allowing user movement in a 360-degree rotation.

7. The system of claim 1, wherein the user receiving device is configured for allowing user movement in multiple degrees of freedom.

8. The system of claim 7, wherein the multiple degrees of freedom include angular degrees of freedom, defined by roll, pitch and yaw.

9. The system of claim 1, wherein the user receiving device includes a harness movably mounted in an adapter that is in communication with at least one arm that places the second support in communication with the user receiving device.

10. The system of claim 1, further comprising:
a locomotion support device, in communication with or integrated as part of the base, including a user surface for supporting the user in the user receiving device, wherein the locomotion support device includes at least one device selected from the group consisting of: a treadmill, an omnidirectional treadmill, and a stepper.

11. The system of claim 1, further comprising:
a visual stimulation system to provide a visual environment.

12. The system of claim 1, wherein the mobility arrangement includes a set of wheels operatively coupled to the base.

13. A system comprising:
a user receiving device to receive a user in a manner allowing for multidirectional rotational movement of the user;
a force applying unit including a base configured to be deployed on a surface that is substantially perpendicular to a gravity vector to support the force applying unit on the surface, a first support in communication with the base and extending vertically relative to the surface when the base is deployed on the surface, and a second support substantially perpendicular to the first support and in communication with the user receiving device, the second support being vertically moveable relative to the base to provide at least one of a positive force or a negative force to the user receiving device in a direction substantially parallel to the gravity vector, respectfully in negative or positive directions, wherein the second support remains substantially perpendicular to the first support during vertical movement of the second support relative to the base;
one or more sensors configured to obtain measurements of the forces being applied to the user in the user receiving device;
a controller including at least one processor configured to receive the measurements from the one or more sensors;
one or more actuators controlled by the controller and operating based on the measurements from the one or more sensors, the actuators configured to control the vertical movement of the second support relative to the base to maintain the forces on the user; and
a mobility arrangement in communication with the base and configured for allowing movement of the user together with the user receiving device and the force applying unit in multiple degrees of freedom defined by: i) forward/backward, ii) left/right, and iii) 360-degree rotation about a yaw axis parallel to the gravity vector,
wherein the movement of the user allowed by the mobility arrangement is unrestricted by the system.

14. The system of claim 13, wherein the user receiving device is configured for allowing the user to move in multiple directions.

15. The system of claim 13, wherein the user receiving device includes a harness movably mounted in a support member.

16. The system of claim 13, further comprising:
a visual stimulation system to provide a visual environment.

17. The system of claim 13, further comprising:
an omnidirectional treadmill in communication with or integrated as part of the base of the force applying unit, the omnidirectional treadmill for supporting the user in the user receiving device while allowing the user to move in multiple directions, and confining locomotion of the user to a predetermined area of the omnidirectional treadmill.

18. A method comprising:
obtaining a force applying unit having a base, a first support operatively coupled to the base, and a second support substantially perpendicular to the first support and in communication with a user receiving device, the second support being vertically moveable relative to the base;
deploying the base on a surface that is substantially perpendicular to a gravity vector such that the force applying unit is supported by the base on the surface and such that the first support extends vertically relative to the surface;
receiving a user in the user receiving device;
determining an applied force to be applied on the user;
actuating vertical movement of the second support relative to the base to apply the applied force to the user in the user receiving device, whereby the second support remains substantially perpendicular to the first support during the vertical movement;
continuously monitoring the applied force;
adjusting the applied force such that the applied force remains constant on the user; and
maintaining constant the applied force on the user.

19. The method of claim 18, further comprising:
providing at least one additional system for stimulating senses including neurological, olfactory, gustatory, or nervous systems.

20. The method of claim 18, further comprising: treating a mammalian medical condition, including one or more of: neurological condition; cerebrovascular accident; Parkinson's disease;
neurodegenerative disease; orthopedic conditions; cardiac conditions; respiratory conditions; vestibular conditions; and, musculoskeletal conditions.

21. The method of claim 18, further comprising:
obtaining measurement data from one or more sensors of the applied force being applied to the user in the user receiving device;
receiving at a controller the measurements data from the one or more sensors; and
operating one or more actuators based on the measurements from the one or more sensors, the actuators actively controlling the vertical movement of the second support relative to the base to maintain the applied force on the user.

22. A system comprising:
a user receiving device for receiving a user, the user receiving device including a ring configuration and configured for allowing unlimited 360-degree rotation of the user relative to at least part of the ring configuration and about a yaw axis parallel to a gravity vector; and
a force applying unit in communication with the user receiving device, the force applying unit including:
a first support operatively coupled to a base that is deployable on a surface that is substantially perpendicular to the gravity vector, the first support extending vertically relative to the surface when the base is deployed on the surface, and
a second support operatively coupled to the first support and substantially perpendicular to the first support, the second support being in communication with the user receiving device and being vertically moveable relative to the base to provide at least one of a positive force or a negative force to the user receiving device in a direction substantially parallel to the gravity vector, wherein the second support remains substantially perpendicular to the first support during vertical movement of the second support relative to the base.

* * * * *